United States Patent [19]

Nishitani et al.

[11] Patent Number: 5,703,243
[45] Date of Patent: Dec. 30, 1997

[54] INTERMEDIATES FOR PYRROLIDYLTHIOCARBAPENEM DERIVATIVE

[75] Inventors: Yasuhiro Nishitani, Izumi; Tadashi Irie, Suita; Yutaka Nishino, Neyagawa, all of Japan

[73] Assignee: Shionogi Seiyaku Kabushiki Kaisha, Osaka, Japan

[21] Appl. No.: 574,863

[22] Filed: Dec. 19, 1995

Related U.S. Application Data

[60] Continuation of Ser. No. 204,929, Mar. 1, 1994, abandoned, which is a division of Ser. No. 929,961, Aug. 14, 1992, Pat. No. 5,317,016.

[30] Foreign Application Priority Data

Aug. 20, 1991 [JP] Japan ................................. 3-207922
Feb. 21, 1992 [JP] Japan ................................. 4-35366

[51] Int. Cl.$^6$ ................................................ C07D 207/12
[52] U.S. Cl. .................... 548/541; 548/544; 548/556
[58] Field of Search .................................. 548/556, 544, 548/541

[56] References Cited

U.S. PATENT DOCUMENTS

| | | | |
|---|---|---|---|
| 4,260,543 | 4/1981 | Miller | 260/245.2 T |
| 4,822,787 | 4/1989 | Murata et al. | 514/210 |
| 4,962,103 | 10/1990 | Sunagawa et al. | 514/210 |
| 4,963,543 | 10/1990 | Murata et al. | 514/210 |
| 5,061,804 | 10/1991 | Murata et al. | 546/281 |
| 5,157,125 | 10/1992 | Braish et al. | 548/542 |

FOREIGN PATENT DOCUMENTS

| | | |
|---|---|---|
| 0182213 | 5/1986 | European Pat. Off. ...... C07D 487/04 |
| 0280771 | 9/1988 | European Pat. Off. ...... C07D 487/04 |
| 0433759 | 6/1991 | European Pat. Off. |
| 559090 | 3/1980 | Japan . |
| 60-233076 | 3/1985 | Japan . |
| 62-155279 | 6/1987 | Japan . |
| 63-179876 | 1/1988 | Japan . |

OTHER PUBLICATIONS

Burger, Medicinal Chemistry, Third Edition, Part I, John Wiley & Sons, 1970, pp.72–80.
Official Action dated Jul. 11, 1996 issued by Norwegian Patent Office for No. Application 923256.
Thornber; "Isosterism & Molecular Modification in Drug Design," *Imperial Chemical Indus.*, U.K., pp. 563–580.

*Primary Examiner*—Robert T. Bond
*Attorney, Agent, or Firm*—Renner, Otto, Boisselle & Sklar

[57] ABSTRACT

A pyrrolidylthiocarbapenem derivative represented by Formula I is provided:

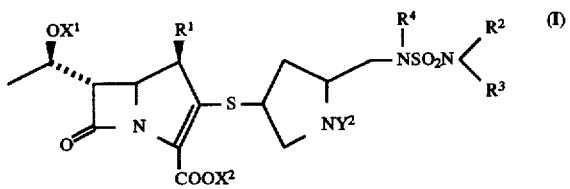

wherein $R^1$ is hydrogen or lower alkyl; $R^2$, $R^3$ and $R^4$ are hydrogen, lower alkyl which can be substituted or an amino protecting group independently, or $R^2$ and $R^3$ together with a nitrogen atom to which $R^2$ and $R^3$ are bonded form a saturated or unsaturated cyclic group, or $R^2$ and $R^4$, or $R^3$ and $R^4$ together with two nitrogen atoms and one sulfur atom in the sufamide group form a saturated or unsaturated cyclic group; each cyclic group can further include at least one atom selected from the group consisting of oxygen, sulfur and nitrogen, and each cyclic group can be substituted; $X^1$ is hydrogen or a hydroxy protecting group; $X^2$ is hydrogen, a carboxy protecting group, an ammonio group, an alkali metal or an alkaline-earth metal; and $Y^2$ is hydrogen or an amino protecting group.

18 Claims, No Drawings

INTERMEDIATES FOR PYRROLIDYLTHIOCARBAPENEM DERIVATIVE

This is a continuation of application Ser. No. 08/204,629 filed on Mar. 1, 1994, abandoned which is a divisional of application Ser. No. 07/929,961, filed Aug. 14, 1992 U.S. Pat. No. 5,317,016.

BACKGROUND OF THE INVENTION

1. Field of the Invention

The present invention relates to a new pyrrolidylthiocarbapenem derivative having a wide range of antibacterial spectrum, an antibacterial agent comprising the carbapenem derivative, a new pyrrolidine derivative which is an intermediate for producing the carbapenem derivative, and a method for producing the pyrrolidylthiocarbapenem derivative and the pyrrolidine derivative.

2. Description of the Prior Art

Various compounds are known as carbapenems, a kind of a β-lactam antibiotic. For example, imipenem, meropenem, the mesylate (mesylamino), and the urea derivatives of a carbapenem as shown below are known.

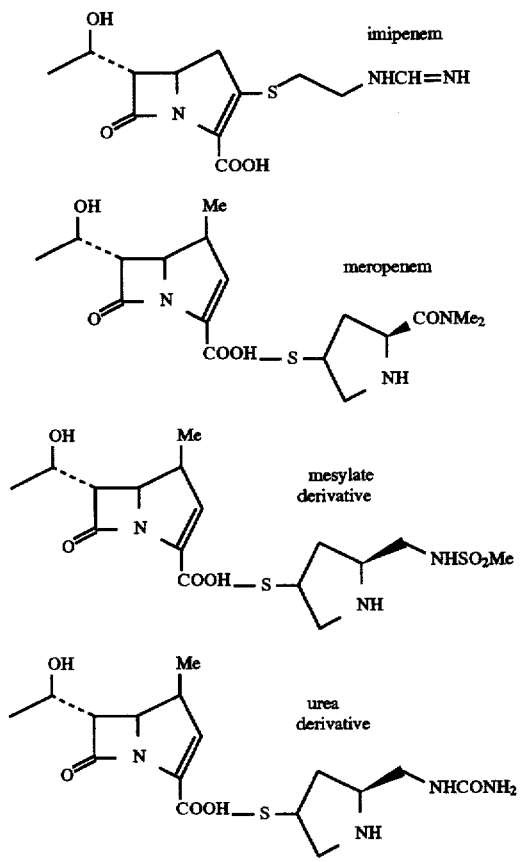

All of these compounds have a wide range of antibacterial spectrum, and are effective against both Gram-positive bacteria and Gram-negative bacteria. A carbapenem derivative having a wider range of antibacterial spectrum and a stronger antimicrobial activity has been desired.

SUMMARY OF THE INVENTION

The pyrrolidylthiocarbapenem derivative of this invention is represented by Formula I:

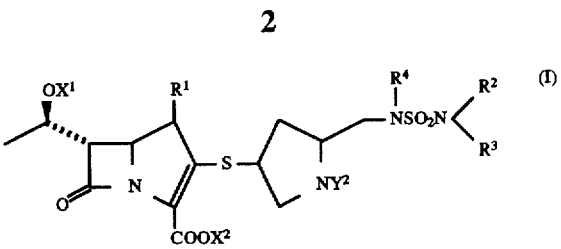

wherein $R^1$ is hydrogen or lower alkyl; $R^2$, $R^3$ and $R^4$ are hydrogen, lower alkyl which can be substituted or an amino protecting group independently, or $R^2$ and $R^3$ together with a nitrogen atom to which $R^2$ and $R^3$ are bonded form a saturated or unsaturated cyclic group, or $R^2$ and $R^4$, or $R^3$ and $R^4$ together with two nitrogen atoms and one sulfur atom in the sufamide group form a saturated or unsaturated cyclic group; each cyclic group can further include at least one atom selected from the group consisting of oxygen, sulfur and nitrogen, and each cyclic group can be substituted; $X^1$ is hydrogen or a hydroxy protecting group; $X^2$ is hydrogen, a carboxy protecting group, an ammonio group, an alkali metal or an alkaline-earth metal; and $Y^2$ is hydrogen or an amino protecting group.

In another aspect of the present invention, the pyrrolidine derivative of the present invention is represented by Formula II:

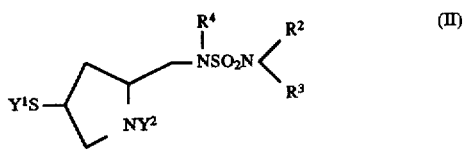

wherein $R^2$, $R^3$ and $R^4$ are hydrogen, lower alkyl which can be substituted, or an amino protecting group independently, or $R^2$ and $R^3$ together with a nitrogen atom to which $R^2$ and $R^3$ are bonded form a saturated or unsaturated cyclic group, or $R^2$ and $R^4$, or $R^3$ and $R^4$ together with two nitrogen atoms and one sulfur atom in the sufamide group form a saturated or unsaturated cyclic group; each cyclic group can further include at least one atom selected from the group consisting of oxygen, sulfur and nitrogen, and each cyclic group can be substituted; $Y^1$ is hydrogen or a mercapto protecting group; and $Y^2$ is hydrogen or an amino protecting group.

Alternatively, the present invention provides a method for producing a pyrrolidine derivative represented by Formula II:

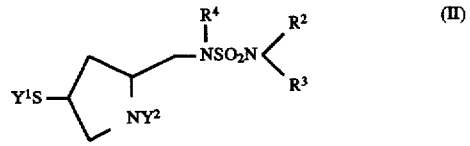

wherein $R^2$, $R^3$ and $R^4$ are hydrogen, lower alkyl which can be substituted, or an amino protecting group independently, or $R^2$ and $R^3$ together with a nitrogen atom to which $R^2$ and $R^3$ are bonded form a saturated or unsaturated cyclic group, or $R^2$ and $R^4$, or $R^3$ and $R^4$ together with two nitrogen atoms and one sulfur atom in the sufamide group form a saturated or unsaturated cyclic group; each cyclic group can further include at least one atom selected from the group consisting of oxygen, sulfur and nitrogen, and each cyclic group can be substituted; $Y^1$ is hydrogen or a mercapto protecting group; and $Y^2$ is hydrogen or an amino protecting group; and the method comprises the steps of: converting a hydroxy group at the 4-position of a 4-hydroxypyrrolidine-2-carboxylic acid derivative into a mercapto group; converting a carboxy group at the 2-position into a hydroxymethyl group; converting a hydroxy group in the hydroxymethyl group into an amino group or a sulfamoyl group; and converting the amino group into a sulfamoyl group.

Alternatively the present invention provides a method for producing a pyrrolidylthiocarbapenem derivative comprising the step of: allowing a carbapenem derivative to react with the pyrrolidine derivative of Formula II to obtain the pyrrolidylthiocarbapenem derivative of Formula I; the carbapenem derivative being represented by Formula III:

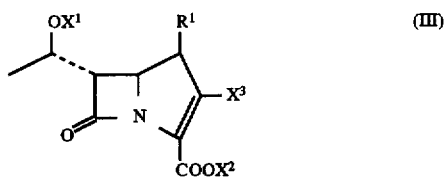

wherein $R^1$ is hydrogen or lower alkyl; $X^1$ is hydrogen or a hydroxy protecting group; $X^2$ is hydrogen, a carboxy protecting group, an ammonio group, an alkali metal or an alkaline-earth metal; and $X^3$ is a leaving group (e.g., reactive ester group of hydroxy, alkylsulfinyl arylsulfinyl, alkylsulfonyl, or arylsulfonyl).

Thus, the invention described herein makes possible the advantages of (1) providing a new carbapenem derivative having a strong antimicrobial activity and a wide range of antibacterial spectrum, and a method for producing the carbapenem derivative; (2) providing a new pyrrolidine derivative which is an intermediate for producing the carbapenem derivative, and a method for producing the pyrrolidine derivative; and (3) providing an antibacterial agent comprising the carbapenem derivative.

These and other advantages of the present invention will become apparent to those skilled in the art upon reading and understanding the following detailed description.

DESCRIPTION OF THE PREFERRED EMBODIMENTS

Followings are abbreviations used herein:
Ac: acetyl
Alz: allyloxycarbonyl
Boc: t-butoxycarbonyl
Et: ethyl
Ft: phthalyl
Me: methyl
Ms: methanesulfonyl
NPrc: protected amino
Ph: phenyl
PMB: p-methoxybenzyl
Pmz: p-methoxybenzyloxycarbonyl
PNB: p-nitrobenzyl
Pnz: p-nitrobenzyloxycarbonyl
Tr: trityl
Ts: p-toluenesulfonyl A preferred scope of each group herein is as follows:

The number of carbon atoms of "lower alkyl" is 1 to 6. Examples of such an alkyl group include methyl, ethyl, n-propyl, iso-propyl, n-butyl, t-butyl, pentyl and hexyl. The number of carbon atoms of the lower alkyl is preferably 1 to 4. The most preferred lower alkyl is methyl or ethyl. Examples of a substituent of "a substituted lower alkyl" include hydroxy, alkoxy, amino, acylamino, lower alkylamino, carbamoyl, lower alkylcarbamoyl, carbamoyloxy, lower alkylcarbamoyloxy and cyano. The number of carbon atoms of "aralkyl" is 7 to 15. Examples of "an amino protecting group" and "a hydroxy protecting group" include lower alkoxycarbonyl, lower alkenyloxycarbonyl, halogenoalkoxycarbonyl, aralkyloxycarbonyl, trialkylsilyl and diazo. An example of the lower alkoxycarbonyl includes t-butyloxycarbonyl; an example of the lower alkenyloxycarbonyl includes allyloxycarbonyl; examples of the halogenoalkoxycarbonyl include 2-iodoethyloxycarbonyl and 2,2,2-trichloroethyloxycarbonyl; examples of the aralkyloxycarbonyl include benzyloxycarbonyl, p-methoxybenzyloxycarbonyl, o-nitrobenzyloxycarbonyl, p-nitrobenzyloxycarbonyl and diphenylmethoxycarbonyl; examples of the trialkylsilyl include trimethylsilyl, triethylsilyl and t-butyldimethylsilyl.

In a definition of a group represented as follows:

a saturated or unsaturated cyclic group formed from $R^2$ and $R^3$ together with a nitrogen atom to which $R^2$ and $R^3$ are bonded can be, a saturated or unsaturated 3 to 8 membered residue further having one or more of nitrogen, sulfur and/or oxygen atoms, if necessary, and a 5 or 6 membered monocyclic residue including a hereto atom is preferable. The examples include pyrrolidin-1-yl, pyrrol-1-yl, imidazolidin-1-yl, imidazol-1-yl, pyrazolidin-1-yl, pyrazol-1-yl, piperidino, dihydro- or tetrahydropyridin-1-yl, piperazino, piperazin-1-yl which may have a substituent at the 4-position, morpholino and thiomorpholino. These groups may be substituted for one or more, preferably one or two, of the following groups: amino, protected amino, carbamoyl, lower alkyl, hydroxy, protected hydroxyl, lower alkoxy, oxo, lower alkylsulfonyl, hydroxy lower alkyl, carbamoyl lower alkyl, lower alkoxycarbonyl and cyano. Moreover, when the cyclic group is imidazolidin-1-yl, pyrazolidin-1-yl or piperazin-1-yl, the imino moiety thereof may be protected by a imino protecting group which is known in the art.

In the definition of the group IIa, a saturated or unsaturated cyclic group formed from $R^2$ and $R^4$, or $R^3$ and $R^4$ can be a saturated or unsaturated 5 to 7 membered residue having 2 to 3 nitrogen atoms and one sulfur atom and if necessary, having an another hetero atom such as an oxygen atom, and 5 to 6 membered monocyclic residue including a hereto atom is preferable. Such a residue may include, if necessary, a substituent such as lower alkyl, halogen, lower alkoxy, acyloxy, hydroxy, amino, lower alkylamino, acylamino and oxo, and/or an unsaturated bond. The examples include 1,1-dioxothiadiazinyl, 1,1-dioxodihydrothiadiazinyl, 1,1,3-trioxodihydrothiadiazinyl, 1,1-dioxothiadiazolizinyl, 1,1-dioxothiadiazolinyl, and 1,1,3-trioxothiadiazolinyl.

The "carboxy protecting group" is selected from those used in the art and serve the function of blocking the carboxyl group while reactions are carried out at other sites of the molecule. Such group generally contains less than about 19 carbon atoms and bind to a carboxyl group reversibly without affecting the other parts of the molecule. Typical examples include following groups: optionally substituted $C_1$–$C_8$ alkyl, for example, methyl, methoxymethyl, ethyl, ethoxymethyl, iodomethyl, propyl, isopropyl, butyl, isobutyl, ethoxyethyl, methylthioethyl, methanesulfonylethyl, trichloroethyl, t-butyl, and the like; optionally substituted $C_3$–$C_8$ alkenyl, for example, propenyl, allyl, isoprenyl, hexenyl, phenylpropenyl, dimethylhexenyl, and the like; optionally substituted $C_7$–$C_{19}$ aralkyl, for example, benzyl, methylbenzyl, dimethylbenzyl, methoxybenzyl, ethoxybenzyl, nitrobenzyl, aminobenzyl, diphenylmethyl, phenylethyl, trityl, di-t-butylhydroxybenzyl, phthalidyl, phenacyl, and the like; optionally substituted $C_6$–$C_{12}$ aryl, for example, phenyl, toluyl diisopropylphenyl, xylyl, trichlorphenyl, pentachlorophenyl, indanyl, and the like; optionally substituted $C_1$–$C_{12}$ amino which is, e.g., an ester with acetone oxime, acetophenone oxime, acetoaldoxime, N-hydroxysuccineimide, N-hydroxyphthalimide, or the like; optionally substituted $C_3$–$C_{12}$ hydrocarbonated silyl, for example, trimethylsilyl, dimethylmethoxysilyl, t-butyldimethylsilyl, and the like; optionally substituted $C_3$–$C_{12}$ hydrocarbonated stannyl, for example, trimethylstannyl, and the like. Another carboxy protecting group is a pharmaceutically active ester forming group. Examples of such a group include following groups: 1-(oxygen-substituted)-$C_2$ to $C_{15}$ alkyl groups, for example, a straight, branched, ringed, or partially ringed alkanoyloxyalkyl, such as acetoxymethyl, acetoxyethyl, propionyloxymethyl, pivaloyloxyethyl, pivaloyoxyethyl, cyclohexaneacetoxyethyl, cyclohexanecarbonyloxycyclohexylmethyl, end the like; $C_3$–$C_{15}$ alkoxycarbonyloxyalkyl such as ethoxycabonyloxyethyl, and the like; $C_2$–$C_8$ alkoxyalkyl, such as methoxymethyl, methoxyethyl, and the like; $C_4$–$C_8$ 2-oxacycloalkyls, such as tetraphdropyranyl, tetrahydrofuranyl, and the like; substituted $C_8$–$C_{12}$ aralkyls, for example, phenacyl, phthalidyl, and the like; $C_6$–$C_{12}$ aryl, for example, phenyl, xylyl, indanyl, and the like; $C_2$–$C_{12}$ alkenyl, for example, allyl, isoprenyl, 2-oxo-1,3-dioxolyl-4-yl-methyl, and the like. Among the above, a protecting group used to block the carboxyl group during reactions is usually removed at the final step of the reaction, and therefore its structure is not essential. Thus, as one of skilled in the art can easily appreciate, the carboxy protecting group can be selected from various equivalent groups including amides, acid anhydrides formed with carbonic acid or carboxylic acids, and the like as long as an aimed carboxyl group is protected properly.

An example of the lower alkyl includes t-butyl; examples of the lower alkenyl include allyl, isopentenyl and 2-butenyl; examples of the halogeno lower alkyl include 2-iodoethyl and 2,2,2-trichloroethyl; examples of the lower alkoxymethyl include methoxymethyl, ethoxymethyl and isobutoxymethyl; examples of the lower aliphatic acyloxymethyl include acetoxymethyl, propionyloxymethyl, butyryloxymethyl and pivaloyloxymethyl; examples of the 1-lower alkoxycarbonyloxyethyl include 1-methoxycarbonyloxyethyl and 1-ethoxycarbonyloxyethyl; and examples of the aralkyl include benzyl, p-methoxybenzyl, o-nitrobenzyl, p-nitrobenzyl and diphenylmethyl. Examples of "an alkali metal" include lithium, sodium and potassium, and sodium or potassium is preferred. Examples of "an alkaline-earth metal" include magnesium and calcium.

As "a mercapto protecting group", a conventional one, e.g., acyl and aryl substituted lower alkyl such as benzyl, phenethyl, trityl and benzhydryl are included. As "a reactive ester group of hydroxy", a conventional one, e.g., a residue such as substituted or unsubstituted arylsulfonyloxy, lower alkanesulfonyloxy, halogeno lower alkanesulfonyloxy, dialkylphosphonyloxy, diarylphosphoryloxy and halogeno are included. Examples of the arylsulfonyloxy include benzenesulfonnyloxy, p-toluenesulfonyloxy, p-nitrobenzenesulfonyloxy and p-bromobenzenesulfonyloxy; examples of the lower alkanesulfonyloxy include methanesulfonyloxy and ethanesulfonyloxy; an example of the halogeno lower alkanesulfonyloxy includes trifluoromethanesulfonyloxy; an example of the dialkylphospheoryloxy includes diethylphosphoryloxy; an example of the diarylphosphoryloxy includes diphenylphosphoryloxy; and examples of the halogeno include chloro, bromo and iodo.

An example includes "an alkylsulfinyl group" includes methylsulfinyl, and an example of "an arylsulfinyl group" includes phenylsulfinyl.

The pyrrolidylthiocarbapenem derivative of the present invention is represented by the following Formula I:

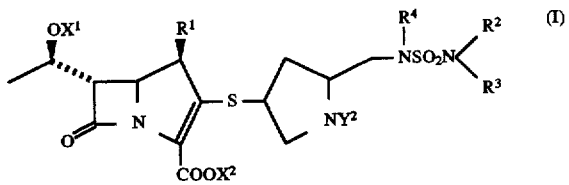

wherein $R^1$ is hydrogen or lower alkyl; $R^2$, $R^3$ and $R^4$ are hydrogen, lower alkyl which can be substituted or an amino protecting group independently, and preferably $R^4$ is hydrogen, or $R^2$ and $R^3$ together with a nitrogen atom to which $R^2$ and $R^3$ are bonded form a saturated or unsaturated cyclic group, or $R^2$ and $R^4$, or $R^3$ and $R^4$ together with two nitrogen atoms and one sulfur atom in the sufamide group form a saturated or unsaturated cyclic group and each cyclic group can further include at least one atom selected from the group consisting of oxygen, sulfur and nitrogen, and each cyclic group can be substituted; $X^1$ is hydrogen or a hydroxy protecting group; $X^2$ is hydrogen, a carboxy protecting group, an ammonio group, an alkali metal or an alkaline-earth metal; and $Y^2$ is hydrogen or an amino protecting group.

When the above pyrrolidylthiocarbapenem derivative I has a free —OH, —COOH, amino group, imino group, or substituted amino group, the pyrrolidylthiocarbapenem also includes pharmaceutically acceptable salts thereof. The same is the case with an intermediate compound for synthesizing the pyrrolidylthiocarbapenem derivative such as the pyrrolidine derivative represented by Formula II. Examples of the pharmaceutically acceptable salts include a salt with a base, a salt with an acid, a salt with a basic or acidic amino acid and an intermolecular or intramolecular quarternary salt. Examples of the salt with a base include alkali metal salts such as sodium salt and potassium salt; alkaline-earth metal salts such as calcium salt and magnesium salt; ammonium salt; and organic amine. salts such as triethylamine salt, pyridine salt, picoline salt, ethanolamine salt, triethanolamine salt, dicyclohexylamine salt, N,N'-dibenzylethylenediamine salt and dibenzylamine salt. Examples of the salt with an acid include inorganic acid addition salts such as hydrochloride, hydrobromide, sulfuric acid salt and phosphoric acid salt; and organic acid addition salts such as formic acid salt, acetic acid salt, trifluoroacetic acid salt, maleic acid salt, tartaric acid salt, methanesulfonic acid salt, benzenesulfonic acid salt and toluenesulfonic acid salt. Examples of the salt with an amino acid include a salt with arginine, aspartic acid or glutamic acid.

The pyrrolidylthiocarbapenem derivative (I) of the present invention can be produced in the steps of: by using, for example, 4-hydroxypyrrolidine-2-carboxylic acid or the derivative thereof as a starting material, obtaining a pyrrolidine derivative II represented by the following formula:

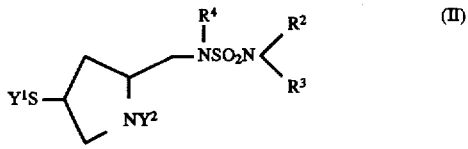

wherein $R^2$, $R^3$ and $R^4$ are hydrogen, lower alkyl which can be substituted, or an amino protecting group independently, and $R^4$ is preferably hydrogen, or $R^2$ and $R^3$ together with a nitrogen atom to which $R^2$ and $R^3$ are bonded form a saturated or unsaturated cyclic group, or $R^2$ and $R^4$, or $R^3$ and $R^4$ together with two nitrogen atoms and one sulfur atom in the sufamide group form a saturated or unsaturated cyclic group; each cyclic group can further include one atom selected from the group consisting of oxygen, sulfur and nitrogen, and each cyclic group can be substituted; $Y^1$ is hydrogen or a mercapto protecting group; and $Y^2$ is hydrogen or an amino protecting group; and allowing the obtained pyrrolidine derivative II to react with a carbapenem derivative represented by the following Formula III:

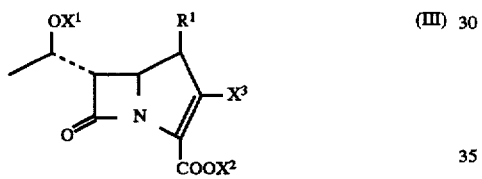

wherein $R^1$ is hydrogen or lower alkyl; $X^1$ is hydrogen or a hydroxy protecting group; $X^2$ is hydrogen, a carboxy protecting group, an ammonio group, an alkali metal or an alkaline-earth metal; and $X^3$ is leaving group (e.g., a reactive ester of hydroxy, alkylsulfinyl, arylsulfinyl, alkylsulfonyl, or arylsulfonyl).

The present invention also includes a pyrrolidine derivative represented by the following Formula II:

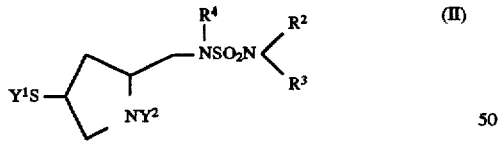

wherein $R^2$, $R^3$ and $R^4$ are hydrogen, substituent lower alkyl which can be substituted, or an amino protecting group independently, and $R^4$ is preferably hydrogen, or $R^2$ and $R^3$ together with a nitrogen atom to which $R^2$ and $R^3$ are bonded form a saturated or unsaturated cyclic group, or $R^2$ and $R^4$, or $R^3$ and $R^4$ together with two nitrogen atoms and one sulfur atom in the sufamide group form a saturated or unsaturated cyclic group; each cyclic group can further include at least one atom selected from the group consisting of oxygen, sulfur and nitrogen, and each cyclic group can be substituted; $Y^1$ is hydrogen or a mercapto protecting group; and $Y^2$ is hydrogen or an amino protecting group.

The pyrrolidine derivative II is prepared according to the steps of converting a hydroxy group at the 4-position of a 4-hydroxypyrrolidine-2-carboxylic acid derivative into a mercapto group; converting a carboxy group at the 2-position into a hydroxymethyl group; directly sulfamidating a hydroxy group in the hydroxymethyl group or sulfamoylating it after converting it into an amino group; and removing the protecting group $Y^1$ if necessary. The order of these steps can be properly changed.

Synthesis of pyrrolidine derivative II

Pyrrolidine derivative II is synthesized, for example, in the following process, but is not limited to.

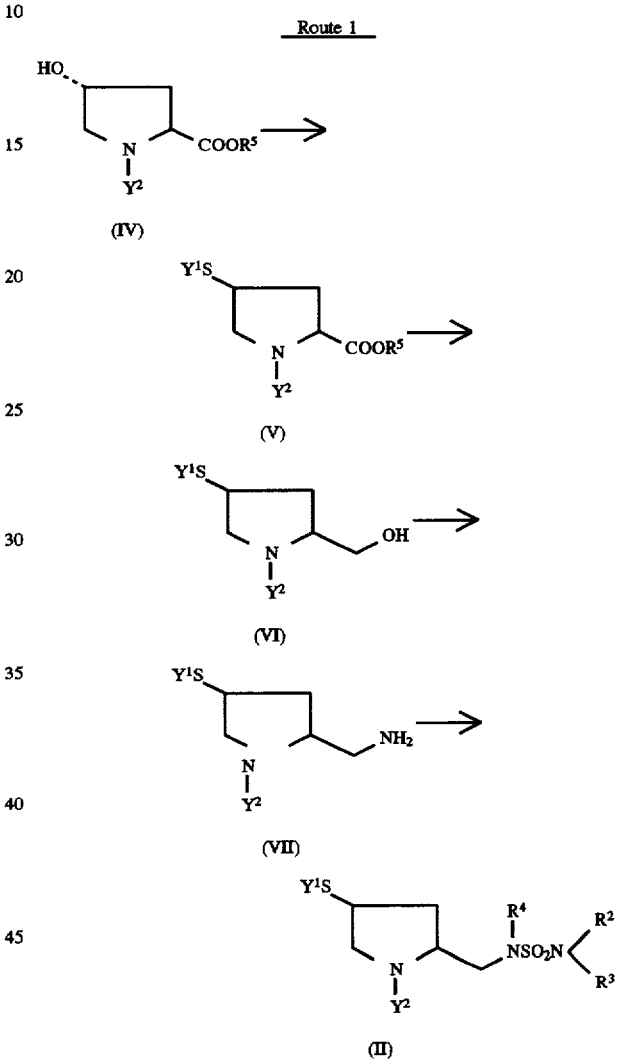

Route 1

In the above scheme, $R^2$, $R^3$ and $R^4$ are the same as defined for Formula I, and $R^5$ is a group for forming an ester together with a carboxy group such as lower alkyl. $Y^1$ and $Y^2$ are the same as defined for Formulas I and II, but denote a mercapto protecting group and an amino protecting group, respectively, at the intermediate of the reaction route.

In this process, for example, 4-hydroxypyrrolidine-2-carboxylic acid derivative IV is first provided. A mesyl group or the like is introduced to the hydroxy group at the 4-position of compound IV, and then a protected mercapto group such as a tritylthio group is introduced to the 4-position. In this way, a compound V is obtained. Then, a compound VI is obtained by reducing a carboxylate group at the 2-position. An azide group is introduced to the compound VI, and the azide group is converted to an amino group, or phthalimide is reacted with the compound VI, and the formed phthalyl group is removed from the compound VI, thereby introducing an amino group at a position of the hydroxy group of the compound VI. Thus, a compound VII is obtained. A sulfamoyl group is then introduced to the compound VII to obtain a compound II.

Furthermore, the process of Route 1 can be variously modified. For example, after introducing a protected mercapto group to the 4-position of the compound IV, a carboxylate group is reduced and then a sulfamide group is introduced to obtain the compound II. Alternatively, after reducing the compound IV, a protected mercapto group and a sulfamide group are successively introduced to obtain the compound II.

group to the hydroxy group of the compound VIII to increase the reactivity. Next, a mercapto group protected by thioacetate and the like (represented by $Y^1S$) is introduced to the 4-position (see a compound X), and removing the protection to obtain a compound XI. By introducing a sulfamoyl group to the compound XI, a compound II-1 (a compound II wherein the —SY' at the 2-position of the pyrrolidine ring is SH) is obtained.

Furthermore, the process of Route 2 can be variously modified. For example, by introducing a protected mercapto group to the 4-position of the compound VIII, further introducing a sulfamoyl group and removing the protection, the compound II-1 is obtained.

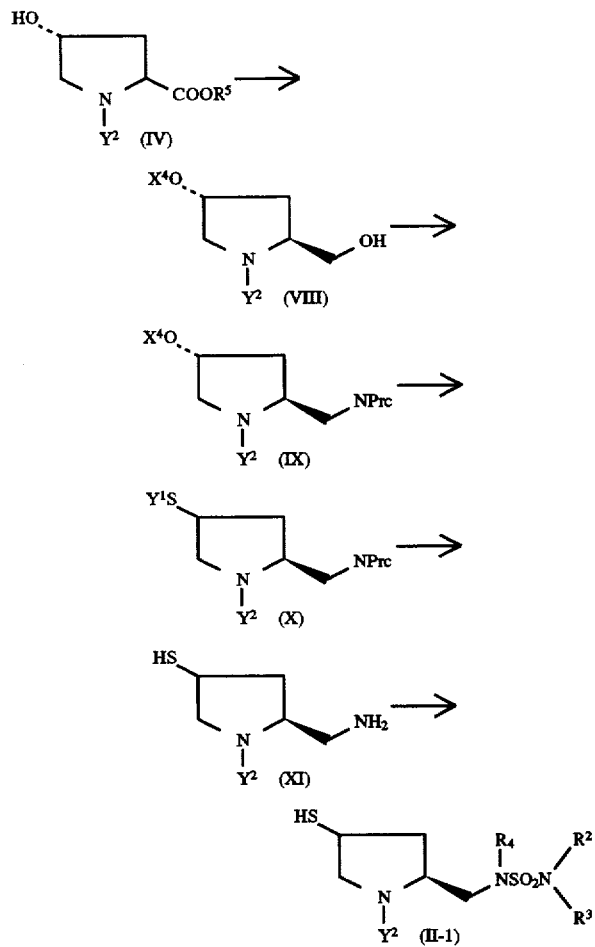

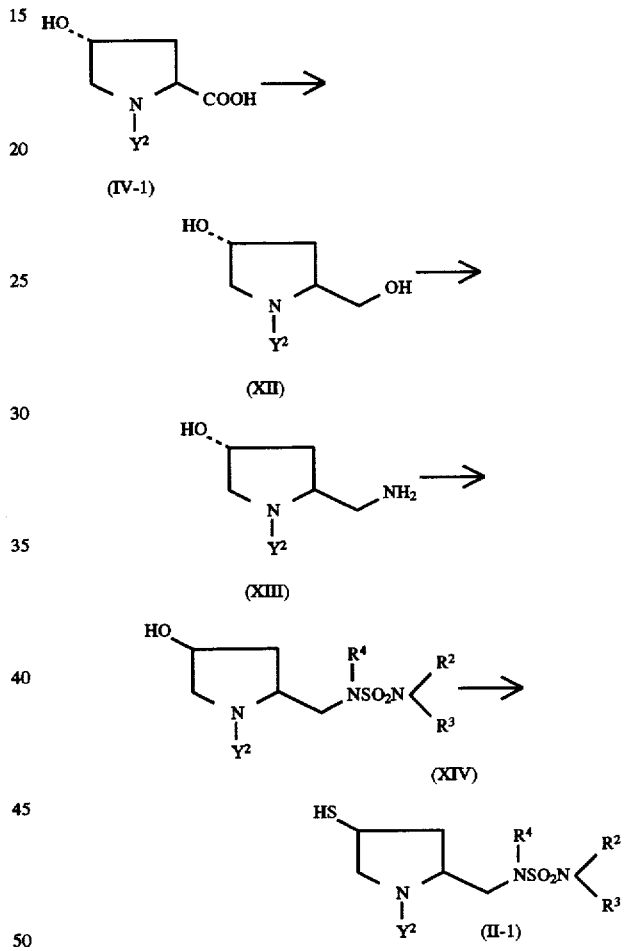

In the above scheme, $R^2$, $R^3$ and $R^4$ are the same as defined in Formula I, and $R^5$ is a group for forming ester together with a carboxy group such as lower alkyl. $Y^1$ and $Y^2$ are the same as defined in Formulas I and II, but denote a mercapto protecting group and an amino protecting group, respectively, at the intermediate of the reaction route. $X^4$ is a hydroxy protecting group.

In this process, for example, a mesyl group or the like (represented by $X^4$) is first introduced to the 4-position of the 4-hydroxypyrrolidine-2-carboxylic acid derivative IV, then a carboxylate group is reduced to a hydroxymethyl group as is in Route 1 to obtain a compound VIII. Then, a protected amino group such as a phthalimide group is introduced to a position of a hydroxy group in the hydroxymethyl group. Thus a compound IX is obtained. In introducing the protected amino group, it is effective to introduce a leaving In the above scheme, $R^2$, $R^3$ and $R^4$ are the same as defined in Formula I. $Y^2$ is the same as defined in Formula I but denotes a protecting amino group at the intermediate of the reaction route.

In this method, chloroformate or the like is first allowed to react with 4-hydroxypyrrolidine-2-carboxylic acid IV-1 having protected nitrogen in the pyrrolidine ring. A carboxy group at the 2-position is then converted into a hydroxymethyl group by reduction. Next, after converting a hydroxy group in the hydroxymethyl group into a reactive ester and introducing a protected amino group, a compound XIII is obtained by removing the protection. A sulfamoyl group is introduced to the compound XIII resulting in a compound XIV, then, a protected mercapto group is introduced to a position of the hydroxy group at the 4-position. A compound II-1 is obtained by removing the protection of the mercapto group.

Synthesis of a pyrrolidylthiocarbapenem derivative

The protection of the 4-position of the pyrrolidine derivative is removed to obtain an SH compound, if necessary, then, the pyrrolidine derivative is allowed to react with a carbapenem derivative represented by the following Formula III to give a pyrrolidylthiocarbapenem derivative I of the present invention:

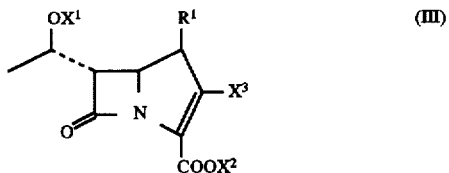

wherein $R^1$ is hydrogen or lower alkyl; $X^1$ is hydrogen or a hydroxy protecting group; $X^2$ is hydrogen, a carboxy protecting group, an ammonio group, an alkali metal or an alkaline-earth metal; $X^3$ is a leaving group (e.g., reactive ester group of hydroxy, alkylsulfinyl, arylsulfinyl, alkylsulfonyl, or arylsufonyl).

The protection is removed from the compound I if necessary to give a compound having free carboxy, hydroxy and/or amino.

An antibacterial agent comprising the pyrrolidylthiocarbapenem derivative

A pharmaceutical composition comprising the pyrrolidylthiocarbapenem derivative (including pharmaceutically acceptable salts thereof) of the present invention is administered as an antibacterial agent. An administration method is in oral administration or parenteral administration; as injection (a formulation in an ampoule or vial, a liquid, a suspension or the like for an intravenous injection, an intramuscular injection, a drip infusion, or subcutaneous injection), an external or local administration agent (an ear drop, a nasal drop, an ophthalmic solution, an ointment, an emulsion, a spray, a suppository and the like), and an oral preparation. Preferably, the composition is administered by injection, through skin or mucosa. The pharmaceutical composition includes at least 0.01% by weight of the pyrrolidylthiocarbapenem derivative and further includes an appropriate excipient, auxiliary agent, stabilizer, wetting agent, emulsifier, and other additives depending upon the administration method. These additives must be pharmaceutically and pharmacologically acceptable materials which do not inhibit the effect of the pyrrolidylthiocarbapenem derivative and which show no adverse effects on patients. For example, lactose, stearic acid, magnesium stearate, clay, sucrose, cornstarch, talc, gelatin, agar, pectin, peanut oil, olive oil, cacao butter, ethylene glycol, tartaric acid, citric acid and fumaric acid can be contained in the oral preparation. For parenteral administration, a solvent (e.g., alcohol, a buffer, methyl oleate, water or the like), a buffer solution, a dispersing agent, a dissolving auxiliary agent, a stabilizer (e.g., methyl p-hydroxybenzoate, ethyl p-hydroxybenzoate, sorbic acid or the like), an absorbefacient (mono- or dioctanoate of glycerin), an antioxidant, a perfume, an analgetic, a dispersing agent, an adverse effect inhibitor, an action potentiator (an agent for regulating absorption and elimination, an inhibitor for enzyme decomposition, a β-lactamase inhibitor, and other kinds of antimicrobial agents) and the like can be contained in the formulation.

A dose of the pyrrolidylthiocarbapanem derivative of the present invention depends upon the age of a patient, the type and the state of the disease and the kind of compounds to be used. Generally, daily dose ranges from 1 mg/patient to about 4000 mg/patient, but more can be administered if necessary. For example, a dose of 1 mg (the external application) is administered 4 times a day, and a dose of 1000 mg (intravenous injection) is administered 2 to 4 times a day to treat an infection.

Characteristics of the pyrrolidylthiocarbapenem derivative

The characteristics of the pyrrolidylthiocarbapenem derivative of the present invention as an antibacterial agent will now be described as compared with same known compounds.

(1) Antimicrobial activity

A minimum growth inhibitory concentration and an effect for preventing bacterial infection of the pyrrolidylthiocarbapenem derivative of the present invention are compared with those of meropenem (Japanese Laid Open Patent Publication No. 60-233076) and imipenem (Japanese Laid Open Patent Publication No. 55-9090), respectively to find that the derivative of the present invention is superior to meropenem against Gram positive bacteria and superior to imipenem against Gram negative bacteria. The derivative of the present invention has an antibacterial potency against *Pseudomonas aeruginosa*, a kind of a Gram negative bacteria, equal to or twice as that of imipenem, meropenem and the mesylamino derivative of a carbapenem (Japanese Laid Open Patent Publication No. 63-179876). When compared with the urea derivative of a carbapenem (Japanese Laid Open Patent Publication No. 62-155279), the derivative has equal to or twice the antibacterial potency against Gram positive bacteria, twice the potency against the Gram negative bacteria and twice to eight times the potency against *Pseudomonas aeruginosa*.

(2) Rabbit nephrotoxicity test

An administration of the derivative of the present invention of 250 mg per 1 kg of the body weight of a rabbit reveals no toxicity. The same result is obtained by an administration of meropenem. When 150 mg/kg of imipenem is administered, medium renal toxicity is revealed. Sugar and protein are found in urine and a white microgranular change in the kidney is found.

(3) Rate of decomposition by mouse renal dehydropeptidase 1

The enzymatic decomposition rate of the pyrrolidylthiocarbapenem derivative of the present invention by the action of renal dehydropeptidase I is 76% of that of imipenem, 40% of that of meropenem to show higher stability.

(4) Solubility in water

The solubility in water of the derivative of the present invention is 10% or more in a form of free acid, enabling an intravenous injection. In contrast, the solubility of imipenem and meropenem is about 2% and they cannot be administered except for a drip infusion.

(5) Pharmacokinetics in vivo

When the derivative of the present invention is intravenously injected to a cynomolgus (10 mg/kg), the half-life is 1.1 hours, a recovery from urine is 62.2%, and an integrated value of a concentration in blood is 24.9 µg.hr/ml. The half-life is 1.44 times, the recovery from urine is 1.36 times and the integrated value of a concentration in blood (Area under the curve: AUC) is 1.44 times as much as those of meropenem. The half-life is 1.87 times, the recovery from urine is 1.93 times, and AUC is 1.87 times as much as those of imipenem.

When the derivative is intravenously injected into a mouse (20 mg/kg), the recovery from urine is 36.3%, and the integrated value of a concentration in blood is 12.1 µg.hr/ml. The recovery from urine is 2.18 times and AUC is 2.32 times as much as those of meropenem. The recovery from urine is 1.15 times and AUC is 1.37 times as much as those of imipenem. The recovery from urine is 1.48 times as much as that of mesylate derivative of meropenem.

In this way, the present invention provides a new pyrrolidylthiocarbapenem derivative having a wide range of antibacterial spectrum and a strong antimicrobial activity against both Gram positive bacteria and Gram negative bacteria, an antibacterial agent (composition) comprising the carbapenem derivative, and a method for preparing the carbapenem derivative. Furthermore, a new pyrrolidin derivative as an intermediate for preparing the carbapenem derivative and a method for preparing the same are provided.

A minimum bacterial growth inhibitory concentration and an effect for preventing bacterial infection of the pyrrolidylthiocarbapenem derivative of the present invention are compared with those of meropenem and imipenem, respectively to find that the derivative of the present invention is superior to meropenem against Gram positive bacteria and superior to imipenem against Gram negative bacteria. The derivative of the present invention has an antibacterial potency against Pseudomonas aeruginosa, a kind of a Gram negative bacterium, equal to or twice of that of imipenem, meropenem and the mesylamino derivative of a carbapenem. When compared with the urea derivative of a carbapenem, the derivative has an equal or twice the antibacterial potency against Gram positive bacteria, twice the potency against the Gram negative bacteria and twice to eight times the potency against Pseudomonas aeruginosa. The pyrrolidylthiocarbapenem derivative is less toxic to an organism than the conventional carbapenem derivatives.

Since the derivative decomposes slowly in a body, the antimicrobial effect thereof lasts for a longer period of time. Moreover, since the derivative has a higher solubility in water than the conventional carbapenem derivatives, it can be applicable for injection.

Following Examples are given to show the present invention, but not to limit the scope thereof.

PREPARATIVE EXAMPLE 1 OF A PYRROLIDINE DERIVATIVE

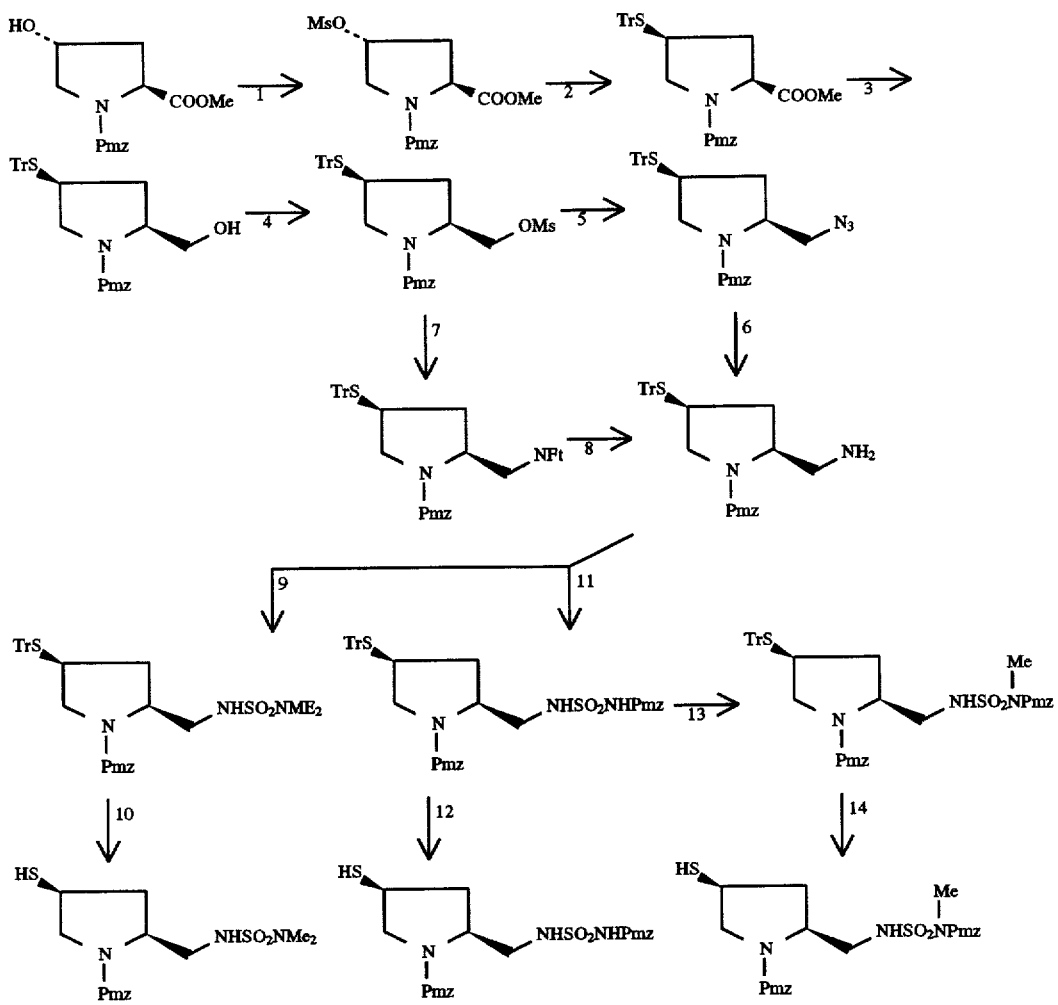

Step 1. Preparation of an O-mesyl compound

To a solution of (2S,4R)-1-p-methoxybenzyloxycarbonyl-4-hydroxypyrrolidine-2-carboxylic acid methyl ester (227.2 g: 0.735 mole) in dichloromethane (1.3 liter) stirring at −30° C., triethylamine (112.5 ml: 1.1 eq.) and methanesulfonyl chloride (56.8 ml: 1 eq.) are added. The mixture is stirred at the same temperature for 15 minutes. The reaction mixture is successively washed with dilute hydrochloric acid and water, dried over magnesium sulfate, and concentrated in vacuo to give (2S,4R)-1-p-methoxybenzyloxy-carbonyl-4-methanesulfonyloxypyrrolidine-2-carboxylic acid methyl ester (280.1 g). Yield: 98%.

NMR δ (CDCl$_3$) ppm: 3.02, 3.04(2×s, 3H), 3.56, 3.78(2×s, 3H), 3.81(s, 3H), 4.98, 5.08(ABq, J=12 Hz, 1H), 5.04, 5.12(ABq, J=12 Hz, 1H).

IR ν (CHCl$_3$) cm$^{-1}$: 1755, 1709, 1620.

Step 2. Preparation of a tritylthio compound

To a solution of triphenylmethylmercaptan (107.02 g: 1.5 eq.) in dimethylformamide (350 ml), an oil suspension containing 60% sodium hydride (13.42 g: 1.3 eq.) is added with stirring at 0° C. The mixture is stirred at room temperature for 1 hour. The reaction mixture is mixed with a solution of (2S,4R)-1-p-methoxybenzyloxycarbonyl-4-methanesulfonyloxypyrrolidine-2-carboxylic acid methyl ester (100 g: 0.258 mole) in dimethylformamide(70 ml) with stirring at 0° C. The mixture is stirred at 60° C. for 30 minutes. The reaction mixture is poured into cold dilute hydrochloric acid, and extracted with ethyl acetate. The extract is successively washed with water and brine, dried, and concentrated in vacuo. The residue is purified by silica gel column chromatography (toluene: ethyl acetate=5:1) to give (2S,4S)-1-p-methoxybenzyloxycarbonyl-4-tritylthiopyrrolidine-2-carboxylic acid methyl ester (127.1 g). Yield: 87%.

NMR δ (CDCl$_3$) ppm: 3.50, 3.71(2×s, 3H), 3.78, 3.84(2×s, 3H), 4.87, 5.13(ABq, J=12 Hz, 1H), 4.89, 5.13(ABq, J=12 Hz, 1H).

IR ν (CHCl$_3$) cm$^{-1}$: 1750, 1700, 1618.

Step 3. Preparation of a methylol compound

To a solution of (2S,4S)-1-p-methoxybenzyloxycarbonyl-4-tritylthiopyrrolidine-2-carboxylic acid methyl ester (127.1 g: 0.224 mole) in tetrahydrofuran (1 liter ), lithium borohydride (4.88 g: 1 eq.) is added with stirring at room temperature. The mixture is stirred at 60° C. for 30 minutes. The reaction mixture is allowed to cool to room temperature and water (100 ml) is added in small portions with stirring. The formed precipitate is removed by filtration and the filtrate is concentrated in vacuo. The residue is dissolved in dichloromethane, dried over magnesium sulfate, and concentrated under reduced pressure. The residue is washed with ether to give (2S,4S)-1-p-methoxybenzyloxycarbonyl-4-tritylthiopyrrolidine-2-methanol as white crystals (82.3 g). Yield: 68%.

NMR δ (CDCl$_3$) ppm: 3.84(s, 3H), 4.93, 4.99(ABq, J=12 Hz, 2H).

IR ν (CHCl$_3$) cm$^{-1}$: 3400, 1668, 1610.

Step 4. Preparation of a mesyl compound

A solution of (2S,4S)-1-p-methoxybenzyloxycarbonyl-4-tritylthiopyrrolidine-2-methanol (22.33 g: 41.37 mmole) is diluted with dichloromethane (300 ml) and the mixture is cooled to −30° C. To this mixture, triethylamine (6.92 ml: 1.2 eq.) and methanesulfonyl chloride (3.52 ml: 1.1 eq.) are added, and the mixture is stirred for 20 minutes. The reaction mixture is successively washed with dilute hydrochloric acid and water, dried over magnesium sulfate, and filtered. The filtrate is concentrated in vacuo to give crude (2S,4S)-1-p-methoxybenzyloxycarbonyl-4-tritylthiopyrrolidine-2-methanol methanesulfonate (27.81 g: 45.02 mmole). Yield: 100%.

NMR δ (CDCl$_3$) ppm: 2.89(s, 3H), 3.81, 3.83(2×s, 3H), 4.85 to 5.07(m, 2H).

IR ν (CHCl$_3$) cm$^{-1}$: 1725, 1690, 1610.

Step 5. Preparation of an azide compound

To a solution of (2S,4S)-1-p-methoxybenzyloxycarbonyl-4-tritylthiopyrrolidine-2-methanol methanesulfonate (27.81 g ) in dimethylformamide (120 ml), a solution (12 ml) of sodium azide (3.50 g: 53.8 mmole) in water is added. The mixture is stirred at 80° C. for 8 hours. The reaction mixture is poured into ice water and extracted with ethyl acetate. The extract is successively washed with water and brine and concentrated. The residue is purified by silica gel column chromatography to give (2S, 4S)-1-p-methoxybenzyloxycarbonyl-2-azidomethyl-4-tritylthiopyrrolidine (17.27 g: 30.64 mmole). Total yield of Steps 4 and 5:74%.

NMR δ (CDCl$_3$) ppm: 3.84(s, 3H), 4.82 to 5.15(m, 2H).

IR ν (CHCl$_3$) cm$^{-1}$: 2105, 1685.

Step 6. Preparation of an amino compound

A solution of (2S, 4S)-1-p-methoxybenzyloxycarbonyl-2-azidomethyl-4-tritylthiopyrrolidine (17.27 g: 30.64 mmole) in a mixture of ethyl acetate (150 ml), methanol (200 ml), and acetic acid (2.63 ml: 46 mmole) is subjected to conventional hydrogenation over 5% palladium on carbon (5 g). After the reaction, the catalyst is filtered off and the filtrate is concentrated in vacuo to give (2S,4S)-1-p-methoxybenzyloxycarbonyl-2-aminomethyl-4-tritylthiopyrrolidine acetate (17.33 g) as a residue. The residue is dissolved in dichloromethane, washed with aqueous sodium hydrogen carbonate, and concentrated to give (2S,4S)-2-aminomethyl-1-p-methoxybenzyloxycarbonyl-4-tritylthiopyrrolidine (16.82 g).

Step 7. Preparation of a phthalimido compound

Crude (2S,4S)-1-p-methoxybenzyloxycarbonyl-4-tritylthiopyrrolidine-2-methanol methanesulfonate (115.4 g ) produced from (2S,4S)-1-p-methoxybenzyloxycarbonyl-4-tritylthiopyrrolidine-2-methanol (96.24 g: 178 mmole) in the same manner as in the above-mentioned Step 4 is dissolved in dimethylformamide (1 liter). After adding potassium phthalimide (65.94 g: 2 eq.), the mixture is stirred at 100° C. for 1 hour. The reaction mixture is poured into ice water and extracted with ethyl acetate. The extract is successively washed with water and brine, and concentrated. The residue is purified by silica gel column chromatography (toluene: ethyl acetate) to give (2S,4S)-1-p-methoxybenzyloxycarbonyl-2-phthalimidomethyl-4-tritylthiopyrrolidine (99.4 g). Yield: 83.5%.

NMR δ (CDCl$_3$) ppm: 3.78, 3.84(2×s, 3H), 4.65 to 5.00(m, 2H).

IR ν (CHCl$_3$) cm$^{-1}$: 1770, 1712, 1693, 1611.

Step 8. Removal of a phthalyl group

To a solution of (2S,4S)-1-p-methoxybenzyloxycarbonyl-2-phthalimidomethyl-4-tritylthiopyrrolidine (752 mg: 1.124 mmole) in a mixture of dichloromethane (3 ml) and methanol (12 ml), hydrazine hydrate (109 μl: 2 eq.) is added. The mixture is heated for 5 hours. The reaction mixture is concentrated in vacuo. The residue is dissolved in dichloromethane (5 ml) and the solid is filtered off. The filtrate is washed with water and concentrated in vacuo. The residue is recrystallized from a mixture of dichloromethane and methanol to give (2S,4S)-1-p-methoxybenzyloxycarbonyl-2-aminomethyl-4-tritylthiopyrrolidine (471 mg). Yield: 78%. mp. 165° to 167° C.

NMR δ (CDCl$_3$:CD$_3$OD=2:1) ppm: 3.46(s, 3H), 4.96, 4.89(ABq, J=12 Hz, 2H).

IR ν (CHCl$_3$) cm$^{-1}$: 1683, 1610.

Step 9. Preparation of a dimethylsulfamoyl compound

A solution of (2S,4S)-1-p-methoxybenzyloxycarbonyl-2-aminomethyl-4-tritylthiopyrrolidine (12.44 g: 23.13 mmole) in dichloromethane(70 ml) is cooled to −78° C. After adding triethylamine (4.21 ml: 1.3 eq.) and dimethylaminosulfonyl chloride (2.73 ml: 1.1 eq.), the mixture is warmed to room temperature over about 1 hour. The reaction mixture is successively washed with dilute hydrochloric acid and brine, and concentrated to give crude (2S,4S)-1-p-methoxybenzyloxycarbonyl-2-N,N-dimethylsulfamoylaminomethyl-4-tritylthiopyrrolidine (15.02 g). Yield: 100%.

Step 10. Preparation of a mercapto compound by deprotection

To a solution of (2S,4S)-1-p-methoxybenzyloxycarbonyl-2-N,N-dimethylsulfamoylaminomethyl-4-tritylthiopyrrolidine (3.55 g: 5.5 mmole) in a mixture of dichloromethane (70 ml) and methanol (35 ml), a solution of pyridine (0.66 ml: 1.5 eq.) and silver nitrate (1.40 g: 1.5 eq.) in water (3.5 ml) is added under ice cooling. The mixture is stirred for 10 minutes. The reaction mixture is poured into water and extracted with dichloromethane. The extract is dried over magnesium sulfate, bubbled with hydrogen sulfide, and filtered to remove solid. The filtrate is concentrated in vacuo and the residue is purified by silica gel column chromatography (toluene: ethyl acetate) to give (2S,4S)-1-p-methoxybenzyloxycarbonyl-2-N,N-dimethyl sulfamoylaminomethyl-4-mercaptopyrrolidine (1.93 g ). Yield: 87.0%.

NMR δ (CDCl$_3$) ppm: 2.77(s, 6H), 3.81(s, 3H), 5.00 to 5.12(m, 2H).

IR ν (CHCl$_3$) cm$^{-1}$: 3380, 1690, 1610.

Step 11. Preparation of a sulfamoyl compound

To a solution of chlorosulfonyl isocyanate (3.95 ml: 45.4 mmole) in dichloromethane (70 ml), p-methoxybenzyl alcohol (5.66 ml: 45.4 mmole) is added at −50° C. The mixture is stirred at −50° C. for 15 minutes. The resulting solution of p-methoxybenzyloxycarbonylsulfamoyl chloride is added to a solution of (2S,4S)-1-p-methoxybenzyloxycarbonyl-2-aminomethyl-4-tritylthiopyrrolidine (obtained in the above Steps 6 or 8) (12.21 g: 22.7 mmole) and triethylamine (6.38 ml: 45.6 mmole) in dichloromethane (300 ml) at −78° C., and the mixture is stirred for 10 minutes, successively washed with dilute hydrochloric acid and brine, and concentrated in vacuo. The residue is purified by silica gel column chromatography to give (2S,4S)-1-p-methoxybenzyloxycarbonyl-2-p-methoxybenzyloxycarbonylsulfamoylaminomethyl-4-tritylthiopyrrolidine (16.31 g). Yield: 91.6%.

NMR δ (CDCl$_3$) ppm: 3.78(s, 3H), 3.81, 3.83(2×s, 3H), 4.98, 4.89(ABq, J=12 Hz, 2H), 5.09, 5.03(ABq, J=12 Hz, 2H).

IR ν (CHCl$_3$) cm$^{-1}$: 3390, 1740, 1685.

Step 12. Preparation of a mercapto compound by deprotection

To a solution of (2S,4S)-1-p-methoxybenzyloxycarbonyl-2-p-methoxybenzyloxycarbonylsulfamoylaminomethyl-4-tritylthiopyrrolidine (2.35 g: 3.13 mmole) in a mixture of dichloromethane (60 ml) and methanol (30 ml), a solution of pyridine (0.38 ml: 4.75 mmole: 1.5 eq.) and silver nitrate (0.80 g: 1.5 eq.) in water (2 ml) is added under ice cooling. The mixture is stirred for 10 minutes. The reaction mixture is poured into water and extracted with dichloromethane. The extract is dried over magnesium sulfate and filtered. Hydrogen sulfide is passed through the filtrate and the resulting precipitate is filtered off. The filtrate is concentrated in vacuo and the residue is purified by silica gel column chromatography to give (2S,4S)-1-p-methoxybenzyloxycarbonyl-2-p-methoxybenzyloxycarbonylsulfamoylaminomethyl-4-mercaptopyrrolidine (1.56 g). Yield: 92.4%.

NMR δ (CDCl$_3$) ppm: 2.42 to 2.58(m, 1H), 3.80(s, 6H), 5.08, 5.02(ABq, J=12 Hz, 2H), 5.12, 5.07(ABq, J=16 Hz, 2H).

IR ν (CHCl$_3$)cm$^{-1}$: 3380, 1740, 1685, 1610.

Step 13. Preparation of an N-methyl compound

To a solution of (2S, 4S)-1-p-methoxybenzyloxycarbonyl-4-tritylthio-2-(p-methoxybenzyloxycarbonylaminosulfonylaminomethyl) pyrrolidine (2.06 g: 2.63 mmole) in dimethylformamide (15 ml), a solution of 1M-lithium bis(trimethylsilyl)amide in tetrahydrofuran (2.76 ml: 1.05 eq.) is added with stirring under ice cooling. After stirring for 1 hour, iodomethane (491 μl: 3 eq.) is added. The mixture is stirred at the same temperature for 3 hours. The reaction mixture is poured into a mixture of ethyl acetate and aqueous sodium sulfite and the ethyl acetate layer is taken. The organic layer is successively washed with water and brine, dried over magnesium sulfate, and concentrated in vacuo. The residue is purified by silica gel column chromatography (toluene: ethyl acetate=4:1) to give (2S,4S)-1-p-methoxybenzyloxycarbonyl-4-tritylthio-2-(N-p-methoxybenzyloxycarbonyl-N-methylaminosulfonyl-amino)methylpyrrolidine (1.51 g). Yield: 72%.

NMR δ (CDCl$_3$) ppm: 1.4 to 1.6(m, 1H), 1.9 to 2.1(m, 1H), 2.5 to 3.3(m, 4H), 3.23(s, 3H), 3.5 to 3.8(m, 1H), 3.76(s, 3H), 3.81(s, 3H), 4.93(ABq,J=10.4 Hz, 2H), 5.10 (ABq, J=15.2 Hz, 2H), 6.35 to 6.55(m, 1H), 6.8 to 7.5(m, 23H).

IR ν (CHCl$_3$) cm $^{-1}$: 1727, 1695.

Step 14. Preparation of a mercapto compound by deprotection

To a solution of (2S,4S)-1-p-methoxybenzyloxycarbonyl-4-tritylthio-2-(N-p-methoxybenzyloxycarbonyl-N-methylaminosulfonyl)aminomethylpyrrolidine (1.5 g: 1.88 mmole) in a mixture of dichloromethane (4 ml) and methanol (10 ml), a solution of pyridine (381 μl: 2.5 eq.) and silver nitrate (640 mg: 2 eq.) in water (6 ml) is added with stirring under ice cooling. The mixture is stirred at the same temperature for 30 minutes. The reaction mixture is diluted with dichloromethane, washed with water, dried over magnesium sulfate, and concentrated in vacuo to about 5 ml. The residue is dissolved in methanol (10 ml) and hydrogen sulfide is bubbled through it. The mixture freed from solid by filtering is concentrated in vacuo. The residue is purified by silica gel column chromatography (toluene: ethyl acetate=2:1) to give (2S,4S)-1-p-methoxybenzyloxycarbonyl-4-mercapto-2-(N-p-methoxybenzyloxycarbonyl-N-methylaminosulfonyl) aminomethylpyrrolidine (866 mg). Yield: 83%.

NMR δ (CDCl$_3$) ppm: 1.6 to 1.8(m, 1H), 2.3 to 2.6(m, 1H), 2.9 to 3.4(m, 5H), 3.3(s, 3H), 3.8(s, 6H), 3.8 to 4.2(m, 1H), 6.3 to 6.6(m, 1H), 6.88(d, J=8.6 Hz, 2H), 7.2 to 7.4(m, 2H).

IR ν (CHCl$_3$) cm$^{-1}$: 1690.

PREPARATIVE EXAMPLE 2 OF A PYRROLIDINE DERIVATIVE

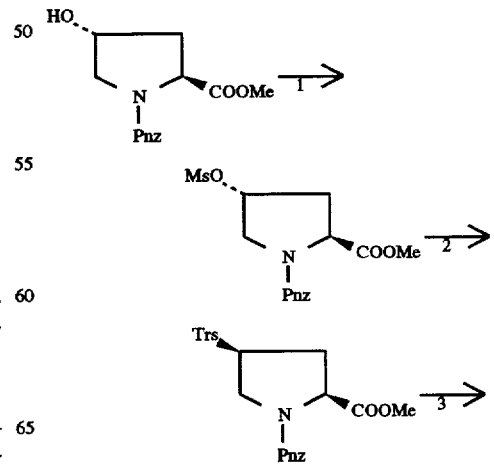

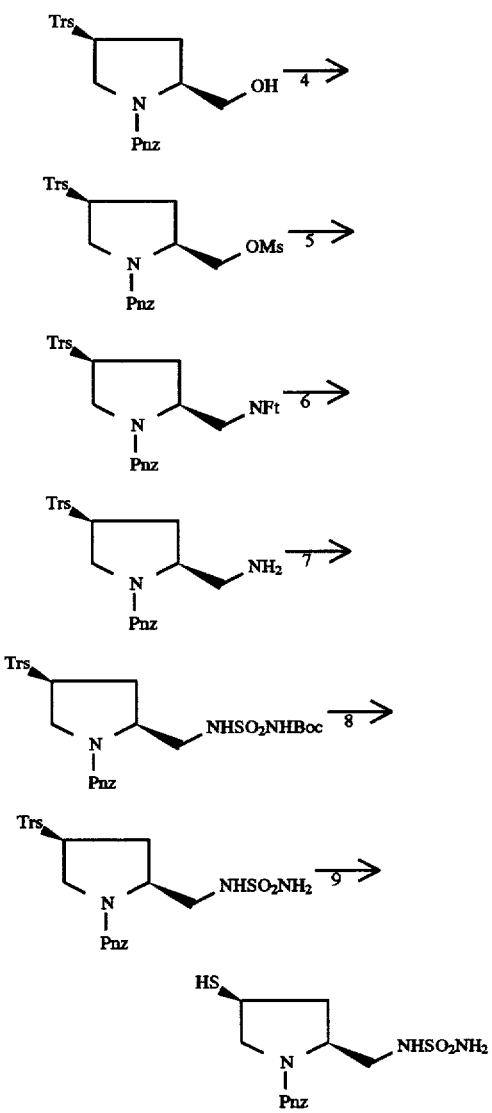

Step 1 Preparation of an O-mesyl compound

To a solution of (2S,4R)-1-p-nitrobenzyloxycarbonyl-4-hydroxypyrrolidine-2-carboxylic acid methyl ester (59.44 g: 0.183 mole) in dichloromethane (150 ml) stirring at −20° C., triethylamine (30.5 ml: 1.2 eq.) and methanesulfonyl chloride (17 ml: 1 eq.) are added. The mixture is stirred at the same temperature for 35 minutes. To the mixture is added ice water and ethyl acetate. The organic layer is taken, washed with water, dried over magnesium sulfate, and concentrated in vacuo to give (2S,4R)-1-p-nitrobenzyloxycarbonyl-4-methanesulfonyloxypyrrolidine-2-carboxylic acid methyl ester (74.05 g). Yield: Quantitative.

NMR δ (CDCl₃) ppm: 2.20 to 2.42(m, 1H), 2.55 to 2.85(m, 1H), 3.07(s, 3H), 3.67(s, 1.5H), 3.78(s, 1.5H), 3.80 to 4.05(m, 2H), 4.53(t, J=7 Hz, 1H), 5.06 to 5.40(m, 3H), 7.47(d, J=9 Hz, 1H), 7.51(d, J=9 Hz, 1H), 8.23(d, J=9 Hz, 2H).

IR ν (CHCl₃) cm⁻¹: 1748, 1712, 1608.

Step 2. Preparation of a tritylthio compound

To a solution of tritylmercaptan (37.69 g: 1.5 eq.) in tetrahydrofuran (180 ml), an oil suspension containing 60% sodium hydride (4.73 g: 1.3 eq.) is added with stirring at 0° C. The mixture is stirred at room temperature overnight. A solution of (2S,4R)-1-p-nitrobenzyloxycarbonyl-4-methanesulfonyloxypyrrolidine-2-carboxylic acid methyl ester (36.58 g: 90.9 mmole) in tetrahydrofuran (180 ml) is added to the reaction mixture with stirring at 0° C., and the mixture is stirred at 60° C. for 30 minutes. The reaction mixture is poured into cold dilute hydrochloric acid and extracted with ethyl acetate. The extract is successively washed with water and brine, dried, and concentrated in vacuo. The residue is purified by silica gel column chromatography (toluene: ethyl acetate=9:1 to 4:1) to give (2S,4S)-1-p-nitrobenzyloxycarbonyl-4-tritylthiopyrrolidine-2-carboxylic acid methyl ester (25.48 g). Yield: 48.1%.

NMR δ (CDCl₃) ppm: 1.63 to 2.35(m, 2H), 2.68 to 3.50(m, 3H), 3.60(s, 1.5H), 3.72(s, 1.5H), 4.02 to 4.15(m, 1H), 4.95 to 5.28(m, 2H), 7.10 to 7.52(m, 17H), 8.17(d, J=9 Hz, 1H).

IR ν (CHCl₃) cm⁻¹: 1747, 1704, 1607.

Step 3. Preparation of a methylol compound

To a solution of (2S,4S)-1-p-nitrobenzyloxycarbonyl-4-tritylthiopyrrolidine-2-carboxylic acid methyl ester (5 g: 9.01 mmole) in tetrahydrofuran (180 ml) stirring under ice cooling, a solution of sodium borohydride (2.3 g: 1.4 eq.) in ethanol and a solution of lithium chloride (2.76 g: 1.5 eq.) in tetrahydrofuran (60 ml) are added. The mixture is stirred at room temperature for 1 hour. The reaction mixture is poured into a mixture of ice water and ethyl acetate and extracted with ethyl acetate. The extract is successively washed with cold dilute hydrochloric acid, aqueous sodium hydrogen carbonate, and saturated brine, dried over magnesium sulfate, and concentrated in vacuo. The residue is recrystallized from methanol to give (2S,4S)-1-p-nitrobenzyloxycarbonyl-4-tritylthiopyrrolidine-2-methanol (15.9 g). Yield: 65.9%. mp. 122° to 125° C.

NMR δ (CDCl₃) ppm: 1.32 to 1.53(m, 1H), 1.90 to 2.12(m, 1H), 2.65 to 3.05(m, 3H), 3.32 to 3.84(m, 3H), 5.08, 5.17(ABq, J=12 Hz, 2H), 7.08 to 7.55(m, 17H), 8.26(d, J=9 Hz, 2H).

IR ν (CHCl₃) cm⁻¹: 3400 br, 1681, 1607.

Step 4. Preparation of a mesyl compound

To a solution of (2S,4S)-1-p-nitrobenzyloxycarbonyl-4-tritylthiopyrrolidine-2-methanol (5.0 g: 9.01 mmole) in dichloromethane (50 ml) stirring at −15° C., triethylamine (1.63 ml: 1.3 eq.) and methanesulfonyl chloride (0.85 ml: 1.1 eq.) are added. The mixture is stirred at −15° to −10° C. for 30 minutes. The reaction mixture is poured into water and extracted with dichloromethane. The extract is successively washed with dilute hydrochloric acid, aqueous sodium hydrogen carbonate, and water, dried over magnesium sulfate, and concentrated in vacuo. The residue is purified by silica gel column chromatography (toluene: ethyl acetate=9:1) to give (2S,4S)-1-p-nitrobenzyloxycarbonyl-4-tritylthiopyrrolidine-2-methanol methanesulfonate (4.86 g). Yield: 85.2%.

NMR δ (CDCl₃) ppm: 1.65 to 1.93(m, 1H), 2.00 to 2.26(m, 1H), 2.68 to 2.92(m, 3H), 2.96(s, 3H), 3.78 to 3.98(m, 1H), 4.16 to 4.30(m, 1H), 4.38 to 4.52(m, 1H), 5.11(br s, 2H), 7.08 to 7.52(m, 17H), 8.24(d, J=9 Hz, 2H).

IR ν (CHCl₃) cm⁻¹: 1699, 1606.

Step 5. Preparation of a phthalimido compound

A solution of (2S,4S)-1-p-nitrobenzyloxycarbonyl-4-tritylthiopyrrolidine-2-methanol methanesulfonate (4.39 g: 6.93 mmole) and potassium phthalimide (2.57 g: 2 eq.) in dimethylformamide (30 ml) is stirred at 70° C. for 6 hours. The reaction mixture is poured into ice water and the precipitate is filtered off. The precipitate is dissolved in ethyl acetate, washed with saturated brine, dried over magnesium sulfate, and concentrated in vacuo. The residue is purified by silica gel column chromatography (toluene: ethyl acetate) to give (2S,4S)-1-p-nitrobenzyloxycarbonyl-2-phthalimidomethyl-4-tritylthiopyrrolidine (3.12 g). Yield: 64.3%.

NMR δ (CDCl₃) ppm: 1.40 to 2.30(m, 2H), 2.60 to 3.08(m, 2H), 3.10 to 3.40(m, 1H), 3.55 to 4.23(m, 3H), 4.92, 5.06(ABq, J=12 Hz, 2H), 7.08 to 7.50 (m, 17H), 7.60 to 7.82(m, 4H), 8.10(d, J=9 Hz, 1H), 8.19(d, J=9 Hz, 1H).

IR ν (CHCl₃) cm⁻¹: 1720, 1701, 1607.

Step 6. Removal of a phthalyl group

To a solution of (2S,4S)-1-p-nitrobenzyloxycarbonyl-2-phthalimidomethyl-4-tritylthiopyrrolidine (10.46 g: 15.31 mmole) in a mixture of dichloromethane (80 ml) and methanol (160 ml), hydrazine hydrate (1.53 ml: 2 eq.) is added, and the mixture is concentrated to remove dichloromethane by warming and refluxed for 3 hours and 15 minutes. The reaction mixture is concentrated in vacuo. The residue is diluted with dichloromethane and filtered to remove solid. The filtrate is washed with water, dried over magnesium sulfate, and concentrated in vacuo to give crude (2S,4S)-1-p-nitrobenzyloxycarbonyl-2-aminomethyl-4-tritylthiopyrrolidine (7.71 g). Yield: 91%.

NMR δ (CDCl₃: CD₃OD=2:1) ppm: 1.46 to 3.76(m, 10H), 5.04, 5.12(ABq, J=15 Hz, 2H), 7.10 to 7.56(m, 17H), 8.12 to 8.30(m, 2H).

IR ν (CHCl₃) cm⁻¹: 1695, 1606.

Step 7. Preparation of an N-sulfamoyl compound

A solution of (2S,4S)-1-p-nitrobenzyloxycarbonyl-2-aminomethyl-4-tritylthiopyrrolidine (4.7 g: 8.49 mmole) is dissolved in dichloromethane (45 ml) and cooled to a temperature of −70° C. To the mixture, a solution of diisopropylethylamine (3.4 ml: 2.3 eq.) and 1M t-butoxycarbonylaminosulfonyl chloride (prepared from chlorosulfonyl isocyanate and t-butanol before hand) in dichloromethane (21 ml), and the mixture is stirred for 1 hour and diluted with ice water. The reaction mixture is successively washed with dilute hydrochloric acid and aqueous sodium hydrogen carbonate, dried over magnesium sulfate, and concentrated. The residue is purified by silica gel column chromatography (toluene: ethyl acetate) to give (2S,4S)-1-p-nitrobenzyloxycarbonyl-2-t-butoxycarbonyl-aminosulfonylaminomethyl-4-tritylthiopyrrolidine (1.49 g). Yield: 24%.

NMR δ (CDCl₃) ppm: 1.40 to 2.30(m, 2H), 1.44(s, 9H), 2.60 to 3.40(m, 5H), 3.71 to 3.95(m, 1H), 5.08, 5.13(ABq, J=12 Hz, 2H), 6.27(br s, 1H), 7.07 to 7.55(m, 17H), 8.21(d, J=7 Hz, 1H), 8.26(d, J=7 Hz, 1H).

IR ν (CHCl₃) cm⁻¹: 3390, 1737, 1695, 1606.

Step 8. Removal of a Boc group

To a solution of (2S, 4S)-1-p-nitrobenzyloxycarbonyl-2-t-butoxycarbonylaminosulfonylaminomethyl-4-tritylthiopyrrolidine (1.46 g: 2 mmole) in dichloromethane (5 ml) under ice cooling, anisole (2.4 ml) and trifluoroacetic acid (3.9 ml) are added. The mixture is stirred at room temperature for 2 hours. The reaction mixture is diluted with ethyl acetate and ice water and extracted with ethyl acetate. The extract is successively washed with water and saturated brine, dried over magnesium sulfate, and concentrated in vacuo. The residue is recrystallized from n-hexane to give (2S,4S)-1-p-nitrobenzyloxycarbonyl-2-sulfamoylaminomethyl-4-tritylthiopyrrolidine (1.4 g). Yield: Nearly quantitative.

NMR δ (CDCl₃) ppm: 1.43 to 1.70(m, 1H), 2.08 to 2.30(m, 1H), 2.65 to 3.50(m, 5H), 3.74 to 4.00(m, 1H), 5.03, 5.13(ABq, J=15 Hz, 2H), 5.73(br s, 1H), 7.00 to 7.60(m, 17H), 8.25(d, J=9 Hz, 2H).

IR ν (CHCl₃) cm⁻¹: 3334 br, 1688, 1607.

Step 9. Preparation of a mercapto compound by deprotection

To a solution of (2S,4S)-1-p-nitrobenzyloxycarbonyl-2-sulfamoylaminomethyl-4-tritylthiopyrrolidine (668 mg: 0.95 mmole) in tetrahydrofuran (6 ml), a solution of pyridine (0.254 ml: 2.7 eq.) and silver nitrate (403 mg: 2.5 eq.) in water (2 ml) is added under ice cooling. The mixture is stirred at room temperature for 1 hour. The reaction mixture is diluted with dichloromethane (3 ml) and methanol(3 ml), and hydrogen sulfide is bubbled through it under ice cooling for 10 minutes. The resulting precipitate is removed by filtering. The filtrate is diluted with dichloromethane, washed with water, dried over magnesium sulfate, and concentrated in vacuo. The residue is purified by silica gel column chromatography (toluene: ethyl acetate) to give (2S,4S)-1-p-nitrobenzyloxycarbonyl-2-sulfamoylaminomethyl-4-mercaptopyrrolidine (233 mg). Yield: 63%.

NMR δ (CDCl₃-CD₃OD) ppm: 1.42(t, J=7 Hz, 1H), 1.65 to 1.93(m, 1H), 2.48 to 2.70(m, 1H), 3.05 to 3.63(m, 4H), 3.93 to 4.16(m, 2H), 5.22(s, 2H), 7.53(d, J=8 Hz, 2H), 8.23(d, J=8 Hz, 2H).

IR ν (CHCl₃) cm⁻¹: 3276 br, 1692, 1607.

PREPARATIVE EXAMPLE 3 OF A PYRROLIDINE DERIVATIVE

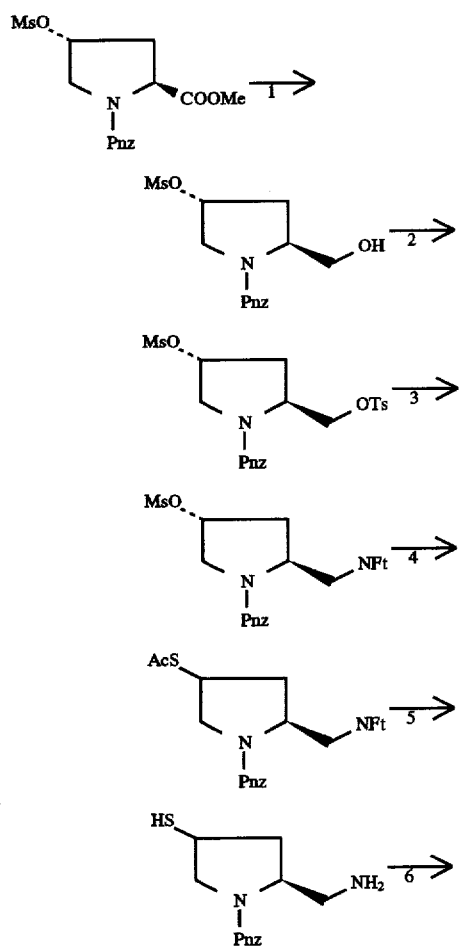

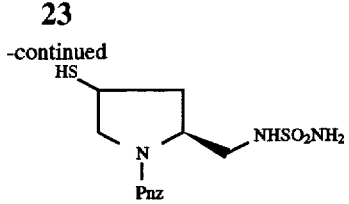

Step 1. Preparation of a methylol compound

To a solution of (2S,4R)-1-p-nitrobenzyloxycarbonyl-4-methanesulfonyloxypyrrolidine-2-carboxylic acid methyl ester (79.4 g: 0.197 mmole) in a mixture of ethanol (300 ml) and tetrahydrofuran (150 ml), sodium borohydride (10.44 g: 1.4 eq.) is added in small portions with stirring at 0° C. The mixture is stirred at 0° C. for 1.5 hours and at room temperature for 5 hours. To the reaction mixture under ice cooling, 5N-hydrochloric acid (100 ml) is added. The mixture is diluted with water, and extracted with ethyl acetate. The extract is washed with brine, dried over sodium sulfate, and concentrated in vacuo. The residue is recrystallized from a mixture of dichloromethane and ether to give (2S,4R)-1-p-nitrobenzyloxycarbonyl-4-methanesulfonyloxypyrrolidine-2-methanol (51.9 g). Yield: 70%.

NMR δ (CDCl$_3$) ppm: 1.93 to 2.14(m, 1H), 2.32 to 2.48(m, 1H), 3.06(s, 3H), 3.53 to 4.28(m, 6H), 5.26(s, 2H), 7.53(d, J=9 Hz, 2H), 8.24(d, J=9 Hz, 2H).

IR ν (CHCl$_3$) cm$^{-1}$: 3404, 1698, 1607.

Step 2. Preparation of a tosyl compound

To a solution of (2S,4R)-1-p-nitrobenzyloxycarbonyl-4-methanesulfonyloxypyrrolidine-2-methanol (28.8 g: 77 mmole) in dichloromethane (150 ml) under ice cooling, p-toluenesulfonyl chloride (19.11 g: 1.3 eq.), triethylamine (10.4 ml: 1.3 eq.) and dimethylaminopyridine (0.94 g: 0.1 eq.) are added. The mixture is stirred at 25° C. for 7 hours. The reaction mixture is diluted with ice water. The resultant organic layer is taken, successively washed with aqueous sodium hydrogen carbonate and water, dried over magnesium sulfate, and concentrated in vacuo. The residue is recrystallized from n-hexane to give (2S,4R)-1-p-nitrobenzyloxycarbonyl-4-methanesulfonyloxypyrrolidine-2-methanol p-toluenesulfonate (37.7 g). Yield: 93%.

NMR δ (CDCl$_3$) ppm: 2.20 to 2.50(m, 1H), 2.44(s, 3H), 3.05(s, 3H), 3.45 to 4.60(m, 5H), 5.18(s, 2H), 5.26(br s, 1H), 7.34(d, J=8 Hz, 2H), 7.50(d, J=8 Hz, 2H), 7.75(d, J=8 Hz, 2H), 8.23(d, J=8 Hz, 2H).

IR ν (CHCl$_3$) cm$^{-1}$: 1700, 1599.

Step 3. Preparation of a phthalimido compound

A mixture of (2S,4R)-1-p-nitrobenzyloxycarbonyl-4-methanesulfonyloxypyrrolidine-2-methanol p-toluenesulfonate (25 g: 47.3 mmole) and potassium phthalimide (17.52 g: 2 eq.) in dimethylformamide (250 ml) is stirred at 60° C. for 7 hours. The reaction mixture is poured into ice water and filtrated. The resulting precipitate is dissolved in ethyl acetate, washed with saturated brine, dried over magnesium sulfate, and concentrated in vacuo. The residue is recrystallized from methanol to give (2S,4R)-1-p-nitrobenzyloxycarbonyl-2-phthalimidomethyl-4-methanesulfonyloxypyrrolidine (18.76 g). Yield: 79%. mp. 121° to 123° C.

NMR δ (CDCl$_3$) ppm: 2.03 to 2.60(m, 2H), 3.02(s, 3H), 3.50 to 4.15(m, 4H), 4.40 to 4.63(m, 1H), 5.10, 5.29(ABq, J=15 Hz, 2H), 5.10 to 5.30(m, 1H), 7.46 (d, J=9 Hz, 1H), 7.57(d, J=9 Hz, 1H), 7.63 to 7.88(m, 4H), 8.20(d, J=9 Hz, 2H)

IR ν (CHCl$_3$) cm$^{-1}$: 1773, 1715, 1605.

Step 4. Preparation of an acetylthio compound

A solution of (2S,4R)-1-p-nitrobenzyloxycarbonyl-2-phthalimidomethyl-4-methanesulfonyloxypyrrolidine (10 g: 19.88 mmole) and potassium thioacetate (4.54 g: 2 eq.) in dimethylformamide (60 ml) is stirred at 60° C. for 3 hours. The reaction mixture is poured into ice water (200 ml) and filtered. The precipitate is dissolved in ethyl acetate, dried over magnesium sulfate, and concentrated in vacuo. The residue is purified by silica gel column chromatography (toluene: ethyl acetate) to give (2S,4S)-1-p-nitrobenzyloxycarbonyl-2-phthalimidomethyl-4-acetylthiopyrrolidine (8.7 g). Yield: 90%.

NMR δ (CDCl$_3$) ppm: 1.65 to 1.97(m, 1H), 2.47 to 2.67(m, 1H), 3.24 to 3.34(q, 1H), 3.73 to 4.24(m, 4H), 4.30 to 4.54(m, 1H), 5.02(dd, J=14 Hz, J=7 Hz, 1H), 5.20(d, J=14 Hz, 1H), 7.42(d, J=9 Hz, 1H), 7.45(d, J=9 Hz, 1H), 7.60 to 8.86(m, 4H), 8.17(d, J=9 Hz, 2H).

IR ν (CHCl$_3$) cm$^{-1}$: 1773, 1714, 1605.

Step 5. Removal of a phthalyl and an acetyl groups

To a solution of (2S,4S)-1-p-nitrobenzyloxycarbonyl-2-phthalimidomethyl-4-acetylthiopyrrolidine (4.92 g: 10.18 mmole) in a mixture of dichloromethane (15 ml) and methanol (75 ml), hydrazine hydrate (1.53 ml: 3 eq.) is added. The mixture is warmed to remove dichloromethane and heated to reflux for 1 hour and 10 minutes. The reaction mixture is concentrated in vacuo. The residue is diluted with dichloromethane and filtered. The filtrate is washed with water, dried over magnesium sulfate, and concentrated in vacuo to give crude (2S,4S)-1-p-nitrobenzyloxycarbonyl-2-aminomethyl-4-mercaptopyrrolidine (3.3 g). Yield: Quantitative.

NMR δ (CDCl$_3$) ppm: 1.63 to 1.90(m, 1H), 2.48 to 2.68(m, 1H), 2.86 to 3.43(m, 4H), 3.65 to 4.23(m, 2H), 5.22(s, 2H), 7.52(d, J=9 Hz, 2H), 8.23 (d, J=9 Hz, 2H).

Step 6. Preparation of an N-sulfamoyl compound

To a solution of crude (2S,4S)-1-p-nitrobenzyloxycarbonyl-2-aminomethyl-4-mercaptopyrrolidine (3.3 g: 10.18 mmole) in dichloromethane (100 ml) at −78° C., triethylamine (2.84 ml: 2.2 eq.) and trimethylchlorosilane (3.12 ml: 2.2 eq.) are dropwise added. After stirring for 20 minutes, triethylamine (4.25 ml: 3 eq.) and 1M-sulfamoyl chloride in dichloromethane (25 ml: 2.5 eq.) are dropwise added to the mixture. After 20 minutes stirring, the reaction mixture is acidified with hydrochloric acid, warmed to room temperature, and extracted with dichloromethane. The extract is washed with water, and 1N-hydrochloric acid (10 ml) and methanol (30 ml) are added thereto. The solution is stirred at room temperature for 30 minutes. The reaction mixture is washed with water, dried over magnesium sulfate, and concentrated in vacuo. The residue is purified by silica gel column chromatography (toluene: ethyl acetate) to give (2S,4S)-1-p-nitrobenzyloxycarbonyl-2-sulfamoylaminomethyl-4-mercaptopyrrolidine (2.65 g). Yield: 66.7%.

NMR δ (CDCl$_3$-CD$_3$OD) ppm: 1.42(t, J=7 Hz, 1H), 1.65 to 1.93(m, 1H), 2.48 to 2.70(m, 1H), 3.05 to 3.63(m, 4H), 3.93 to 4.16(m, 2H), 5.22(s, 2H), 7.53(d, J=8 Hz, 2H), 8.23(d, J=8 Hz, 2H).

IR ν (CHCl$_3$) cm$^{-1}$: 3276 br, 1692, 1607.

PREPARATIVE EXAMPLE 4 OF A PYRROLIDINE DERIVATIVE

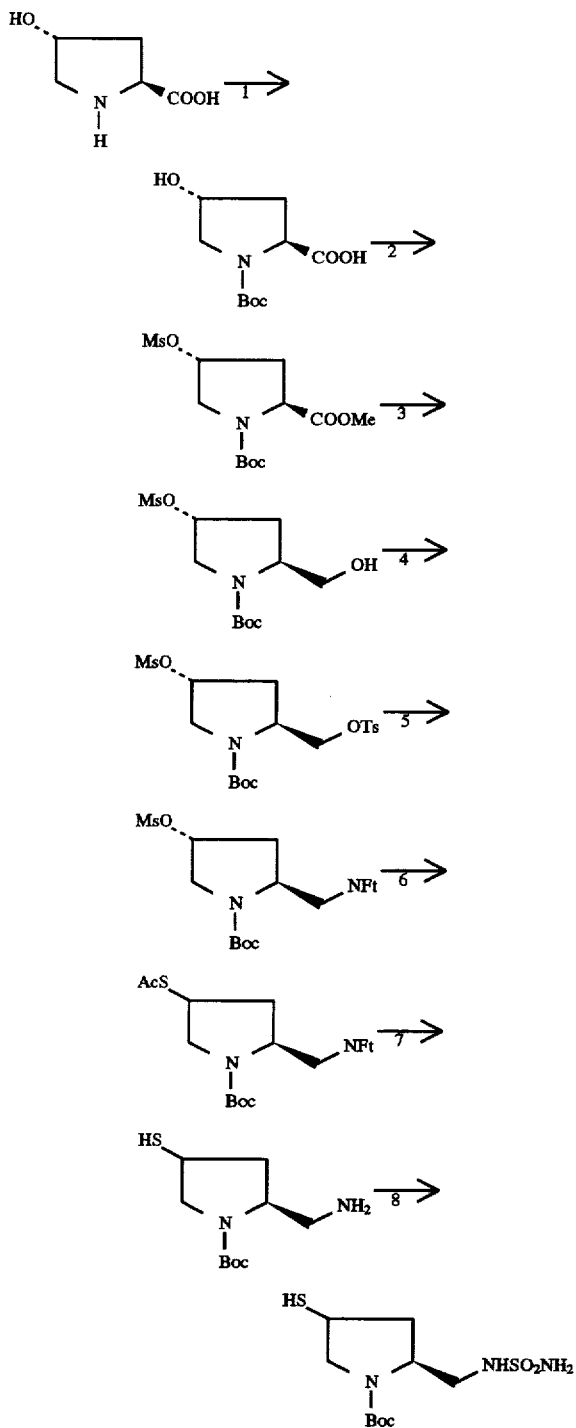

Step 1. Preparation of a Boc compound

To a suspension of trans-4-hydroxy-L-proline (50 g) in a mixture of water (300 ml) and t-butanol (100 ml) are added aqueous sodium hydrogen carbonate (32.3 g), di-t-butyl dicarbonate (104 g) and dioxane (200 ml). The mixture is stirred at room temperature overnight. The organic solvent is removed and the resulting aqueous solution is layered with methyl ethyl ketone and ethyl acetate, and acidified with conc. hydrochloric acid (34.5 ml) under ice cooling. The organic layer is taken, washed with saturated brine, dried over sodium sulfate, and concentrated in vacuo. The residue is recrystallized from ethyl acetate-toluene to give trans-1-t-butoxycarbonyl-4-hydroxy-L-proline (82.9 g). Colorless crystals. Yield: 94%. mp. 126° to 128° C.

NMR δ (CDCl$_3$) ppm: 1.43, 1.46(2×s, 9H), 1.95 to 2.36(m, 2H), 3.36 to 3.6(m, 2H), 4.23 to 4.44(m, 2H).

IR ν (CHCl$_3$) cm$^{-1}$: 3360, 1735, 1656.

Elemental analysis (C$_{10}$H$_{17}$NO$_5$) Calcd.: C, 51.94; H, 7.41; N, 6.06. Found: C, 51.65; H, 7.38; N, 5.99.

Step 2. Preparation of a compound having mesyloxy and methoxycarbonyl groups

To a solution of trans-1-t-butoxycarbonyl-4-hydroxy-L-proline (8.5 g) in tetrahydrofuran (110 ml) at −30° C., triethylamine (12.8 ml) and methanesulfonyl chloride (6.27 ml) are added. The mixture is stirred at the same temperature for 30 minutes. To the mixture triethylamine (5.13 ml) and methanol (30 ml) are added. The mixture is stirred for 30 minutes. The reaction mixture is acidified with 1N-hydrochloric acid (37 ml) and extracted with ethyl acetate. The extract is successively washed with water, aqueous sodium hydrogen carbonate, water and saturated brine, dried over sodium sulfate, and concentrated in vacuo. The residue is purified by silica gel column chromatography and recrystallized from toluene-petroleum ether to give (2S,4R)-1-t-butoxycarbonyl-4-methanesulfonyloxypyrrolidine-2-carboxylic acid methyl ester (9.16 g). Colorless crystals. Yield: 77%. mp. 86° to 87° C.

NMR δ (CDCl$_3$) ppm: 1.42, 1.47, 1.50(3×s, 9H), 2.19 to 2.35(m, 1H), 2.48 to 2.75(m, 1H), 3.06, 3.07, 3.26(3×s, 3H), 3.59 to 4.12(m, 5H), 4.35 to 4.60(m, 1H), 5.18 to 5.32(m, 1H).

IR ν (CHCl$_3$) cm$^{-1}$: 1748, 1698.

Step 3. Preparation of a methylol compound

To a solution of (2S,4R)-1-t-butoxycarbonyl-4-methanesulfonyloxypyrrolidine-2-carboxylic acid methyl ester (8.11 g) in tetrahydrofuran (49 ml) stirring under ice cooling, sodium borohydride (2.36 g) and methanol (20 ml) are added. The mixture is stirred at room temperature for 25 minutes and at 60° C. for 25 minutes. The mixture is cooled with ice and filtered. The filtrate is concentrated, diluted with ethyl acetate, washed with water, dried over sodium sulfate, and concentrated in vacuo. The residue is recrystallized from petroleum ether-ether to give (2S, 4R)-1-t-butoxycarbonyl-4-methanesulfonyloxypyrrolidine-2-methanol (5.96 g). Colorless crystals. Yield: 80%. mp. 95° to 96° C.

NMR δ (CDCl$_3$) ppm: 1.48(s, 9H), 1.78 to 2.02(m, 1H), 2.3 to 2.48(m, 1H), 3.05(s, 3H), 3.5 to 3.65(m, 2H), 3.65 to 4.0(m, 2H), 4.03 to 4.25(m, 1H), 5.2(s, 1H).

IR ν (CHCl$_3$) cm$^{-1}$: 3460, 1680.

Step 4. Preparation of a tosyl compound

To a solution of (2S,4R)-1-t-butoxycarbonyl-4-methanesulfonyloxypyrrolidine-2-methanol (12.0 g) in dichloromethane (180 ml) stirring under ice cooling, triethylamine (6.23 ml), p-toluenesulfonyl chloride (8.52 g) and N,N-dimethylaminopyridine (993 mg) are successively added. The mixture is heated to reflux for 3 hours, supplemented with triethylamine (0.57 ml) and p-toluenesulfonyl chloride (775 mg), and heated to reflux for 1 hour. The reaction mixture is acidified with dilute hydrochloric acid. The organic layer is taken, washed with water, dried over sodium sulfate and concentrated in vacuo. The residue is purified by silica gel column chromatography and recrystallized from n-hexane to give (2S,4R)-1-t-butoxycarbonyl-4-methanesulfonyloxypyrrolidine-2-methanol p-toluenesulfonate (16.8 g). Yield: 92%. mp. 65° to 66° C.

NMR δ (CDCl$_3$) ppm: 1.42(s, 9H), 2.15 to 2.55(m, 2H), 2.45(s, 3H), 3.03(s, 3H), 3.3 to 4.5(m, 5H), 5.1 to 5.25(m, 1H), 7.35(d, J=8.0 Hz, 2H), 7.76(d, J=8.0 Hz, 2H).

IR ν (CHCl₃) cm⁻¹: 1693.

Step 5. Preparation of a phthalimido compound

To a solution of (2S,4R)-1-t-butoxycarbonyl-4-methanesulfonyloxypyrrolidine-2-methanol p-toluenesulfonate (20.78 g) in dimethylformamide(200 ml), potassium phthalimide (9.61 g) is added. The mixture is stirred at 70° C. for 3 hours. The reaction mixture is poured into a mixture of water and ethyl acetate. The organic layer is taken, successively washed withsodium sulfate, and co hydroxide and water, dried over sodium sulfate, and concentrated in vacuo. The residue is purified by 5% wet silica gel column chromatography to give (2S,4R)-1-t-butoxycarbonyl-2-phthalimidomethyl-4-methanesulfonyloxypyrrolidine (11.17 g). Yield: 60%. Colorless foam.

NMR δ (CDCl₃) ppm: 1.33, 1.42(2×s, 9H), 2.0 to 2.55(m, 2H), 3.02(s, 3H), 3.4 to 4.6(m, 5H), 5.15 to 5.3(m, 1H), 7.6 to 7.95(m, 4H).

IR ν (CHCl₃) cm⁻¹: 1775, 1716, 1693.

Step 6. Preparation of an acetylthio compound

To a solution of (2S,4R)-1-t-butoxycarbonyl-2-phthalimidomethyl-4-methanesulfonyloxypyrrolidine (3 g) in dimethylformamide (30 ml), potassium thioacetate (1.65 g) is added. The mixture is stirred at 60° C. for 3.5 hours. The reaction mixture is poured into a mixture of ethyl acetate and dilute hydrochloric acid. The organic layer is taken, washed with water, dried over sodium sulfate, and concentrated in vacuo. The residue is purified by silica gel column chromatography to give (2S,4S)-1-t-butoxycarbonyl-2-phthalimidomethyl-4-acetylthiopyrrolidine (2.12 g). Yield: 74%. Orange colored syrup.

NMR δ (CDCl₃) ppm: 1.30, 1.39(2×s, 9H), 1.6 to 2.0(m, 1H), 2.34(s, 3H), 2.4 to 2.67(m, 1H), 3.15 to 3.3(m, 1H), 3.65 to 4.55(m, 5H), 7.6 to 8.0(m, 4H).

IR ν (CHCl₃) cm⁻¹: 1774, 1715, 1688.

Step 7. Removal of a phthalyl and an acetyl groups

To a solution of (2S,4S)-1-t-butoxycarbonyl-2-phthalimidomethyl-4-acetylthiopyrrolidine (8.58 g) in a mixture of dichloromethane (26 ml) and methanol (129 ml), hydrazine hydrate (4.11 ml) is added. The mixture is heated to reflux for 2 hours and 45 minutes and filtered. The filtrate is concentrated in vacuo. The residue is dissolved in dichloromethane, washed with water, dried over sodium sulfate, and concentrated in vacuo to give crude (2S,4S)-1-t-butoxycarbonyl-2-aminomethyl-4-mercaptopyrrolidine (4.1 g). Yellow syrup.

Step 8 Preparation of a sulfamoyl compound

To a solution of crude (2S,4S)-1-t-butoxycarbonyl-2-aminomethyl-4-mercaptopyrrolidine (4.1 g) in dichloromethane (250 ml) at −70° C. under a stream of nitrogen, triethylamine (8.87 ml) and trimethylchlorosilane (6.73 ml) are added. The mixture is stirred for 1 hour and 40 minutes, mixed with triethylamine (8.87 ml) and a solution of 1M-sulfamoyl chloride in dichloromethane (64 ml), and stirred for 1 hour. The reaction mixture is acidified with dilute hydrochloric acid. The organic layer is taken, diluted with 1N-hydrochloric acid (21 ml) and methanol (50 ml), stirred for 35 minutes at room temperature, and poured into water. The organic layer is taken, washed with water, dried over magnesium sulfate, and concentrated in vacuo. The residue is purified by silica gel column chromatography to give (2S,4S)-1-t-butoxycarbonyl-2-sulfamoylaminomethyl-4-mercaptopyrrolidine (4.57 g). Yield: 69%. Colorless syrup.

NMR δ (CDCl₃) ppm: 1.46(s, 9H), 1.5 to 1.8(m, 1H), 1.71(d, J=6.6 Hz, 1H), 2.5 to 2.67(m, 1H), 3.0 to 3.46(m, 4H), 3.85 to 4.2(m, 2H), 4.6 (br s, 2H).

IR ν (CHCl₃) cm⁻¹: 3420, 3340, 3270, 1679.

PREPARATIVE EXAMPLE 5 OF A PYRROLIDINE DERIVATIVE

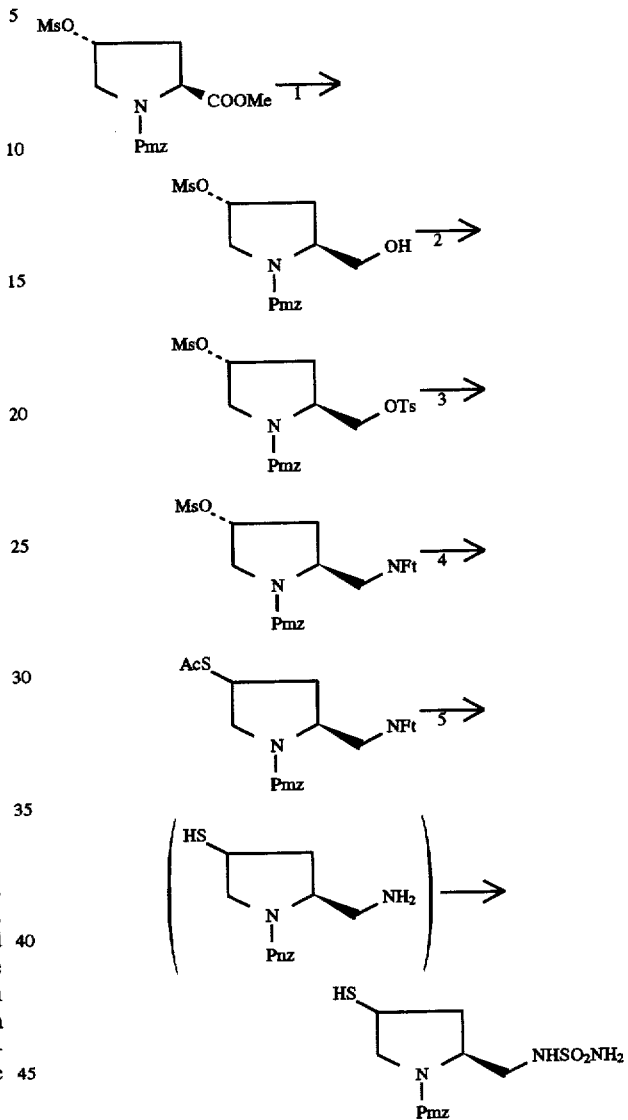

Step 1. Preparation of a methylol compound

To a solution of (2S,4R)-1-p-methoxybenzyloxycarbonyl-4-methanesulfonyloxypyrrolidine-2-carboxylic acid methyl ester (79.4 g: 205 mmole) in a mixture of tetrahydrofuran (200 ml) and ethanol (300 ml), sodium borohydride (14 g) is added in several portions under ice cooling. The mixture is stirred at room temperature for 4 hours. The reaction mixture is neutralized with conc. sulfuric acid, concentrated in vacuo to approximately a half volume, diluted with water, and extracted with ethyl acetate. The extract is successively washed with aqueous sodium hydrogen carbonate, water and brine, dried over magnesium sulfate, and concentrated in vacuo. The residue is purified by silica gel column chromatography (toluene: ethyl acetate=1:2) to give (2S,4R)-1-p-methoxybenzyloxycarbonyl-4-methanesulfonyloxypyrrolidine-2-methanol (58.7 g). Yield: 81.7%.

NMR δ (CDCl₃) ppm: 1.8 to 2.2(m, 1H), 2.3 to 2.5(m, 1H), 3.01(s, 3H), 3.57 (d, J=4.4 Hz, 1H), 3.64(d, J=4.4 Hz, 1H), 3.81(s, 3H), 3.82 to 4.3(m,3H), 5.09(s, 2H), 5.21(br s, 1H), 6.89(d, J=8.8 Hz, 2H), 7.31(d, J=8.8 Hz,2H).

Step 2. Preparation of a tosyl compound

To a solution of (2S,4R)-1-p-methoxybenzyloxycarbonyl-4-methanesulfonyloxypyrrolidine-2-methanol (8.7 g: 24.2 mmole) in dichloromethane(80 ml) are added triethylamine (4.05 ml), p-toluenesulfonyl chloride (5.08 g) and 4-dimethylaminopyridine (148 mg). The mixture is stirred at room temperature overnight. The reaction mixture is washed with water and brine, dried over magnesium sulfate, and concentrated in vacuo. The residue is purified by silica gel column chromatography (toluene: ethyl acetate=1:1) to give (2S,4R)-1-p-methoxybenzyloxycarbonyl-4-methanesulfonyloxypyrrolidine-2-methanol p-toluenesulfonate (11.75 g). Yield: 95%.

NMR δ (CDCl$_3$) ppm: 2.2 to 2.5(m), 2.44(s, 3H), 2.98(s, 3H), 3.4 to 3.6(m, 2H), 3.82(s, 3H), 3.8 to 4.6(m), 5.03, 4.95(ABq, J=12 Hz, 2H), 5.2 (br s, 1H), 6.89(d, J=8.6 Hz, 2H), 7.18 to 7.4(m, 4H), 7.6 to 7.8(m, 2H).

IR ν (CHCl$_3$) cm$^{-1}$: 1698, 1612.

Step 3. Preparation of a phthalimido compound

To a solution of (2S,4R)-1-p-methoxybenzyloxycarbonyl-4-methanesulfonyloxypyrrolidine-2-methanol p-toluenesulfonate (6.35 g: 12.27 mmole) in dimethylformamide (60 ml), potassium phthalimide (2.7 g) is added. The mixture is stirred at 70° C. for 4 hours. The reaction mixture is poured into ice water and extracted with ethyl acetate. The extract is successively washed with water and brine, dried over magnesium sulfate, and concentrated in vacuo. The residue is purified by silica gel column chromatography (toluene: ethyl acetate=2:1) to give (2S,4R)-1-p-methoxybenzyloxycarbonyl-4-methanesulfonyloxy-2-phthalimidomethylpyrrolidine (4.65 g). Yield: 77.5%.

NMR δ (CDCl$_3$) ppm: 2 to 2.3(m, 1H), 2.4 to 2.6(m, 1H), 2.95, 2.97(2×s,3H), 3.43 to 4.2(m, 5H), 3.80(s, 3H), [5.01 (s)+5.07, 4.96(ABq, 12.2 Hz), 2H], 5.13 to 5.3(m, 1H).

IR ν (CHCl$_3$) cm$^{-1}$: 1774, 1716, 1613.

Step 4. Preparation of an acetylthio compound

To a solution of (2S,4R)-1-p-methoxybenzyloxycarbonyl-4-methanesulfonyloxy-2-phthalimidopyrrolidine (4.0 g: 8.19 mmole) in dimethylformamide (40 ml), potassium thioacetate (2.1 g) is added. The mixture is stirred at 60° C. for 3 hours. The reaction mixture is diluted with ethyl acetate, successively washed with water and brine, dried over magnesium sulfate, and concentrated in vacuo. The residue is purified by silica gel column chromatography (toluene: ethyl acetate=2:1) to give (2S,4S)-1-p-methoxybenzyloxycarbonyl-4-acetylthio-2-phthalimidomethylpyrrolidine (3.2 g). Yield: 78%.

NMR δ (CDCl$_3$) ppm: 1.7 to 1.9(m, 1H), 2.4 to 2.7(m, 1H), 3.21, 3.26(2×d, J=7 Hz, 2H), 3.8(s, 3H), 3.7 to 4.2(m), 4.2 to 4.5(m, 1H), [4.95(s) +5.04, 4.83(ABq, J=12 Hz), 2H], 6.83(d, J=7.6 Hz, 2H), 7.18 to 7.3(m, 2H), 7.6 to 7.9(m, 4H).

IR ν (CHCl$_3$) cm$^{-1}$: 1773, 1714.

Step 5. Removal of an acetyl and a phthalyl groups and introduction of a sulfamoyl group To a solution of (2S,4S)-1-p-methoxybenzyloxycarbonyl-4-acetylthio-2-phthalimidomethylpyrrolidine (4.3 g: 9.18 mmole) in a mixture of dichloromethane (13 ml) and methanol (65 ml), hyrazine hydrate (1.78 ml) is added. The mixture is heated to reflux for 4 hours. The reaction mixture is concentrated in vacuo. The residue is dissolved in dichloromethane and filtered under a stream of nitrogen to remove solid. The filtrate is washed with water, dried over magnesium sulfate, and concentrated in vacuo. The resulting residue containing (2S,4S)-1-p-methoxybenzyloxycarbonyl-4-mercapto-2-aminomethylpyrrolidine is diluted with dichloromethane (100 ml), added triethylamine (2.63 g) and trimethylchlorosilane (2.4 ml) at −78° C., and stirred for 20 minutes. To the reaction mixture, triethylamine (2.63 ml) and a solution (16.5 ml) of 1M-sulfamoyl chloride in dichloromethane are added. The mixture is stirred for 20 minutes. The reaction mixture is washed with dilute hydrochloric acid, mixed with 1N-hydrochloric acid (9 ml) and methanol (20 ml), and stirred at room temperature for 30 minutes. The reaction mixture is successively washed with water and brine, dried over magnesium sulfate, and concentrated in vacuo. The residue is purified by silica gel column chromatography (toluene: ethyl acetate=1:2) to give (2S,4S)-1-p-methoxybenzyloxycarbonyl-4-mercapto-2-sulfamoylaminomethylpyrrolidine (2.71 g). Yield:78.6%.

NMR δ (CDCl$_3$) ppm: 1.6 to 2.0(m, 2H), 2.4 to 2.7(m, 1H), 3.1 to 3.8(m,4H), 3.81(s, 3H), 3.9 to 4.2(m, 2H), 4.6 to 5.0(m, 2H), 5.04(s, 2H), 5.97(br s, 1H), 6.89(d, J=8.6 Hz, 2H), 7.30(d, J=8.6 Hz, 2H).

IR ν (CHCl$_3$) cm$^{-1}$: 3668, 3424, 1683.

PREPARATIVE EXAMPLE 6 OF A PYRROLIDINE DERIVATIVE

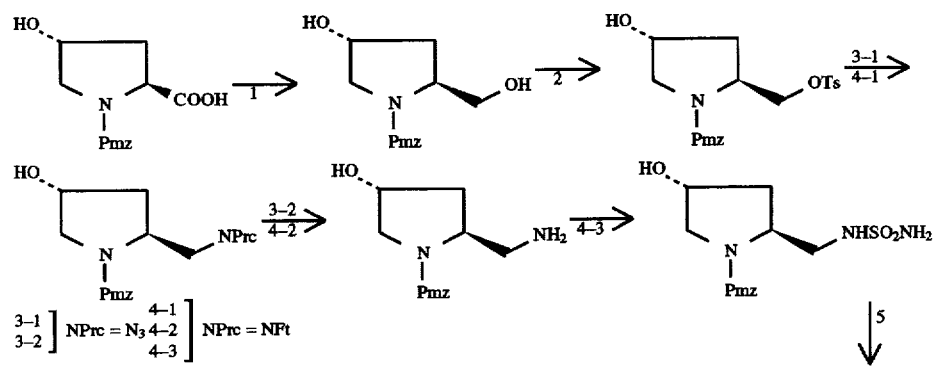

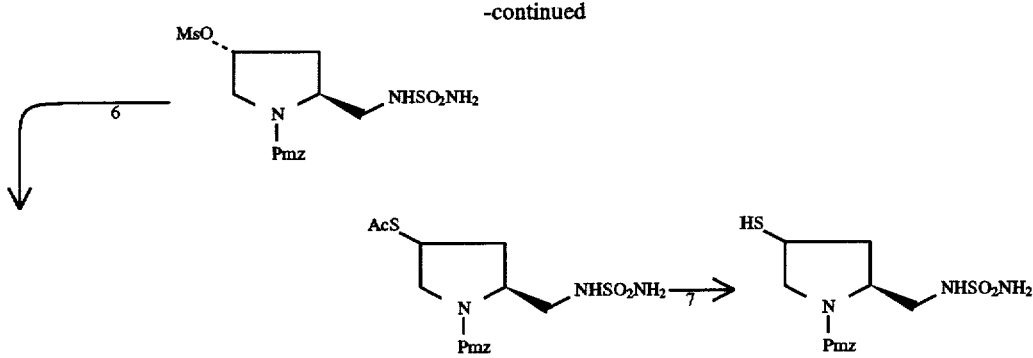

Step 1. Preparation of a methylol compound

To a solution of trans-1-p-methoxybenzyloxycarbonyl-4-hydroxyproline (105.5 g: 357.5 mmole) in tetrahydrofuran (1 liter), triethylamine (54.8 ml) is added. After adding ethyl chloroformate (35.9 ml) dropwise at −30° C., the mixture is stirred for 20 minutes. To the reaction mixture, a solution of sodium borohydride (33.25 g) in water (120 ml) is added dropwise at a temperature in the range of −15° to −5° C., neutralized with conc. hydrochloric acid, and concentrated in vacuo. To the residue, ethyl acetate is added, washed with brine, dried over magnesium sulfate, and concentrated in vacuo to give (2S,4R)-1-p-methoxybenzyloxycarbonyl-4-hydroxy-pyrrolidine-2-methanol.

NMR δ (CDCl$_3$) ppm: 1.6 to 1.8(m, 1H), 1.95 to 2.2(m, 1H), 3.4 to 3.8 (m, 4H), 3.8(s, 3H), 4.0 to 4.3(m, 1H), 4.37(br s, 1H), 5.07(s, 2H), 6.88(d, J=8.8 Hz, 2H), 7.30(d, J=8.8 Hz, 2H).

Step 2. Preparation of a tosyl compound

To a solution of (2S,4R)-1-p-methoxybenzyloxycarbonyl-4-hydroxypyrrolidine-2-methanol (64 g: 227.6 mmole) in pyridine (350 ml), p-toluenesulfonyl chloride (48 g) is added. The mixture is stirred at room temperature for 4 hours. The reaction mixture is poured into ice water and extracted with ethyl acetate. The extract is successively washed with water, dilute hydrochloric acid and aqueous sodium hydrogen carbonate, dried over magnesium sulfate, and concentrated in vacuo. The residue is purified by silica gel column chromatography to give (2S,4R)-1-p-methoxybenzyloxycarbonyl-4-hydroxypyrrolidine-2-methanol p-toluenesulfonate (60 g).

NMR δ (CDCl$_3$) ppm: 2.0 to 2.4(m, 2H), 2.44(s, 3H), 3.3 to 3.7(m, 2H), 3.82(s, 3H), 3.9 to 4.6(m, 4H), 4.8 to 5.1(m, 2H), 6.88(d, J=8.6 Hz, 2H),7.2 to 7.4(m, 4H), 7.6 to 7.8(m, 2H).

IR ν (CHCl$_3$) cm$^{-1}$: 3446, 1693.

Step 3. Preparation of an amino precursor (—NProc=azido)

1) To a solution of (2S,4R)-1-p-methoxybenzyloxycarbonyl-4-hydroxypyrrolidine-2-methanol p-toluenesulfonate (8.7 g: 20 mmole) in dimethylformamide (60 ml), a solution of sodium azide (1.56 g) in water (6 ml) is added. The mixture is stirred at 80° C. overnight. The reaction mixture is poured into ice water and extracted with ethyl acetate. The extract is successively washed with water and brine, dried over magnesium sulfate, and concentrated in vacuo to give crude (2S,4R)-1-p-methoxybenzyloxycarbonyl-4-hydroxy-2-azidomethylpyrrolidine (5.6 g). Yield: 92%.

NMR δ (CDCl$_3$) ppm: 1.95 to 2.1(m, 2H), 3.2 to 3.8(m, 3H), 3.81(s, 3H),3.83 to 4.6(m, 3H), 5.07(s, 2H), 6.89(d, J=8.8 Hz, 2H), 7.31(d, J=8.8 Hz, 2H).

IR ν (CHCl$_3$) cm$^{-1}$: 3420, 2100, 1689.

2) To a solution of the thus obtained (2S,4R)-1-p-methoxybenzyloxycarbonyl-4-hydroxy-2-azidomethylpyrrolidine (5.57 g: 18.18 mmole) in methanol (30 ml) are added, 5% palladium on charcoal (560 mg) and ammonium formate (2.3 g). The mixture is stirred at 45° C. for 2 hours. The reaction mixture is diluted with dichloromethane (50 ml), filtered to remove the catalyst, and concentrated in vacuo. The residue is crystallized from a mixture of dichloromethane and ether and washed with ether to give (2S,4R)-1-p-methoxybenzyloxycarbonyl-4-hydroxy-2-aminomethylpyrrolidine formate (4.28 g). Yield: 72%.

NMR δ (CDCl$_3$-CD$_3$OD) ppm: 1.6 to 1.82(m, 1H), 2.1 to 2.3(m, 1H), 2.7 to 3.7(m, 4H), 3.81(s, 3H), 4.1 to 4.4(m, 2H), 5.04(s, 2H), 6.88(d, J=8.8 Hz, 2H), 7.28(d, J=8.8 Hz, 2H), 8.47(s, 1H).

IR ν (CHCl$_3$) cm$^{-1}$: 3678, 3412, 1678, 1602.

Step 4. Introduction of a protected amino group, removal of the protection, and introduction of a sulfamoyl group (—NProc=phthalimido)

1) To a solution of (2S,4R)-1-p-methoxybenzyloxycarbonyl-4-hydroxypyrrolidine-2-methanol p-toluenesulfonate (24 g: 55.1 mmole) in dimethylformamide (200 ml), potassium phthalimide (15.3 g) is added. The mixture is stirred at 80° C. for 4 hours. The reaction mixture is diluted with ethyl acetate, successively washed with water and brine, dried over magnesium sulfate, and concentrated in vacuo. The residue is purified by silica gel column chromatography (toluene: ethyl acetate=1:2) to give (2S,4R)-1-p-methoxybenzyloxycarbonyl-4-hydroxy-2-phthalimidomethylpyrrolidine (18.1 g). Yield: 80%.

NMR δ (CDCl$_3$) ppm: 1.9 to 2.2(m, 2H), 3.4 to 4.05(m, 5H), 3.80(s, 3H), 4.3 to 4.6(m, 2H), 4.8 to 5.1(m, 2H), 6.83(d, J=8.2 Hz, 2H), 7.25(d, J=8.2 Hz, 2H), 7.6 to 7.9(m, 4H).

IR ν (CHCl$_3$) cm$^{-1}$: 3458, 1773, 1712.

2) To a solution of (2S,4R)-1-p-methoxybenzyloxycarbonyl-4-hydroxy-2-phthalimidomethylpyrrolidine (5.13 g: 12.5 mmole) in a mixture of dichloromethane (15 ml) and methanol (50 ml), hydrazine hydrate (1.0 ml) is added. The mixture is heated to reflux for 2 hours and concentrated in vacuo. The residue is diluted with dichloromethane, filtered to remove solid, washed with brine, dried over magnesium sulfate, and concentrated in vacuo to give a residue containing (2S,4R)-1-p-methoxybenzyloxycarbonyl-4-hydroxy-2-aminomethylpyrrolidine as a main component.

3) To a solution of the above-mentioned residue in dichloromethane (70 ml) at −70° C., triethylamine (4.6 ml) and trimethylchlorosilane (3.7 ml) are added. The mixture is stirred for 20 minutes. To the reaction mixture, triethylamine (5.5 ml) and a solution of 1M-sulfamoyl chloride in dichloromethane (34 ml) are added. The mixture is stirred for 15 minutes. The reaction mixture is washed with dilute hydrochloric acid, mixed with methanol (50 ml), and then 4N-hydrochloric acid (3.3 ml) is added under ice cooling. After stirring the mixture, aqueous sodium hydrogen carbonate is added. The organic layer is taken, washed with water and brine, dried over magnesium sulfate, and concentrated in vacuo to give crude (2S,4R)-1-p-methoxybenzyloxycarbonyl-4-hydroxy-2-sulfamoylaminomethylpyrrolidine (3.96 g).

NMR δ (CDCl₃) ppm: 1.8 to 2.25(m, 2H), 3 to 4.5(m, 7H), 3.79(s, 3H), 5.03(s, 2H), 5.2 to 5.8(m, 2H), 6.08(br s, 1H), 6.87(d, J=8.8 Hz, 2H), 7.29(d, J=8.8 Hz, 2H).

IR ν (CHCl₃) cm⁻¹: 3456, 1689.

Step 5 Preparation of a mesyl compound

To a solution of crude (2S,4R)-1-p-methoxybenzyloxycarbonyl-4-hydroxy-2-sulfamoylaminomethylpyrrolidine (1.8 g: 5 mmole) obtained in Step 4 in dichloromethane (20 ml) at −70° C., triethylamine (0.77 ml) and methanesulfonyl chloride (0.39 ml) are added. The mixture is stirred for 45 minutes. The reaction mixture is neutralized with dilute hydrochloric acid, successively washed with water and brine, and concentrated in vacuo to give crude (2S,4R)-1-p-methoxybenzyloxycarbonyl-4-methanesulfonyloxy-2-sulfamoylaminomethylpyrrolidine (2.26 g).

NMR δ (CDCl₃) ppm: 2 to 2.5(m, 2H), 2.99(s, 3H), 3.0 to 4.3(m, 5H), 3.79(s, 3H), 4.8 to 5.3(m, 3H), 5.05(s, 2H), 5.7 to 5.85(m, 1H), 6.88(d,J=8.8 Hz, 2H), 7.29(d, J=8.8 Hz, 2H).

IR ν (CHCl₃) cm⁻¹: 3606, 3416, 1690.

Step 6. Preparation of an acetylthio compound

To a solution of crude (2S,4R)-1-p-methoxybenzyloxycarbonyl-4-methanesulfonyloxy-2-sulfamoylaminomethylpyrrolidine (2.26 g) obtained in Step 5 in dimethylformamide (12 ml), potassium thioacetate (1.7 g) is added. The mixture is stirred at 60° C. for 5 hours. The reaction mixture is diluted with ethyl acetate, successively washed with water and brine, dried over magnesium sulfate, and concentrated in vacuo. The residue is purified by silica gel column chromatography (toluene: ethyl acetate=1:2) to give (2S,4S)-1-p-methoxybenzyloxycarbonyl-4-acetylthio-2-sulfamoylaminomethylpyrrolidine (971 mg).

NMR δ (CDCl₃) ppm: 1.8(br s, 1H), 2.33(s, 3H), 2.4 to 2.7(m, 1H), 3.1 to 3.5(m), 3.81(s, 3H), 3.9 to 4.2(m, 2H), 5.05(s, 2H), 6.89(d, J=8.8 Hz, 2H), 7.30(d, J=8.8 Hz, 2H).

IR ν (CHCl₃) cm⁻¹: 3414, 3276, 1688.

Step 7. Removal of an acetyl group

To a solution of (2S,4S)-1-p-methoxybenzyloxycarbonyl-4-acetylthio-2-sulfamoylaminomethylpyrrolidine (982 mg: 2.35 mmole) in a mixture of dichloromethane (2 ml) and methanol (10 ml), 1N-sodium hydroxide (2.8 ml) is added under ice cooling. The mixture is stirred for 15 minutes. The reaction mixture is diluted with water and extracted with ethyl acetate. The extract is successively washed with water and brine, dried over magnesium sulfate, and concentrated in vacuo. The residue is purified by silica gel column chromatography (toluene: ethyl acetate=1:2) to give (2S,4S)-1-p-methoxybenzyloxycarbonyl-4-mercapto-2-sulfamoylaminomethylpyrrolidine (783 mg). Yield: 89%.

NMR δ (CDCl₃) ppm: 1.6 to 2.0(m, 2H), 2.4 to 2.7(m, 1H), 3.1 to 3.8(m, 4H), 3.81(s, 3H), 3.9 to 4.2(m, 2H), 4.6 to 5.0(m, 2H), 5.04(s, 2H), 5.97(br s, 1H), 6.89(d, J=8.6 Hz, 2H), 7.30(d, J=8.6 Hz.

IR ν (CHCl₃) cm⁻¹: 3668, 3424, 1683.

PREPARATIVE EXAMPLE 7-A OF A PYRROLIDINE DERIVATIVE

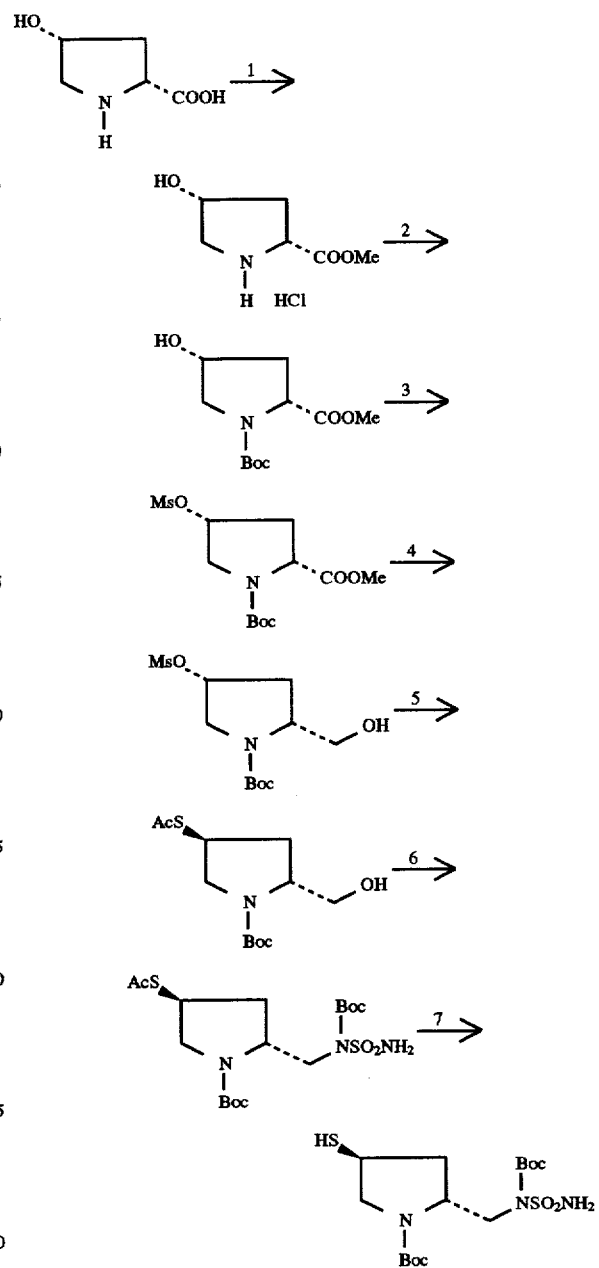

Step A-1. Preparation of an ester compound

To a suspension of cis-4-hydroxy-D-proline (16.46 g: 125.5 mmole) in methanol (66 ml), thionylchloride (9.16 ml: 125.5 mmole) is added in a nitrogen atmosphere under ice cooling, and the mixture is stirred at room temperature for 30 minutes. The mixture is further stirred to react at 40° C. for 4 hours to give (2R,4R)-4-hydroxy-2-methoxycarbonylpyrrolidine hydrochloride as crude crystals (25.74 g). Yield: 113%. Colorless crystals.

NMR δ (D₂O) ppm: 2.3 to 2.6(m, 2H), 3.33(s, 1H), 3.4 to 3.5(m, 2H), 3.84(s, 3H), 4.6 to 4.7(m, 2H).

IR ν (KBr) cm⁻¹: 3320, 2980, 1728.

Step A-2. Preparation of a Boc compound

To a suspension of (2R,4R)-4-hydroxy-2-methoxycarbonylpyrrolidine hydrochloride (25.64 g: 125 mmole) in dichloromethane (125ml), triethylamine (19.11 ml: 137.5 mmole) is added dropwise in a nitrogen atmosphere under ice cooling. The mixture is stirred for 5 minutes at room temperature. Then, a solution of di-t-butyl dicarbonate (34.11 g: 156.3 mmole) in dichloromethane (125 ml) is added dropwise, and the mixture is stirred for 40 minutes at room temperature to give (2R,4R)-1-t-butoxycarbonyl-4-hydroxy-2-methoxycarbonylpyrrolidine (26.85 g). Yield: 88%. Colorless crystals.

NMR δ (CDCl₃) ppm: 1.46(d, J=8.4 Hz, 9H), 2.0 to 2.2(m, 1H), 2.2 to 2.5(m, 1H), 3.4 to 3.8(m, 2H), 3.79(d, J=3.0 Hz, 3H), 4.2 to 4.5(m, 2H).

IR ν (KBr) cm⁻¹: 3460, 1730, 1680.

Step A-3. Preparation of a mesyl compound

To a solution of (2R,4R)-1-t-butoxycarbonyl-4-hydroxy-2-methoxycarbonylpyrrolidine (9.81 g: 40 mmole) in dichloromethane (49 ml) in a nitrogen atmosphere under ice cooling, triethylamine (6.67 ml: 48 mmole) and methanesulfonyl chloride (3.70 ml: 48 mmole) are added. The mixture is stirred for 20 minutes to give (2R,4R)-1-t-butoxycarbonyl-4-methanesulfonyloxy-2-methoxycarbonylpyrrolidine as a crude oil (13.05 g). Yield: 101%.

NMR δ (CDCl₃) ppm: 1.46(d, J=9.6 Hz, 9H), 2.5(m, 2H), 3.02(s, 3H), 3.76(s, 3H), 3.8(m, 2H), 4.3 to 4.6(m, 1H), 5.2 to 5.3(m, 1H).

Step A-4. Preparation of a methylol compound

To a solution of (2R,4R)-1-t-butoxycarbonyl-4-methanesulfonyloxy-2-methoxycarbonylpyrrolidine (11.21 g: 34.4 mmole) in a mixture of tetrahydrofuran (34 ml) and ethanol (51 ml), sodium borohydride (5.21 g: 137.7 mmole) is added in a nitrogen atmosphere under ice cooling. The mixture is stirred for 75 minutes at room temperature to give (2R,4R)-1-t-butoxycarbonyl-4-methanesulfonyloxypyrrolidine-2-methanol (8.47 g). Yield: 83%. Colorless crystals.

NMR δ (CDCl₃) ppm: 1.48(s, 9H), 1.9 to 2.2(m, 1H), 2.3 to 2.5(m, 1H), 3.06 (s, 3H), 3.65(dd, J=11.2 Hz, J=4.0 Hz, 1H), 3.5 to 3.9(m, 2H), 3.84(dd, J=11.2 Hz, J=7.6 Hz, 1H), 4.1(m, 1H), 5.2(m, 1H).

IR ν (KBr) cm⁻¹: 3490, 1688.

Step A-5. Preparation of an acetylthio compound (2R,4R)-1-t-Butoxycarbonyl-4-methanesulfonyloxypyrrolidine-2-methanol (i.e., a substrate) and potassium thioacetate (KSAc) are dissolved in dimethylformamide (DMF), and the mixture is stirred. The conditions for this reaction are shown in Table 1, Step A-5. The reaction mixture is diluted with ethyl acetate, and ice water is added. The organic layer is taken, successively washed with aqueous sodium hydroxide, hydrochloric acid, water and saturated brine, dried over magnesium sulfate, and concentrated in vacuo. The residue is purified by silica gel chromatography to give (2R,4S)-4-acetylthio-1-t-butoxycarbonylpyrrolidine-2-methanol.

NMR δ (CDCl₃) ppm: 1.47(s, 9H), 2.05(t, 2H), 2.34(s, 3H), 3.0 to 3.3(m, 1H), 3.40(dd, J=11.6 Hz, J=5.2 Hz, 1H), 3.5 to 3.9(m, 3H), 3.9 to 4.2(m, 2H).

Step A-6. Introduction of a sulfamide group a) Production of N-t-butoxycarbonylsulfamide A solution of t-butanol (4.72 ml: 50 mmole) in ethyl acetate (100 ml) is cooled to −40° C., chlorosulfonyl isocyanate (4.35 ml: 50 mmole) is dropwise added thereto, and the mixture is stirred at −18° C. for 20 minutes. The reaction mixture is cooled to −72° C., gaseous ammonia (2 mole) is bubbled with stirring, and the mixture is stirred for 50 minutes while warming up to 10° C. The reaction mixture is acidified with 5N-hydrochloric acid (30 ml) and the formed precipitate is filtered off. The organic layer is taken, successively washed with water and brine, dried over magnesium sulfate, and concentrated under reduced pressure. The crystalline residue is washed with hexane-ethyl acetate (1:5, 90 ml) and recrystallized from ethyl acetate-hexane to give N-t-butoxycarbonylsulfamide (8.81 g). Yield: 89%. Colorless crystals. mp.130° to 131° C.

NMR δ (CD₃SOCD₃) ppm: 1.43(s, 9H), 7.27(s, 2H).

IR ν (Nujol) cm⁻¹: 3360, 3270, 1718, 1548.

Elemental Analysis (C₅H₁₂N₂O₄S) Calcd.: C, 30.60; H, 6.17; N, 14.28; S, 16.34. Found: C, 30.39; H, 6.11; N, 14.30; S, 16.30.

b) Preparation of a sulfamide compound To a solution of (2R,4S)-4-acetylthio-1-t-butoxycarbonylpyrrolidine-2-methanol (i.e., a substrate) in tetrahydrofuran (THF) triphenylphosphine (PPh₃) N-t-butoxycarbonylsulfamide (BSMD), and azodicarboxylic acid diethyl ester (DEAD) are successively added under ice cooling. The conditions for this reaction are shown in Table 2, Step A-6. The reaction mixture is diluted with toluene, concentrated, diluted with toluene, and the formed crystals are filtered off. The filtrate is concentrated. The residue is purified by silica gel column chromatography to give (2R,4S)-4-acetylthio-1-t-butoxycarbonyl-2-(N-t-butoxycarbonyl-N-sulfamoylamino) methylpyrrolidine.

NMR δ (CDCl₃) ppm: 1.41(s, 9H), 1.55(s, 9H), 1.9 to 2.0(m, 2H), 2.35(s, 3H), 3.32(dd, J=11.4 Hz, J=8.2 Hz, 1H), 3.6 to 3.9(m, 3H), 3.9 to 4.1(m, 1H), 4.5(m, 1H), 6.15(s, 2H).

IR ν (KBr) cm⁻¹: 3420, 3320, 1706, 1686, 1666.

Step A-7. Removal of an acetyl group

To a solution of (2R,4S)-4-acetylthio-1-t-butoxycarbonyl-2-(N-t-butoxycarbonyl-N-sulfamoylamino) methylpyrrolidine (i.e., a substrate) in dichloromethane, 4.92M sodium methoxide (NaOMe) in methanol is added. The mixture is stirred. The conditions for this reaction are shown in Table 3, Step A-7. The reaction mixture is diluted with water. The water layer is taken, toluene is added thereto, and acidified with conc. hydrochloric acid under ice cooling. The organic layer is taken, successively washed with water and saturated brine, dried over magnesium sulfate, and concentrated in vacuo to give (2R,4S)-1-t-butoxycarbonyl-2-(N-t-butoxycarbonyl-N-sulfamoylamino) methyl-4-mercaptopyrrolidine. mp. 90.0° to 91.5° C.

NMR δ (CDCl₃) ppm: 1.43(s, 9H), 1.52(s, 9H), 1.72(d, J=7.0 Hz, 1H), 1.9 to 2.0(m, 2H), 3.2 to 3.8(m, 5H), 4.5(m, 1H), 6.11(s, 2H).

IR ν (KBr) cm⁻¹: 3220, 1698, 1683.

Elemental Analysis (C₁₅H₂₉O₆N₃S₂) Calcd. C:43.78, H:7.10, N:10.21, S:15.58. Found. C:43.55, H:7.11, N:10.37, S:15.75.

PREPARATIVE EXAMPLE 7-B OF A
PYRROLIDINE DERIVATIVE

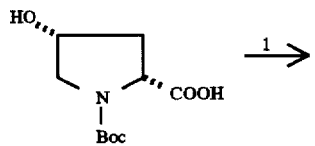

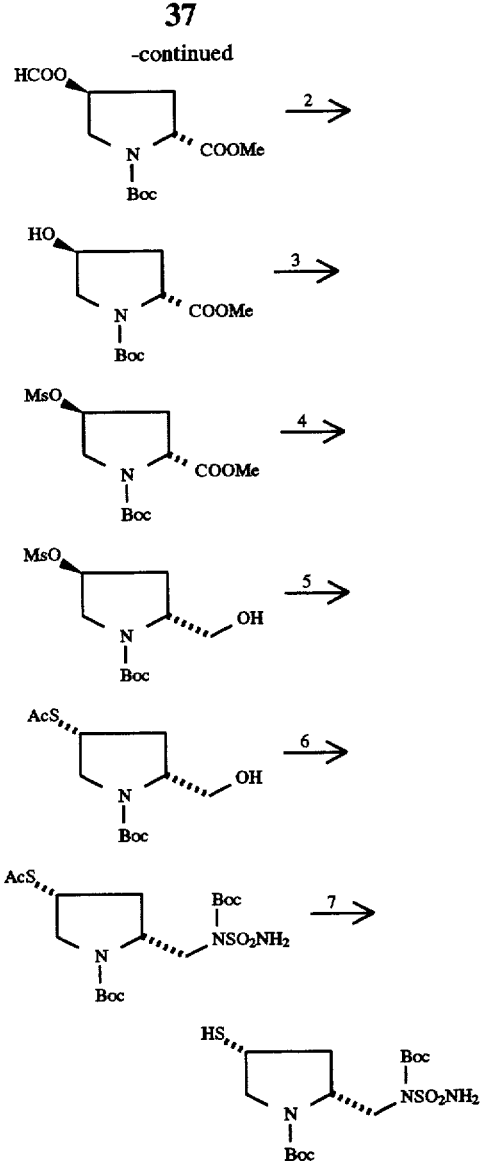

Step B-1. Substitution for a formyloxy group

To a solution of (2R,4R)-1-t-butoxycarbonyl-4-hydroxy-2-methoxycarbonylpyrrolidine (2.45 g: 10 mmole) in tetrahydrofuran (10 ml), formic acid (453 µl: 12 mmole), triphenylphosphine (3.15 g: 12 mmole), and diethyl azodicarboxylate (1.89 ml: 12 mmole) are successively added in a nitrogen atmosphere under ice cooling. The mixture is stirred for 30 minutes at the same temperature to give (2R,4S)-1-t-butoxycarbonyl-4-formyloxy-2-methoxycarbonylpyrrolidine (2.17 g). Yield: 79%. Colorless oil.

NMR δ (CDCl$_3$) ppm: 1.44(d, J=7.8 Hz, 9H), 2.1 to 2.6(m, 2H), 3.5 to 3.9(m, 5H), 4.4(m, 1H), 5.4(m, 1H), 8.0(s, 1H).

Step B-2. Removal of a formyl group

To a solution of (2R,4S)-1-t-butoxycarbonyl-4-formyloxy-2-methoxycarbonylpyrrolidine (2.08 g: 7.6 mmole) in methanol (21.0 ml), aqueous 1N-sodium hydroxide (7.6 ml) is added under ice cooling. The mixture is stirred at the same temperature for 25 minutes to give (2R, 4S)-1-t-butoxycarbonyl-4-hydroxy-2-methoxycarbonylpyrrolidine (1.86 Yield: 100%. Colorless oil.

NMR δ (CDCl$_3$) ppm: 1.44(d, J=9.2 Hz, 9H), 1.9 to 2.4(m, 2H), 3.4 to 3.7(m, 2H), 3.74 (s, 3H), 4.3 to 4.6(m, 2H).

Step B-3. Preparation of a mesyl compound

To a solution of (2R, 4S)-1-t-butoxycarbonyl-4-hydroxy-2-methoxycarbonylpyrrolidine (3.17 g: 12.9 mmole) in dichloromethane (16 ml) in a nitrogen atmosphere under ice cooling, triethylamine (2.15 ml: 15.5 mmole) and methanesulfonyl chloride (1.19 ml: 15.5 mmole) are added. The mixture is stirred to react for 30 minutes to give (2R,4S)-1-t-butoxycarbonyl-4-methanesulfonyloxy-2-methoxycarbonylpyrrolidine as oil (4.13 g). Yield: 99%.

NMR δ (CDCl$_3$) ppm: 1.46(d, J=8.4 Hz, 9H), 2.3(m, 1H), 2.5 to 2.8(m, 1H), 3.08(s, 3H), 3.8 to 4.0(m, 5H), 4.3 to 4.6(m, 1H), 5.3(m, 1H).

Step B-4. Preparation of a methylol compound

To a solution of (2R,4S)-1-t-butoxycarbonyl-4-methanesulfonyloxy-2-methoxycarbonylpyrrolidine (3.96 g: 12.2 mmole) in a mixture of tetrahydrofuran (12 ml) and ethanol (18 ml), sodium borohydride (1.85 g: 48.8 mmole) is added in a nitrogen atmosphere under ice cooling. The mixture is stirred for 45 minutes at room temperature to give (2R,4S)-1-t-butoxycarbonyl-4-methanesulfonyloxypyrrolidine-2-methanol (2.97 g). Yield: 83%. Colorless crystals. mp. 95° to 96° C.

NMR δ (CDCl$_3$) ppm: 1.49(s, 9H), 1.7 to 2.1(m, 1H), 2.3 to 2.5(m, 1H), 3.06(s, 3H), 3.4 to 3.7(m, 2H), 3.7 to 4.0(m, 2H), 4.0 to 4.3(m, 1H), 5.2(m, 1H).

IR ν (KBr) cm$^{-1}$: 3400, 3420, 1648.

Step B-5. Substitution for an acetylthio group (2R,4S)-1-t-butoxycarbonyl-4-methanesulfonyloxypyrrolidine-2-methanol (i.e., a substrate) is allowed to react in the same manner as in Step A-5 in Preparative Example 7-A under a condition for Step B-5 shown in Table 1 to give (2R,4R)-4-acetylthio-1-t-butoxycarbonylpyrrolidine-2-methanol.

NMR δ (CDCl$_3$) ppm: 1.47(s, 9H), 2.34(s, 3H), 2.4 to 3.2 (m, 2H), 3.58 to 4.1(m, 6H).

IR ν (CHCl$_3$) cm$^{-1}$: 3380, 1690.

Step B-6. Introduction of a sulfamide group

N-t-butoxycarbonylsulfamide is prepared in the same manner as in the paragraph (a) of Step A-6 in preparative Example 7-A. (2R,4R)-4-acetylthio-1-t-butoxycarbonylpyrrolidine-2-methanol (i.e., a substrate) is allowed to react with the obtained N-t-butoxycarbonylsulfamide in the similar manner as in paragraph (b) of Step A-6 in Preparative Example 7-A under a condition for Step B-6 shown in Table 2 to give (2R,4R)-4-acetylthio-1-t-butoxycarbonyl-2-(N-t-butoxycarbonyl-N-sulfamoylamino)methylpyrrolidine.

NMR δ (CDCl$_3$) ppm: 1.43(s, 9H), 1.53(s, 9H), 2.34(s, 3H), 2.5(m, 1H), 3.15(dd, J=12.2 Hz, J=6.2 Hz, 1H), 3.58 (dd, J=14.8 Hz, J=3.2 Hz, 1H), 3.8 to 4.1(m, 2H), 4.16(dd, J=12.2 Hz, J=7.8 Hz, 1H), 4.4 to 4.7 (m, 1H), 6.11(s, 2H).

IR ν (CHCl$_3$) cm$^{-1}$: 3360, 3200, 1710, 1688.

Step B-7. Removal of an acetyl group (2R,4R)-4-acetylthio-1-t-butoxycarbonyl-2-(N-t-butoxycarbonyl-N-sulfamoylamino) methylpyrrolidine (i.e., a substrate) is deacetylated in the similar manner as in Step A-7 of Preparative Example 7-A under a condition for Step B-7 shown in Table 3 to give (2R,4R)-1-t-butoxycarbonyl-2-(N-t-butoxycarbonyl-N-sulfamoylamino)methyl-4-mercaptopyrrolidine. mp. 92° to 93° C.

NMR δ (CDCl$_3$) ppm: 1.2 to 1.5(m, 1H), 1.42 (s, 9H), 1.54(s, 9H), 1.82(d, J=6.2 Hz, 1H), 2.5 to 2.7(m, 1H), 4.09, 3.05 (ABX, J=12.0 Hz, J=7.4 Hz, J=8.2 Hz, 2H), 4.06, 3.62(ABX, J=15.0 Hz, J=10.8 Hz, J=3.2 Hz, 2H), 4.2 to 4.6(m, 1H), 6.08(s, 2H).

IR ν (CHCl$_3$) cm$^{-1}$: 3380, 3220, 1718, 1680.

PREPARATIVE EXAMPLE 7-C OF A PYRROLIDINE DERIVATIVE

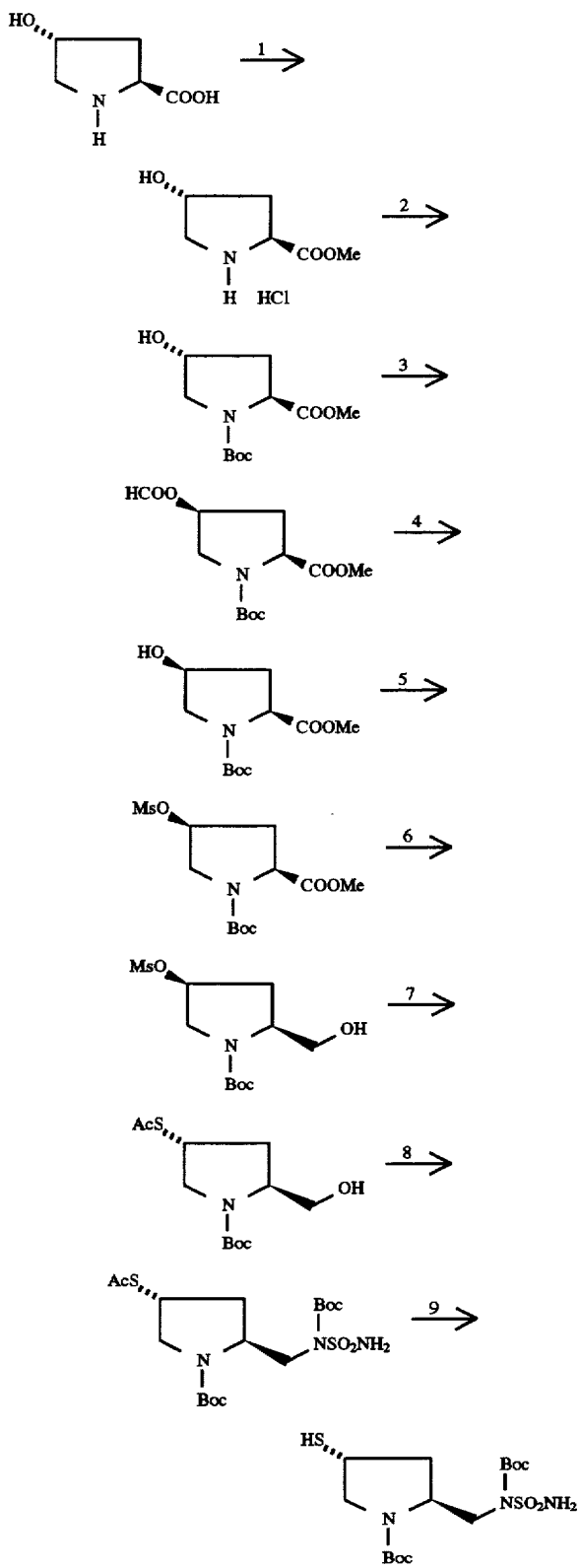

Step C-1. Preparation of an ester compound

To a suspension of trans-4-hydroxy-L-proline (200 g: 1.525 mole) in methanol (800 ml), acetylchloride (163 ml: 2.288 mole) is added dropwise under ice cooling in a nitrogen atmosphere. The mixture is warmed to room temperature, mixed with thionyl chloride (55.7 ml: 0.763 mole), and stirred for 4 hours at 40° C. to give (2S,4R)-4-hydroxy-2-methoxycarbonylpyrrolidine hydrochloride (244.27 g). Yield: 88%. Colorless crystals.

NMR δ (D₂O) ppm: 1.8 to 2.0(m, 1H), 2.0 to 2.2(m, 1H), 2.9 to 3.1(m, 1H), 3.17(dd, J=12.6 Hz, J=3.6 Hz, 1H), 3.49(s, 3H), 4.2 to 4.4(m, 2H).

IR ν (KBr) cm⁻¹: 3380, 3330, 2695, 2960, 1742.

Step C-2. Preparation of a Boc compound

To a suspension of (2S,4R)-4-hydroxy-2-methoxycarbonylpyrrolidine hydrochloride (12.71 g: 70 mmole) in dichloromethane (70 ml), triethylamine (10.7 ml: 77 mmole) is added dropwise under ice cooling in a nitrogen atmosphere. The mixture is stirred for 5 min. at room temperature. A solution of di-t-butyl dicarbonate (19.10 g: 87.5 mmole) in dichloromethane (72 ml) is added dropwise thereto, and the mixture is stirred for 45 minutes at room temperature to give (2S,4R)-1-t-butoxycarbonyl-4-hydroxy-2-methoxycarbonylpyrrolidine (14.06 g). Yield: 82%. Colorless oil.

NMR δ (CDCl₃) ppm: 1.44(d, J=9.6 Hz, 9H), 1.9 to 2.4(m, 3H), 3.4 to 3.7(m, 2H), 3.74 (s, 3H), 4.3 to 4.6(m, 2H).

Step C-3. Substitution with a formyloxy group

To a solution of (2S,4R)-1-t-butoxycarbonyl-4-hydroxy-2-methoxycarbonylpyrrolidine (7.36 g: 30 mmole) in tetrahydrofuran (30 ml), formic acid (1.36 ml: 36 mmole), triphenylphosphine (9.44 g: 36 mmole) and diethyl azodicarboxylate (5.67 ml: 36 mmole) are successively added in a nitrogen atmosphere under ice cooling. The mixture is stirred to react for 40 minutes at the same temperature to give (2S,4S)-1-t-butoxycarbonyl-4-formyloxy-2-methoxycarbonylpyrrolidine (5.38 g). Yield: 66%. Colorless crystals.

NMR δ (CDCl₃) ppm: 1.45(d, J=8.6 Hz, 9H), 2.2 to 2.4(m, 1H), 2.4 to 2.7(m, 1H), 3.5 to 3.9(m, 2H), 3.75(s, 3H), 4.3 to 4.6(m, 1H), 5.3 to 5.5(m, 1H), 7.98 (s, 1H).

IR ν (KBr) cm⁻¹: 3420, 1748, 1712, 1681.

Step C-4. Removal of a formyl group

To a solution of (2S,4S)-1-t-butoxycarbonyl-4-formyloxy-2-methoxycarbonylpyrrolidine (5.12 g: 18.7 mmole) in methanol (51.0 ml), aqueous 1N-sodium hydroxide (18.7 ml) is added under ice cooling. The mixture is stirred at the same temperature for 20 minutes to give (2S,4S)-1-t-butoxycarbonyl-4-hydroxy-2-methoxycarbonylpyrrolidine (4.09 g). Yield: 89%. Colorless crystals.

NMR δ (CDCl₃) ppm: 1.44(d, J=8.2 Hz, 9H), 2.0 to 2.2(m, 1H), 2.2 to 2.5(m, 1H), 3.2 to 3.8(m, 3H), 3.79(d, J=2.8 Hz, 3H), 4.2 to 4.5(m, 2H).

IR ν (KBr) cm⁻¹: 3460, 1728, 1677.

Step C-5. Preparation of a mesyl compound

In a manner similar to Step A-3 in Preparative Example 7-A, (2S,4S)-1-t-butoxycarbonyl-4-hydroxy-2-methoxycarbonylpyrrolidine in dichloromethane is mesylated with triethylamine and methanesulfonylchloride in a nitrogen atmosphere under ice cooling to give (2S,4S)-1-t-butoxycarbonyl-4-methanesulfonyloxy-2-methoxycarbonylpyrrolidine. mp. 90.0° to 91.5° C.

Step C-6. Preparation of a methylol compound

In a similar manner to that in Step A-4 in Production Example 7-A, (2S,4S)-1-t-butoxycarbonyl-4-methanesulfonyloxy-2-methoxycarbonylpyrrolidine is allowed to react to give (2S,4S)-1-t-butoxycarbonyl-4-methanesulfonyloxypyrrolidine-2-methanol.

Step C-7. Preparation of an acetylthio compound (2S,4S)-1-t-butoxycarbonyl-4-methanesulfonyloxypyrrolidine-2-methanol (i.e., a substrate) is allowed to react in a similar manner to Step A-5 in Preparative Example 7-A under a condition for Step C-7 shown in Table 1 to give (2S,4R)-4-acetylthio-1-t-butoxycarbonylpyrrolidine-2-methanol.

NMR δ (CDCl₃) ppm: 1.47(s, 9H), 2.05 (t, 2H), 2.34 (s, 3H), 3.0 to 3.3 (m, 1H), 3.40(dd, J=11.6 Hz, J=5.2 Hz, 1H), 3.5 to 3.9(m, 3H), 3.9 to 4.2(m, 2H).

Step C-8. Introduction of a sulfamide group

N-t-butoxycarbonylsulfamide is prepared in the same manner as in the paragraph (a) in Step A-6 in Preparative Example 7-A. (2S,4R)-4-Acetylthio-1-t-butoxycarbonylpyrrolidine-2-methanol (i.e., a substrate) is allowed to react with N-t-butoxycarbonylsulfamide in the similar manner as in the paragraph (b) in Step A-6 in Production Example 7-A under a condition for Step C-8 shown in Table 2 to give (2S,4R)-4-acetylthio-1-t-butoxycarbonyl-2-(N-t-butoxycarbonyl-N-sulfamoylamino) methylpyrrolidine.

NMR δ (CDCl₃) ppm: 1.41(s, 9H), 1.55(s, 9H), 1.9 to 2.0 (m, 2H), 2.35(s, 3H), 3.32(dd, J=11.4 Hz, J=8.2 Hz, 1H), 3.6 to 3.9(m, 3H), 3.9 to 4.1(m, 1H), 4.5(m, 1H), 6.15(s, 2H).

IR ν (KBr) cm⁻¹: 3420, 3320, 1706, 1686, 1666.

Step C-9. Removal of an acetyl group (2S,4R)-4-acetylthio-1-t-butoxycarbonyl-2-(N-t-butoxycarbonyl-N-sulfamoylamino) methylpyrrolidine (i.e., a substrate) is allowed to react in the similar manner as in Step A-7 in Preparative Example 7-A under a condition for Step C-9 shown in Table 3 to give (2S,4R)-1-t-butoxycarbonyl-2-(N-t-butoxycarbonyl-N-sulfamoylamino) methyl-4-mercaptopyrrolidine. mp. 90.0° to 91.5° C.

NMR δ (CDCl₃) ppm: 1.43(s, 9H), 1.52(s, 9H), 1.72(d, J=7.0 Hz, 1H), 1.9 to 2.0(m, 2H), 3.2 to 3.8(m, 5H), 4.5 (m, 1H), 6.11(s, 2H).

IR ν (KBr) cm⁻¹: 3220, 1698, 1683.

PREPARATIVE EXAMPLE 7-D OF A PYRROLIDINE DERIVATIVE

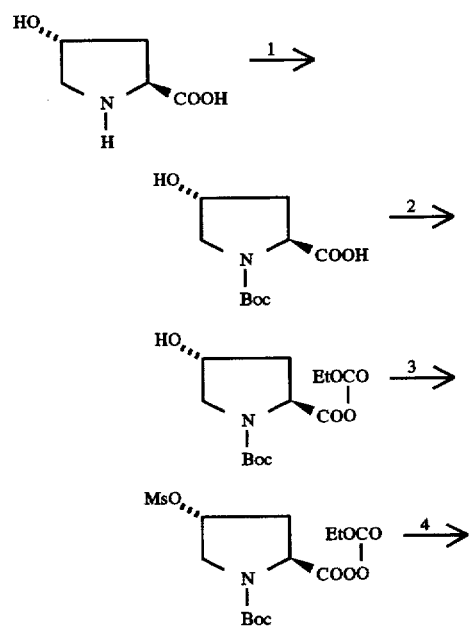

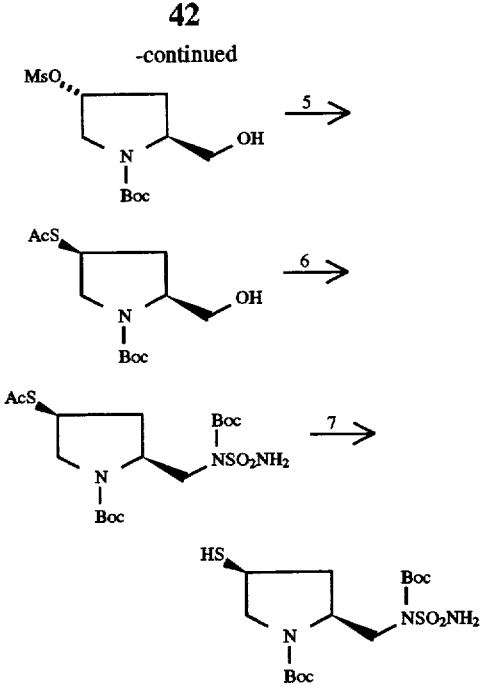

Step D-1. Preparation of an N-Boc compound

To a suspension of trans-4-hydroxy-L-proline (50 g: 0.381 mole) in methanol (250 ml), a solution of 4N-sodium hydroxide (95.4 ml: 0.381 mole) and di-t-butyl dicarbonate (91.6 g: 0.42 mole) in methanol (55 ml) is added at -20° C. The mixture is stirred at 20° C. for 3 hours. The reaction mixture is concentrated and then diluted with toluene (100 ml) and shaken. The aqueous layer is taken, and mixed with conc. hydrochloric acid (36 ml) under ice cooling, saturated brine (100 ml), and ethyl acetate (800 ml). The organic layer is taken, washed with saturated brine, dried over sodium sulfate, and concentrated under reduced pressure. The residue is recrystallized from a toluene-ethyl acetate mixture to give (2S,4R)-1-t-butoxycarbonyl-2-carboxy-4-hydroxypyrrolidine (84.7 g). Yield: 96%. Colorless crystals. mp. 126° to 128° C.

NMR δ (CDCl₃) ppm: 1.43, 1.46(2×s, 9H), 1.95 to 2.36(m, 2H), 3.36 to 3.6(m, 2H), 4.23 to 4.44(m, 2H).

IR ν (CHCl₃) cm⁻¹: 3360, 1735, 1656.

Step D-2. Protection of a carboxyl group

To a solution of (2S,4R)-1-t-butoxycarbonyl-4-hydroxy-L-proline (84.5 g: 0.365 mole) in dichloromethane (1.27 liter) in a nitrogen atmosphere at -30° C., triethylamine (61.1 ml: 0.438 mole) and ethyl chloroformate (38.4 ml: 0.402 mole) are added, and the mixture is stirred for 40 minutes.

Step D-3. Preparation of an O-mesyl compound

The resulting reaction mixture containing (2S,4R)-1-t-butoxycarbonyl-2-ethoxycarbonyloxycarbonyl-4-hydroxypyrrolidine obtained in Step D-2 is cooled to -40° C., triethylamine (61.1 ml: 0.438 mole) and methanesulfonyl chloride (31.1 ml: 0.402 mole) are added thereto, and the mixture is stirred for 40 minutes.

Step D-4. Reduction

To the resulting reaction mixture containing (2S,4R)-1-t-butoxycarbonyl-2-ethoxycarbonyloxycarbonyl-4-methane sulfonyloxypyrrolidine obtained in Step D-3 cooling at -40° C., tetra-n-butylammonium bromide (11.8 g: 0.0365 mole) and a solution of sodium borohydride (52.5 g: 1.35 mole) in water (55 ml) are added. The mixture is allowed to warm to -10° C. and stirred for 1 hour. The aqueous layer is acidified with dilute hydrochloric acid to pH 3. The organic layer is taken, successively washed with aqueous sodium hydrogen carbonate and water, dried over magnesium sulfate, and concentrated under reduced pressure. The residue is recrystallized from a toluene-hexane mixture to give (2S,4R)-1-t-butoxycarbonyl-4-methanesulfonyloxypyrrolidine-2-methanol (101.3 g). Yield: 94%. Colorless crystals. mp. 95° to 96° C.

NMR δ (CDCl$_3$) ppm: 1.48(s, 9H), 1.78 to 2.02(m, 1H), 2.3 to 2.48(m, 1H), 3.05 (s, 3H), 3.5 to 3.65(m, 2H), 3.65 to 4.0(m, 2H), 4.03 to 4.25 (m, 1H), 5.2(s, 1H).

IR ν (CHCl$_3$) cm$^{-1}$: 3460, 1680.

Step D-5. Substitution for an acetylthio group

A solution of (2R,4S)-1-t-butoxycarbonyl-4-methanesulfonyloxypyrrolidine-2-methanol (i.e., a substrate) (11.8 g: 40 mmole) and potassium thioacetate (5.94 g: 52 mmole) in dimethylformamide (120 ml) is stirred at 65° C. for 3.75 hours. The reaction mixture is mixed with ethyl acetate (330 ml), ice water (100 ml), and 1N-hydrochloric acid (20 ml) to adjust the aqueous layer at pH 4. The organic layer is taken, successively washed with water and saturated brine, dried over sodium sulfate, and concentrated under reduced pressure. The residue is purified by silica gel chromatography (toluene-ethyl acetate=2:1) to give (2S,4S)-4-acetylthio-1-t-butoxycarbonylpyrrolidine-2-methanol (9.48 g). Yield: 86%. Pale orange colored oil.

NMR δ (CDCl$_3$) ppm: 1.47(s, 9H), 2.34(s, 3H), 2.4 to 3.2(m, 2H), 3.58 to 4.1(m, 6H).

IR ν (CHCl$_3$) cm$^{-1}$: 3380, 1690.

Step D-6. Introduction of a sulfamide group

N-t-butoxycarbonylsulfamide is prepared in the same manner as in the paragraph (a) of Step A-6 in Preparative Example 7-A. To a solution of (2S,4S)-4-acetylthio-1-t-butoxycarbonylpyrrolidine-2-methanol (i.e., a substrate) (9.04 g: 32.8 mmole) in tetrahydrofuran (THF) (95 ml), triphenylphosphine (PPh$_3$) (10.16 g: 38.7 mmole), N-t-butoxycarbonylsulfamide (BSMD) (9.66 g: 49.2 mmole), and azodicarboxylic acid diethyl ester (DEAD) (6.20 ml: 39.4 mmole) are successively added under ice cooling. The conditions for this reaction are shown in Table 2.

Step D-6. The reaction mixture is diluted with toluene (30 ml), concentrated, diluted with toluene (60 ml), and the formed crystals are filtered off. The filtrate is concentrated.

Step D-7. Removal of an acetyl group

The residue obtained in Step D-6 is dissolved in toluene (95 ml), then, 4.92M sodium methoxide in methanol (20 ml: 98.4 mmole) is added at −35° C., and the mixture is stirred for 30 minutes. The reaction mixture is diluted with water (100 ml). The aqueous layer is taken, ethyl acetate (300 ml) is added, mixed with concentrated hydrochloric acid (10 ml) under ice cooling, and the mixture is stirred. The organic layer is taken, successively washed with water and brine, dried over sodium sulfate, and concentrated under reduced pressure. The residue is purified by silica gel chromatography. Obtained colorless oil is recrystallized from toluene-hexane mixture to give (2S,4S)-1-t-butoxycarbonyl-2-(N-t-butoxycarbonyl-N-sulfamoylamino) methyl-4-mercaptopyrrolidine (9.32 g). Yield: 69%. Colorless crystals. mp. 92° to 93° C.

NMR δ (CDCl$_3$) ppm: 1.2 to 1.5(m, 1H), 1.42(s, 9H), 1.54(s, 9H), 1.82 (d, J=6.2 Hz, 1H), 2.5 to 2.7(m, 1H), 4.09, 3.05(ABX, J=12.0 Hz, J=7.4 Hz, J=8.2 Hz, 2H), 4.06, 3.62(ABX, J=15.0 Hz, J=10.8 Hz, J=3.2 Hz, 2H), 4.2 to 4.6(m, 1H), 6.08(s, 2H).

IR ν (CHCl$_3$) cm$^{-1}$: 3380, 3220, 1718, 1680.

Elemental Analysis (C$_{15}$H$_{29}$N$_3$O$_6$S$_2$) Calcd. : C, 43.78; H, 7.10; N, 10.21; S, 15.58

Found: C, 43.64; H, 7.10; N, 10.19; S, 15.34

TABLE 1

| Step | KSAc equiv.[a] | DMF vol.[b] | Temp. °C. | Time min. | Yield % |
| --- | --- | --- | --- | --- | --- |
| A-5 | 1.55 | 20 fold | 70 | 90 | 75 |
| B-5 | 1.20 | 5 fold | 70 | 300 | 81 |
| C-7 | 1.30 | 10 fold | 65 | 105 | 70 |
| D-5 | 1.30 | 10 fold | 65 | 225 | 86 |

[a] Molar ratio to the substrate
[b] The volume (ml) of the solvent to the weight (g) of the substrate

TABLE 2

| Step | THF vol.[c] | PPh$_3$ equiv.[d] | BSMD equiv.[d] | DEAD equiv.[d] | Temp. | Time min. | Yield % |
| --- | --- | --- | --- | --- | --- | --- | --- |
| A-6 | 20 fold | 1.34 | 1.20 | 1.30 | 45° C. | 150 | 76 |
| B-6 | 7 fold | 1.50 | 1.66 | 1.50 | 0° C. | 300 | 84 |
| C-8 | 10 fold | 1.28 | 1.50 | 1.30 | room temp. | 240 | 82 |
| D-6 | 11 fold | 1.18 | 1.50 | 1.20 | room temp. | 180 | —[e] |

[c] The volume (ml) of the solvent to the weight (g) of the substrate
[d] Molar ratio to the substrate
[e] Not measured

TABLE 3

| Step | NaOMe equiv.[f] | Solvent[g] vol.[h] | Temp. °C. | Time min. | Yield % |
| --- | --- | --- | --- | --- | --- |
| A-7 | 1.5 | 15 fold | −40 | 120 | 72 |
| B-7 | 2.0 | 5 fold | −10 | 60 | 70 |
| C-9 | 3.0 | 4 fold | −35 | 30 | 85 |
| D-7 | 3.0 | 11 fold | −35 | 30 | 69 |

[f] Molar ratio to the substrate
[g] Dichloromethane is used in Steps A-7, B-7, C-9 and toluene is used in Step D-7.
[h] The volume (ml) of the solvent to the weight (g) of the substrate

PREPARATIVE EXAMPLE 8 OF A PYRROLIDINE DERIVATIVE

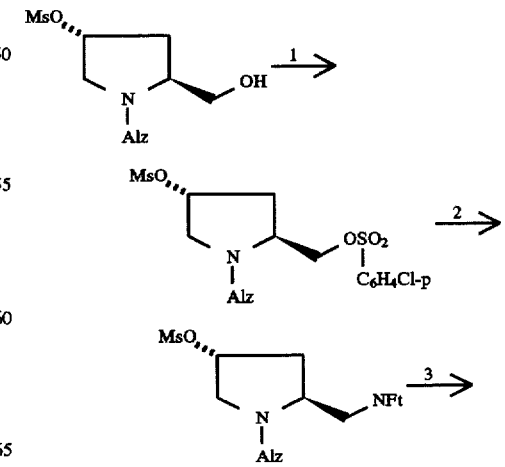

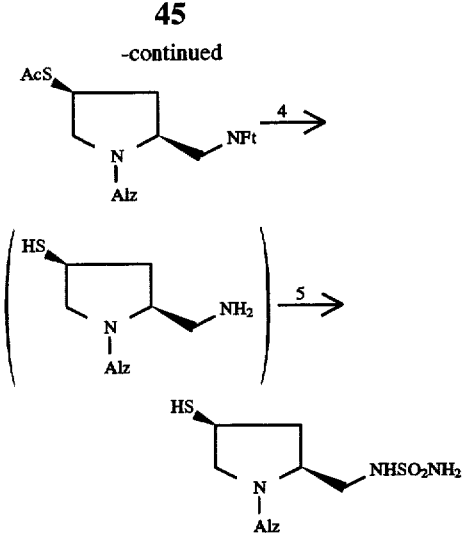

Step 1. Preparation of a p-chlorobenzenesulfonyl compound

To a solution of (2S,4R)-1-allyloxycarbonyl-4-methanesulfonyloxypyrrolidine-2-methanol (13.4 g: 50 mmole) in dichloromethane (50 ml), p-chlorobenzenesulfonyl chloride (12.66 g: 60 mmole) is added in a nitrogen atmosphere at room temperature and a solution of triethylamine (8.69 ml: 62.5 mmole) in dichloromethane (10 ml) is further added dropwise. The mixture is stirred at room temperature overnight. The reaction mixture is successively washed with aqueous sodium hydrogen carbonate and saturated brine, dried over magnesium sulfate, concentrated in vacuo, and purified by silica gel chromatography (toluene-ethyl acetate) to give crude (2S,4R)-1-allyloxycarbonyl-2-p-chlorobenzenesulfonyloxymethyl-4-methanesulfonyloxypyrrolidine (23.73 g) as oil. Yield: 105%.

NMR δ (CDCl₃) ppm: 2.2 to 2.6(m, 2H), 3.04(s, 3H), 3.58(dd, J=5.0 Hz, J=11.4 Hz, 1H), 3.8 to 4.0(m, 1H), 4.1 to 4.3(m, 3H), 4.5(m, 3H), 5.1 to 5.4(m, 3H), 5.7 to 6.0(m, 1H).

Step 2. Preparation of a phthalimide compound

To a solution of (2S,4R)-1-allyloxycarbonyl-2-p-chlorobenzenesulfonyloxymethyl-4-methanesulfonyloxypyrrolidine (23.7 g: ca. 50 mmole) in dimethylformamide (50 ml), potassium phthalimide (10.2 g: 55 mmole) is added in a nitrogen atmosphere, and the mixture is stirred at 60° C. for 3.5 hours. The reaction mixture is poured into a stirring mixture of ice water (500 ml) and ethyl acetate (500 ml). The organic layer is successively washed with water (4 times) and saturated brine, dried over magnesium sulfate, and concentrated in vacuo. The residue is recrystallized from a mixture of n-hexane and toluene. The solid is filtered off and the filtrate is purified by silica gel chromatography (toluene-ethyl acetate) to give crude (2S,4R)-1-allyloxycarbonyl-2-phthalimidomethyl-4-methanesulfonyloxypyrrolidine (12.41 g). Yield: 61%. Colorless oil.

Step 3. Preparation of an acetylthio compound

A solution of (2S,4R)-1-allyloxycarbonyl-2-phthalimidomethyl-4-methanesulfonyloxypyrrolidine (12.4 g: 30.46 mmole) and 90% potassium thioacetate (5.22 g: 45.69 mmole) in dimethylformamide (130 ml) is heated with stirring at 60° C. for 4 hours. The reaction mixture is diluted with ethyl acetate (200 ml) and ice water (200 ml). The organic layer is taken, successively washed with water (3 times) and saturated brine, dried over magnesium sulfate, and concentrated in vacuo. The residue is purified by silica gel chromatography to give crude (2S,4S)-4-acetylthio-1-allyloxycarbonyl-2-phthalimidomethylpyrrolidine (9.33 g). Yield: 81%.

NMR δ (CDCl₃) ppm: 1.7 to 1.9(m, 1H), 2.33(s, 3H), 2.4 to 2.7(m, 1H), 3.25 (dd, J=6.8 Hz, J=11.4 Hz, 1H), 3.7 to 4.0(m, 2H), 4.0 to 4.2(m, 2H), 4.3 to 4.6(m, 3H), 5.0 to 5.3(m, 2H), 5.7 to 5.9(m, 1H), 7.7(m, 2H), 7.85(m, 2H).

Step 4. Removal of a phthalyl and an acetyl groups

To a solution of crude (2S,4S)-1-acetylthio-1-allyloxycarbonyl-2-phthalimidomethylpyrrolidine (5.61 g: 14.90 mmole) in dichloromethane (5.4 ml), and methanol (5.4 ml), hydrazine monohydrate (2.17 ml: 44.7 mmole) is added. The mixture is heated at 60° C. with stirring for 4 hours. The solid in the reaction mixture is filtered off, washed with dichloromethane (70 ml) and the washing is combined with the filtrate. The mixture is concentrated to give crude (2S,4S)-2-aminomethyl-1-allyloxycarbonyl-4-mercaptopyrrolidine (2.80 g). Yield: 68%. Oil.

Step 5. Preparation of a sulfamoyl compound

To a solution of (2S,4S)-2-aminomethyl-1-allyloxycarbonyl-4-mercaptopyrrolidine (2.80 g: ca. 13.14 mmole) in dichloromethane (66 ml) at −50° C., triethylamine (4.02 ml: 28.91 mmole) and trimethylchlorosilane (3.76 ml: 28.91 mmole) are added dropwise over 15 minutes. The mixture is stirred at the same temperature for 20 minutes. To the reaction mixture triethylamine (0.92 ml: 6.57 mmole) and a solution of sulfamoyl chloride (19.37 mmole) in dichloromethane (6.8 ml) are added dropwise over 20 minutes at −70° C., and the mixture is stirred for 30 minutes. To the reaction mixture triethylamine (3.84 ml: 27.59 mmole) is again added over 1 hour at −50° C. The reaction mixture is kept at the same temperature overnight and concentrated in vacuo. The residual oil is purified by silica gel chromatography (ethyl acetate) to give (2S,4S)-1-allyloxycarbonyl-2-(sulfamoylamino)methyl-4-mercaptopyrrolidine (2.64 g). Yield: 68%. White powder.

NMR δ (CDCl₃) ppm: 1.4 to 1.6(m, 1H), 1.83(d, J=6.2 Hz, 1H), 2.5 to 2.7(m, 1H), 3.11(dd, J=8.2 Hz, J=11.6 Hz, 1H), 3.3 to 3.4(m, 1H), 3.71(dd, J=2.9 Hz, J=15.2 Hz, 1H), 4.13(dd, J=7.3 Hz, J=11.7 Hz, 1H), 4.16(dd, J=10.3, 14.9 Hz, 1H), 4.3 to 4.6(m, 3H), 4.7(m, 2H), 5.2 to 5.4(m, 4H), 5.8 to 6.0(m, 2H), 6.0(m, 2H).

IR ν (CHCl₃) cm⁻¹: 1684, 1158.

PREPARATIVE EXAMPLE 9 OF A PYRROLIDINE DERIVATIVE

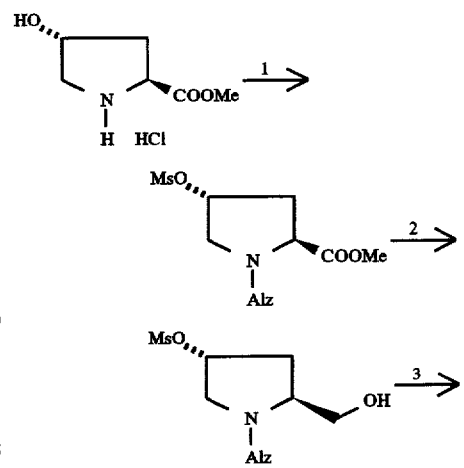

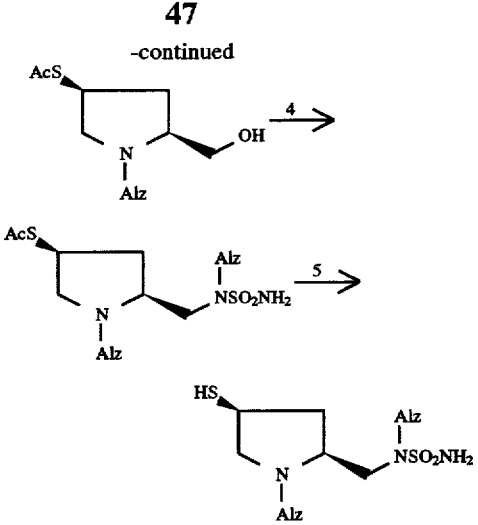

Step 1. Preparation of an N-protected and an O-mesyl compound

To a suspension of (2S,4R)-4-hydroxy-2-methoxycarbonylpyrrolidine hydrochloride (17.0 g: 100 mmole) in dichloromethane (200 ml), triethylamine (29.2 ml: 210 mmole) is added in a nitrogen atmosphere under ice cooling. The mixture is stirred for 5 minutes at room temperature, mixed dropwise with a solution of allyl chloroformate (11.2 ml: 100 mmole) in dichloromethane (20 ml), stirred for 1 hour at room temperature, and diluted with water (250 ml). The organic layer is taken, successively washed with water and saturated brine, dried over magnesium sulfate, and concentrated in vacuo to give (2S,4R)-1-allyloxycarbonyl-4-hydroxy-2-methoxycarbonylpyrrolidine (21.82 g) as oil. To a solution of this product in dichloromethane (100 ml), triethylamine (16.7 ml: 120 mmole) and methanesulfonylchloride (9.2 ml: 120 mmole) are added in a nitrogen atmosphere under ice cooling, and the mixture is stirred for 10 minutes. The reaction mixture is successively washed with aqueous sodium hydrogen carbonate and saturated brine, dried over magnesium sulfate, concentrated in vacuo, and purified by silica gel chromatography (toluene-ethyl acetate) to give (2S,4R)-1-allyloxycarbonyl-4-methanesulfonyloxy-2-methoxycarbonylpyrrolidine (27.62 g) as oil. Yield: 90%.

NMR δ (CDCl₃) ppm: 2.2 to 2.4(m, 1H), 2.2 to 2.5(m, 1H), 2.5 to 2.8(m, 2H), 3.06(s, 3H), 3.74 & 3.77(2×s, 3H), 3.8 to 4.0(m, 2H), 4.4 to 4.7(m, 3H), 5.2 to 5.4(m, 3H), 5.8 to 6.0(m, 1H).

Step 2. Preparation of a methylol compound

To a solution of (2S,4R)-1-allyloxycarbonyl-4-methanesulfonyloxy-2-methoxycarbonylpyrrolidine (27.12 g: 74.0 mmole) in a mixture of tetrahydrofuran (94 ml) and ethanol (140 ml), sodium borohydride (12 g: 31.7 mmole) is added in a nitrogen atmosphere under ice cooling. The mixture is stirred for 4 hours at room temperature. To the reaction mixture concentrated sulfuric acid (8.8 ml: 158.4 mmole) is added dropwise under ice cooling. The reaction mixture is concentrated to half a volume in vacuo, and diluted with ethyl acetate (100 ml) and ice water (100 ml). The organic layer is taken, successively washed with aqueous sodium hydrogen carbonate and saturated brine, dried over magnesium sulfate, and concentrated in vacuo to give (2S,4R)-1-allyloxycarbonyl-4-methanesulfonyloxypyrrolidine-2-methanol (19.33 g). Yield: 77%. Colorless oil.

NMR δ (CDCl₃) ppm: 1.9 to 2.1(m, 1H), 2.3 to 2.5(m, 1H), 3.05(s, 3H), 3.5 to 3.7(m, 2H), 3.7 to 4.1(m, 2H), 4.1 to 4.3(m, 1H), 4.6(m, 2H), 5.2 to 5.4(m, 3H), 5.8 to 6.1(m, 1H).

Step 3. Preparation of an acetylthio compound

A solution of (2S,4R)-1-allyloxycarbonyl-4-methanesulfonyloxypyrrolidine-2-methanol (19.32 g: 69.17 mmole) and 90% potassium thioacetate (10.73 g: 89.9 mmole) in dimethylformamide (217 ml) is heated with stirring at 65° C. for 5 hours. To the reaction mixture ethyl acetate (200 ml) and ice water (200 ml) are added. The organic layer is taken, successively washed with aqueous 0.05N-sodium hydroxide, 0.1N-hydrochloric acid, water and saturated brine, dried over magnesium sulfate, and concentrated in vacuo. The residue is purified by silica gel chromatography to give (2S,4S)-4-acetylthio-1-allyloxycarbonylpyrrolidine-2-methanol (15.34 g). Yield: 90%.

NMR δ (CDCl₃) ppm: 1.5 to 1.7(m, 1H), 2.34(s, 3H), 2.4 to 2.6(m, 1H), 3.19(dd, J=8.0 Hz, J=11.5 Hz, 1H), 3.6 to 3.8(m, 2H), 3.8 to 4.0(m, 1H), 4.0 to 4.2(m, 2H), 4.6(m, 2H), 5.2 to 5.4(m, 2H), 5.8 to 6.1(m, 1H).

Step 4. Preparation of a sulfamide compound

To a solution of (2S,4S)-4-acetylthio-1-allyloxycarbonylpyrrolidine-2-methanol (8.02 g: ca. 30 mmole) in ethyl acetate (83 ml) under ice cooling, triphenylphosphine (9.44 g: 13.6 mmole), N-allyloxycarbonylsulfamide (3.12 g: 15.9 mmole), and azodicarboxylic acid diethylester (5.67 ml: 36 mmole) are successively added. The mixture is stirred under ice cooling for 55 minutes and at room temperature for 4 hours. The reaction mixture is dissolved in toluene (60 ml), concentrated, diluted with toluene (60 ml), filtered to remove separating crystals, and the filtrate is concentrated. The residue is purified by silica gel chromatography to give (2S,4S)-4-acetylthio-1-allyloxycarbonyl-2-(N-sulfamoyl-N-allyloxycarbonylamino)methylpyrrolidine (6.74 g). Yield: 55%. Colorless oil.

NMR δ (CDCl₃) ppm: 1.5 to 1.7(m, 1H), 2.35(s, 3H), 2.5 to 2.7(m, 1H), 3.19 (dd, J=6.3 Hz, J=11.5 Hz, 1H), 3.68(dd, J=3.8 Hz, J=14.5 Hz, 1H), 3.9 to 4.3(m, 3H), 4.3 to 4.7(m, 5H), 5.2 to 5.4(m, 4H), 5.8 to 6.1(m, 4H).

Step 5. Removal of an acetyl group

To a solution of (2S,4S)-4-acetylthio-1-allyloxycarbonyl-2-(N-sulfamoyl-N-allyloxycarbonylamino)methylpyrrolidine (6.70 g: 16.4 mmole) in toluene (50 ml), 4.92M solution of sodium methoxide in methanol (5.0 ml: 24.7 mmole) is added at −30° C. The mixture is stirred for 30 minutes, and diluted with water (55 ml). The aqueous layer is taken, diluted with toluene (50 ml), acidified with concentrated hydrochloric acid (2.3 ml) under ice cooling, and stirred. The organic layer is taken, successively washed with water and saturated brine, dried over magnesium sulfate and concentrated in vacuo. The residual oil is purified by silica gel chromatography (toluene-ethyl acetate) to give (2S,4S)-1-allyloxycarbonyl-2-(N-sulfamoyl-N-allyloxycarbonylamino)methyl-4-mercaptopyrrolidine (4.89 g). Yield: 78%. Colorless oil.

NMR δ (CDCl₃) ppm: 1.5 to 1.7(m, 1H), 2.35(s, 3H), 2.5 to 2.7(m, 1H), 3.19(dd, J=6.3 Hz, J=11.5 Hz, 1H), 3.68(dd, J=3.8 Hz, J=14.5 Hz, 1H), 3.9 to 4.3(m, 3H), 4.3 to 4.7(m, 5H), 5.2 to 5.4(m, 4H), 5.8 to 6.1(m, 4H).

IR ν (CHCl$_3$) cm$^{-1}$: 1718, 1684, 1179, 1160.

EXAMPLES

| Example | X$^1$ | X$^2$ | Y$^2$ | —NSO$_2$N(R$^4$)(R$^2$)(R$^3$) |
|---|---|---|---|---|
| 1 | H | PMB | Boc | —NHSO$_2$NH$_2$ |
| 2 | H | PNB | Pnz | —NHSO$_2$NH$_2$ |
| 3 | H | PMB | Pmz | —NHSO$_2$N(H)(Pmz) |
| 4 | H | PMB | Pmz | —NHSO$_2$N(Pmz)(Me) |
| 5 | H | PMB | Pmz | —NHSO$_2$N(Me)(Me) |
| 6 | SiMe$_3$ | CHPh$_2$ | Boc | —N(Boc)(SO$_2$NH$_2$) |
| 7 | H | PMB | Pmz | —NHSO$_2$NHCH$_2$CH$_2$OH |
| 8 | H | PMB | Pmz | cyclic —N-S(O$_2$)-NPmz (5-membered) |
| 9 | H | PMB | Pmz | cyclic —N-S(O$_2$)-NPmz (6-membered) |

| Example | —NSO$_2$N(R$^4$)(R$^2$)(R$^3$) |
|---|---|
| 1 | —NHSO$_2$NH$_2$ |
| 2 | —NHSO$_2$NH$_2$ |
| 3 | —NHSO$_2$NH$_2$ |
| 4 | —NHSO$_2$NHMe |
| 5 | —NHSO$_2$N(Me)(Me) |
| 6 | —NHSO$_2$NH$_2$ |
| 7 | —NHSO$_2$NHCH$_2$CH$_2$OH |
| 8 | cyclic —N-S(O$_2$)-NH (5-membered) |
| 9 | cyclic —N-S(O$_2$)-NH (6-membered) |

EXAMPLE 1

Synthesis of a (3S,5S)-pyrrolidylthiocarbapenem derivative

Step 1. Preparation of a protected pyrrolidylthiocarbapenem derivative

To a solution of (1R,5S,6S)-6-[(1R)-1-hydroxyethyl]-2-oxo-1-methyl-1-carbapenam-3-carboxylic acid p-methoxybenzylester (1.45 g) in acetonitrile (15 ml) at −25° C., diphenylphosphoric acid chloride (0.953 ml) and diisopropylethylamine (0.872 ml) are successively added. The mixture is stirred at room temperature for 1 hour. To this mixture 2-sulfamoylaminomethyl-1-t-butoxycarbonyl-4-mercaptopyrrolidine (1.69 g) and diisopropylethylamine (0.945 ml) are added under ice cooling, and the mixture is stirred for 22 hours. The reaction mixture is mixed with 1N-hydrochloric acid (15 ml) and diluted with ethyl acetate. The organic layer is taken, washed with water, dried over sodium sulfate and concentrated. The residue is purified by column chromatography over 10% wet silica gel to give (1R,5S,6S)-6-[(1R)-1-hydroxyethyl]-2-[(3S,5S)-5-sulfamoylaminomethyl-1-t-butoxycarbonylpyrrolidin-3-yl]thio-1-methyl-1-carba-2-penem-3-carboxylic acid p-methoxybenzylester (1.61 g). Yield: 60%. Pale yellow foam.

NMR δ (CDCl$_3$) ppm: 1.25(d, J=7.2 Hz, 3H), 1.32(d, J=6.4 Hz, 3H), 1.47(s, 9H), 1.75 to 2.0(m, 1H), 2.4 to 2.65(m, 1H), 2.61(br s, 4H), 3.1 to 3.7 (m, 6H), 3.81(s, 3H), 3.75 to 4.25(m, 4H), 5.19, 5.25(ABq, J=12.1 Hz, 2H), 6.89(d, J=8.6 Hz, 2H), 7.39(d, J=8.6 Hz, 2H).

IR ν (CHCl$_3$) cm$^{-1}$: 3400, 3290, 1770, 1682.

Step 2. Deprotection

To a solution of (1R,5S,6S)-6-[(1R)-1-hydroxyethyl]-2-[(3S,5S)-5-sulfamoylaminomethyl-1-t-butoxycarbonylpyrrolidin-3-yl]thio-1-methyl-1-carba-2-penem-3-carboxylic acid p-methoxybenzylester (1.083 g) in a mixture of dichloromethane (16.5 ml), anisole (1.52 ml) and nitromethane (3.1 ml) at −60° C., a solution of 1.0M aluminum chloride in nitromethane (12.93 ml) is added dropwise. The mixture is stirred for 2 hours slowly warming up to −40° C. The reaction mixture is poured into a solution of sodium acetate (3.18 g) in water (24 ml), successively washed with ether and ether-petroleum ether, desalted and purified by styrene-divinylbenzene copolymer resin column chromatography, and lyophilized the objective fraction to give (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid (0.429 g). Yield: 67%. Pale yellow foam.

NMR δ (D$_2$O) ppm: 1.22(d, J=7.2 Hz, 3H), 1.27(d, J=6.3 Hz, 3H), 1.64 to 1.82(m, 1H), 2.62 to 2.80(m, 1H), 3.26 to 3.59(m, 5H), 3.63 to 3.76(m, 1H), 3.84 to 4.10 (m, 2H), 4.16 to 4.29(m, 2H).

IR ν (KBr) cm$^{-1}$: 3400, 1750.

MIC (γ/ml) : *Staphylococcus aureus* strain 3626: 25, *Streptococcus pyogenes* C203:<0.003.

EXAMPLE 2

Coupling 2 of a (3S,5S)-pyrrolidylthiocarbapenem derivative

Step 1. Preparation of a Protected pyrrolidylthiocarbapenem derivative

To a solution of (1R,5S,6S)-6-[(1R)-1-hydroxyethyl]-2-diphenoxyphosphonyloxy-1-methyl-1-carba- 2-penem-3-carboxylic acid p-nitrobenzylester (3.04 g: 5.12 mmole) in acetonitrile (30 ml) under ice cooling, a solution of diisopropylethylamine (1.16 ml: 1.3 eq.) and 2-sulfamoylaminomethyl-1-p-nitrobenzyloxycarbonyl-4-mercaptopyrrolidine (2.4 g: 1.2 eq.) in acetonitrile (20 ml) is added. The mixture is stirred under ice cooling for 140 minutes. The reaction mixture is diluted with ethyl acetate, successively washed with water and saturated brine, dried over magnesium sulfate and concentrated. The residue is purified by silica gel column chromatography (toluene: ethyl acetate) to give (1R,5S6S)-6-[(1R)-1-hydroxyethyl]-2-[(3S,5S)-5-sulfamoylaminomethyl-1-p-nitrobenzyloxycarbonylpyrrolidin-3-yl]thio-1-methyl-1-carba-2-penem-3-carboxylic acid p-nitrobenzylester (3.35 g). Yield: 89%.

NMR δ (CDCl$_3$) ppm: 1.28(d, J=7 Hz, 3H), 1.37(d, J=6 Hz, 3H), 4.68(s, 2H), 5.22, 5.50(ABq, J=14 Hz, 2H), 5.23(s, 2H), 7.52(d, J=9 Hz, 2H), 7.65 (d, J=9 Hz, 2H), 8.2(d, J=2.5 Hz, 2H), 8.26(d, J=2.5 Hz, 2H).

IR ν (CHCl$_3$) cm$^{-1}$: 1773, 1720, 1704.

Step 2. Deprotection

To a solution of (1R,5S,6S)-6-[(1R)-1-hydroxyethyl]-2-[(3S,5S)-5-sulfamoylaminomethyl-1-p-nitrobenzyloxycarbonylpyrrolidin-3-yl]thio-1-methyl-1-p-carba-2-penem-3-carboxylic acid p-nitrobenzylester (3 g) in a mixture of tetrahydrofuran (60 ml) and 0.1M-MES buffer (pH 7.0), 10% palladium on carbon (2 g) as a catalyst is added. The mixture is shaken under a stream of hydrogen at atmospheric pressure for 4 hours. The reaction mixture is filtered to remove the catalyst, washed with ethyl acetate to remove a neutral substance, and concentrated. The residual aqueous solution is purified by styrene-divinylbenzene copolymer resin column chromatography. The fraction eluting with 5 to 10% ethanol water is lyophilized to give (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid (1.42 g). Yield: 84.8%.

EXAMPLE 3

Synthesis of a (3S,5S)-pyrrolidylthiocarbapenem derivative

Step 1. Preparation of a protected pyrrolidylthiocarbapenem derivative

To a solution of (1R,5S,6S)-6-[(1R)-1-hydroxyethyl]-2-diphenoxyphosphonyloxy-1-methyl-1-carba-2-penem-3-carboxylic acid p-methoxybenzylester (1 mmole) in acetonitrile (10 ml) under ice cooling, diisopropylethylamine (1.2 mmole) and 2-p-methoxybenzyloxycarbonylsulfamoylaminomethyl-1-p-methoxybenzyloxycarbonyl-4-mercaptopyrrolidine (1 mmole) are added. The mixture is allowed to stand overnight. The reaction mixture is diluted with dichloromethane, successively washed with dilute hydrochloric acid, water, aqueous sodium hydrogen carbonate, and brine, dried and concentrated. The residue is purified by silica gel column chromatography to give (1R,5S,6S)-6-[(1R)-1-hydroxyethyl]-2-[(3S,5S)-5-p-methoxybenzyloxycarbonylsulfamoylaminomethyl-1-p-methoxybenzyloxy-carbonylpyrrolidin-3-yl]thio-1-methyl-1-carba-2-penem-3-carboxylic acid p-methoxybenzylester. Yield: 50 to 80%.

NMR δ (CDCl$_3$) ppm: 1.20(d, J=6.4 Hz, 3H), 1.34(d, J=6.1 Hz, 3H), 3.79(s,9H), 5.00 to 5.12(m, 4H), 5.23, 5.15(ABq, J=14.0 Hz, 2H).

IR ν (CHCl$_3$) cm$^{-1}$: 3390, 1770, 1740, 1693, 1610.

Step 2. Deprotection

To a solution of (1R,5S,6S)-6-[(1R)-1-hydroxyethyl]-2-[(3S,5S)-5-p-methoxybenzyloxycarbonylsulfamoylaminomethyl-1-p-methoxybenzyloxycarbonylpyrrolidin-3-yl]thio-1-methyl-1-carba-2-penem-3-carboxylic acid p-methoxybenzylester (1 mmole) in dichloromethane (20 ml) at −40° C., anisole (10 mmole) and a solution of 2M aluminum chloride in nitromethane (3 to 4 ml) are added. The mixture is stirred at the same temperature for 1 to 1.5 hours. The reaction mixture is poured into a solution of sodium acetate (19 to 25 mmole) in water (100 ml), washed with dichloromethane to remove a neutral substance. The aqueous layer is purified by styrene-divinylbenzene copolymer resin column chromatography. The objective eluate is lyophilized to give (1R,5S,6S)-6-[(1R)-1-hydroxyethyl]-2-[(3S,5S)-5-sulfamoylaminomethyl-1-pyrrolidin-3-yl]thio-1-methyl-1-carba-2-penem-3-carboxylic acid. Yield: 60 to 70%.

EXAMPLE 4

Synthesis of a (3S,5S)-pyrrolidylthiocarbapenem derivative

Step 1. Preparation of a protected pyrrolidylthiocarbapenem derivative

To a solution of (1R,5S,6S)-6-[(1R)-1-hydroxyethyl]-2-diphenoxyphosphonyloxy-1-methyl-1-carba-2-penem-3-carboxylic acid p-methoxybenzylester (700 mg) in acetonitrile (4 ml) at −30° C., a solution of diisopropylethylamine (182 μl) and 1-p-methoxybenzyloxycarbonyl-4-mercapto-2-(N-p-methoxybenzyloxycarbonyl-N-methylaminosulfonylaminomethyl)pyrrolidine (401 mg) in acetonitrile (3 ml) is added. The mixture is stirred under ice cooling for 90 minutes. The reaction mixture is poured into a mixture of ethyl acetate and dilute hydrochloric acid. The ethyl acetate layer is taken, successively washed with water, aqueous sodium hydrogen carbonate, and brine, dried over magnesium sulfate, and concentrated in vacuo. The residue is purified by silica gel column chromatography (toluene: ethyl acetate=1:2) to give (1R,5S,6S)-6-[(1R)-1-hydroxyethyl]-2-[(3S,5S)-1-p-methoxybenzyloxycarbonyl-5-(N-p-methoxybenzyloxycarbonyl-N-methylaminosulfonylaminomethyl)pyrrolidin-3-yl]thio-1-methyl-1-carba-2-penem-3-carboxylic acid p-methoxybenzylester (512 mg).

NMR δ (CDCl$_3$) ppm: 1.22(d, J=7.0 Hz, 3H), 1.34(d, J=6.4 Hz, 3H), 1.6 to 1.9(m, 1H), 2.25 to 2.5(m, 1H), 3 to 3.6(m, 7H), 3.778(s, 3H), 3.783(s, 3H), 3.788(s, 3H), 5.05(s, 2H), 5.13(s, 2H), 5.2(ABq, J=12 Hz, 2H), 6.3 to 6.5(m, 1H), 6.8 to 7.0(m, 6H), 7.2 to 7.4(m, 6H).

IR ν (CHCl$_3$) cm$^{-1}$: 1767, 1697.

Step 2. Deprotection

To a solution of (1R,5S,6S)-6-[(1R)-1-hydroxyethyl]-2-[(3S,5S)-1-p-methoxybenzyloxycarbonyl-5-(N-p-methoxybenzyloxycarbonyl-N-methylaminosulfonylaminomethyl)pyrrolidin-3-yl]thio-1-methyl-1-carba-2-penem-3-carboxylic acid p-methoxybenzylester (610 mg) in a mixture of dichloromethane (6 ml), nitromethane (2 ml) and anisole (4 ml) stirring at −40° C., 2M-solution of aluminum chloride in nitromethane (2.6 ml: 7.5 equivalents) is added. The mixture is stirred at −35°±5° C. for 1 hour and 30 minutes. The reaction mixture is poured into a mixture of sodium acetate (1.34 g), water (20 ml) and dichloromethane (20 ml). The aqueous layer is taken, subjected to a styrene-divinylbenzene copolymer resin column chromatography, and the fraction eluting with 8% ethanol is lyophilized to give (1R,5S,6S)-6-[(1R)-1-hydroxyethyl]-2-[(3S,5S)-5-N-methylaminosulfonylamino-methylpyrrolidin-3-yl]thio-1-methyl-1-carba-2-penem-3-carboxylic acid (206 mg). Yield: 68.6%.

NMR δ (CDCl$_3$) ppm: 1.22(d, J=7.0 Hz, 3H), 1.27(d, J=6.4 Hz, 3H), 1.5 to 1.8(m, 1H), 2.63(s, 3H), 2.6 to 2.8(m, 1H), 3.1 to 3.6(m, 5H), 3.65, 3.72(dd, J=6.6 Hz, J=7.6 Hz, 1H), 3.8 to 4.4(m, 4H).

IR ν (CHCl$_3$) cm$^{-1}$: 1750, 1585.

MIC (γ/ml) : *Staphylococcus aureus* strain 3626: 25, *Streptococcus pyogenes* C203:<0.003.

EXAMPLE 5

Synthesis of a (3S,5S)-pyrrolidylthiocarbapenem derivative

Step 1. Preparation of a protected pyrrolidylthiocarbapenem derivative

To a solution of (1R,5S,6S)-6-[(1R)-1-hydroxyethyl]-2-diphenoxyphosphonyloxy-1-methyl-1-carba-2-penem-3-carboxylic acid p-methoxybenzylester (1 mmole) in acetonitrile (10 ml) under ice cooling, di-isopropylethylamine (1.2 mmole) and 2-N,N-dimethylsulfamoylaminomethyl-1-p-methoxybenzyloxycarbonyl-4-mercaptopyrrolidine (1 mmole) are added. The mixture is allowed to stand overnight. The reaction mixture is diluted with dichloromethane, successively washed with dilute hydrochloric acid and water, dried, and concentrated. The residue is purified by silica gel column chromatography to give (1R,5S,6S)-6-[(1R)-1-hydroxyethyl]-2-[(3S,5S)-5-N,N-dimethylsulfamoylaminomethyl-1-p-methoxybenzyloxycarbonylpyrrolidin-3-yl]thio-1-methyl-1-carba-2-penem-3-carboxylic acid p-methoxybenzylester. Yield: 50 to 80%.

NMR δ (CDCl$_3$) ppm: 1.22(d, J=7.2 Hz, 3H), 1.34(d, J=6.2 Hz, 3H), 2.76(S,6H), 3.79(s, 3H), 3.81(s, 3H), 5.06(s, 2H), 5.24, 5.18(ABq, a=12 Hz, 2H).

IR ν (CHCl$_3$) cm$^{-1}$: 3390, 1770, 1725, 1690, 1610.

Step 2. Deprotection

A solution of (1R,5S,6S)-6-[(1R)-1-hydroxyethyl]-2-[(3S,5S)-5-N,N-dimethylsulfamoylaminomethyl-1-p-methoxybenzyloxycarbonylpyrrolidin-3-yl]thio-1-methyl-1-carba-2-penem-3-carboxylic acid p-methoxybenzylester (1 mmole) in dichloromethane (20 ml) is cooled to −40° C. Anisole (10 mmole) and a solution of 2M aluminum chloride in nitromethane (3 to 4 ml) are added thereto, and the mixture is stirred at the same temperature for 1 to 1.5 hours. The reaction mixture is poured into a solution of sodium acetate (19 to 25 mmole) in water (100 ml), and washed with dichloromethane to remove a neutral material. The aqueous layer is purified by styrene-divinylbenzene copolymer resin column chromatography and the objective eluate is lyophilized to give (1R,5S6S)-6-[(1R)-1-hydroxyethyl]-2-[(3S,5S)-5-N,N-dimethylsulfamoylaminomethylpyrrolidin-3-yl] thio-1-methyl-1-carba-2-penem-3-carboxylic acid. Yield: 60 to 70%.

NMR δ (D$_2$O) ppm: 1.2(d, J=7.4 Hz, 3H), 1.28(d, J=6.4 Hz, 3H), 1.65 to 1.80(m, 1H), 2.65 to 2.80(m, 1H), 2.81(s, 6H), 3.29 to 3.55(m, 5H), 3.65 to 3.75(m, 1H), 3.80 to 4.10(m, 2H), 4.16 to 4.30(m, 2H).

IR ν (KBr) cm$^{-1}$: 3400, 1750.

MIC (γ/ml) : *Staphylococcus aureus* strain 3626: 5, *Streptococcus pyogenes* C203:<0.003.

EXAMPLE 6. Synthesis of a (3S,5S)-pyrrolidylthiocarbapenem derivative

Step 1. Preparation of a protected pyrrolidylthiocarbapenem derivative

To a solution of (1R,5S,6S)-2-diphenoxyphosphonyloxy-6-[(1R)-1-hydroxyethyl]-1-methyl-1-carba-2-penem-3-carboxylic acid diphenylmethylester (6.88 g: 11 mmole) in dichloromethane (70 ml) under ice cooling, trimethylchlorosilane (1.81 ml: 14.3 mmole) and triethylamine (1.99 ml: 14.3 mmole) are added. The mixture is stirred for 25 minutes. The reaction mixture is poured into aqueous sodium hydrogen carbonate. The organic layer is taken, washed with water and brine, dried over sodium sulfate, and concentrated under reduced pressure. The residue containing the product, (1R,5S,6S)-2-diphenoxyphosphonyloxy-1-methyl-6-[(1R)-1-trimethylsilyloxyethyl]-1-carba-2-penem-3-carboxylic acid diphenylmethylester is dissolved in acetonitrile (70 ml), and (2S,4S)-1-t-butoxycarbonyl-2-(N-t-butoxycarbonyl-N-sulfamoylamino)methyl-4-mercaptopyrrolidine (5.43 g: 13.2 mmole) and diisopropylethylamine (2.30 g: 13.2 mmole) are added thereto under ice cooling. The obtained mixture is stirred for 4.5 hours. To the reaction mixture containing the product, (1R,5S,6S)-2-[(3S,5S)-1t-butoxycarbonyl-5-(N-t-butoxycarbonyl-N-sulfamoylamino)methylpyrrolidin-3-yl]thio-1-methyl-6-[(1R)-1-trimethylsilyloxyethyl]-1-carba-2-penem-3-carboxylic acid diphenylmethylester, 1N-hydrochloric acid (5.5 ml) is added, and the mixture is stirred for 20 minutes, diluted with ethyl acetate(150 ml), wad the mixture is poured into ice water. The organic layer is taken, successively washed with aqueous sodium hydrogen carbonate, water, and brine, dried over sodium sulfate, and concentrated under reduced pressure. The residue is recrystallized from toluene to give (1R,5S,6S)-2-[(3S,5S)-1-t-butoxycarbonyl-5-(N-t-butoxycarbonyl-N-sulfamoylamino)-methylpyrrolidin-3-yl]thio-6-[(1R)-1-hydroxyethyl]-1-methyl-1-carba-2-penem-3-carboxylic acid diphenylmethylester (7.53 g). Yield: 87%. Colorless crystals. mp.163° to 164° C.

NMR δ (CDCl$_3$) ppm: 1.27(d, J=7.2 Hz, 3H), 1.39(s, 9H), 1.42(s, 9H), 2.45 to 2.65(m, 1H), 3.1 to 3.35(m, 2H), 3.28(dd, J=7.2 Hz, J=2.6 Hz, 1H),3.5 to 3.77(m, 2H), 3.9 to 4.15(m, 2H), 4.26(dd, J=7.0 Hz, J=2.6 Hz, 1H), 4.2 to 4.37(m, 1H), 4.45 to 4.66(m, 1H), 6.07(s, 2H), 6.95(s, 1H), 7.2 to 7.6(m, 10H).

IR ν (CHCl$_3$) cm$^{-1}$: 3385, 3230, 1778, 1715, 1685.

Elemental Analysis (C$_{38}$H$_{50}$N$_4$O$_{10}$S$_2$) Calcd.: C, 57.99; H, 6.40; N, 7.12; S, 8.15. Found: C, 57.87; H, 6.46; N, 6.99; S, 7.93.

Step 2. Deprotection

To a solution of aluminum chloride (3.20 g: 24 mmole) in a mixture of anisole (24 ml) and dichloromethane (24 ml) at −40° C., a solution of (1R,5S,6S)-2-[(3S,5S)-1-t-butoxycarbonyl-5-(N-t-butoxycarbonyl-N-sulfamoyl-amino)methylpyrrolidin-3-yl]thio-6-[(1R)-1-hydroxy-ethyl]-1-methyl-1-carba-2-penem-3-carboxylic acid diphenylmethylester (2.36 g: 3 mmole) in dichloromethane (12 ml) is dropwise and gradually added. The mixture is vigorously stirred at −25° to −30° C. for 3.5 hours. The reaction mixture is poured into a solution of sodium acetate (5.91 g: 72mmole) in water (48 ml). The aqueous layer is taken, washed with dichloromethane, concentrated in vacuo to remove remaining organic solvent and subjected to styrene-divinylbenzene copolymer resin column chromatography. The fraction eluting with methanol-water (1:9) is lyophillized to give (1R,5S,6S)-6-[(1R)-1-hydroxyethyl]-2-[(3S,5S)-5-sulfamidomethylpyrrolidin-3-yl]thio-1-methyl-1-carba-2-penem-3-carboxylic acids. (910 mg). Yield: 72%. Colorless foam.

NMR δ (D$_2$O) ppm: 1.22(d, J=7.2 Hz, 3H), 1.27(d, J=6.3 Hz, 3H), 1.64 to 1.82(m, 1H), 2.62 to 2.80(m, 1H), 3.26 to 3.59(m, 5H), 3.63 to 3.76(m, 1H), 3.84 to 4.10(m, 2H), 4.16 to 4.29(m, 2H).

IR ν (KBr) cm$^{-1}$: 3400, 1750.

MIC (γ/ml) : Staphylococcus aureus 3626: 25. Blood level: mice i.v., after 15 min. (γ/ml): 9.8. Urinary recovery: mice i.v., (%): 36.3.

EXAMPLE 7

Synthesis of a (3S,5S)-pyrrolidylthiocarbapenem derivative

Step 1. Preparation of a protected pyrrolidylthiocarbapenem derivative

To a solution of (1R,5S,6S)-6-[(1R)-1-hydroxyethyl]-1-methyl-2-oxo-1-carbapenam-3-carboxylic acid p-methoxybenzylester (277 mg) in acetonitrile (4 ml) under ice cooling, diphenylphosphoric acid chloride (198 µl) and diisopropylethylamine (166 µl) are successively added. The mixture is stirred at room temperature for 1 hour. To the reaction mixture containing the product, (1R, 5S,6S)-2-diphenoxyphosphonyloxy-6-[(1R)-1-hydroxyethyl]-1-methyl-1-carba-2-penem- 3-carboxylic acid p-methoxybenzylester, (2S,4S)-2-(2-hydroxyethyl)sulfamoylaminomethyl-1-p-methoxybenzyloxy-carbonyl-4-mercaptopyrrolidine (344 mg) and diisopropylethylamine (166 µl) are added under ice cooling, and the mixture is stirred at the same temperature for 2 hours. The reaction mixture is diluted with ethyl acetate, successively washed with water, dilute hydrochloric acid, water, aqueous sodium hydrogen carbonate and water, dried over magnesium sulfate, and concentrated. The residue is purified by silica gel column chromatography to give (1R,5S,6S)-6-[(1R)-1-hydroxyethyl]-2-[(3S,5S)-5-(2-hydroxyethyl) sulfamoylaminomethyl-1-p-methoxybenzyloxycarbonylpyrrolidin-3-yl]thio-1-methyl-1-carba-2-penem-3-carboxylic acid p-methoxybenzylester (156 mg). Yield: 26%.

NMR δ (CDCl$_3$) ppm: 1.22(d, J=7.0 Hz, 3H), 1.34(d, J=6.2 Hz, 3H), 3.79(s, 3H), 3.80(s, 3H), 5.05(s, 2H), 5.17, 5.24(ABq, J=12.2 Hz, 2H).

IR ν (CHCl$_3$) cm$^{-1}$: 1775, 1690.

Step 2. Deprotection

To a solution of (1R,5S,6S)-6-[(1R)-1-hydroxyethyl]-2-[(3S,5S)-5-(2-hydroxyethyl)sulfamoylaminomethyl-1-p-methoxybenzyloxycarbonylpyrrolidin-3-yl]thio-1-methyl-1-carba-2-penem-3-carboxylic acid p-methoxybenzyl ester (148 mg) in a mixture of dichloromethane (3 ml) and nitromethane (750 µl) in a nitrogen atmosphere at −40° C., a solution of 1.0M aluminum chloride in nitromethane (1.8 ml) and anisole (258 µl) is added. The mixture is stirred at the same temperature for 1.5 hours. The reaction mixture is poured into a solution of sodium acetate (454 mg) in water (8 ml) and washed with an ether-hexane mixture. The aqueous layer is concentrated in vacuo to 4 ml, and purified by styrene-divinylbenzene copolymer resin column chromatography to give (1R,5S,6S)-6-[(1R)-1-hydroxyethyl]-2-[(3S,5S)-5-(2-hydroxyethyl)sulfamoylaminomethyl-pyrrolidin-3-yl]thio-1-methyl-1-carba-2-penem-3-carboxylic acid (42 mg). Yield: 46%.

NMR δ (D$_2$O) ppm: 1.21(d, J=7.4 Hz, 3H), 1.28(d, J=6.4 Hz, 3H), 1.66 to 1.81(m, 1H), 2.66 to 2.81(m, 1H), 3.15(t, J=5.6 Hz, 2H), 3.32 to 3.54(m, 5H), 3.65 to 3.75(m, 3H), 3.87 to 4.07(m, 2H), 4.18 to 4.27(m, 2H).

IR ν (KBr) cm$^{-1}$: 3400, 1750. Blood level: mice i.v., after 15 min (γ/ml): 29.3.

EXAMPLE 8

Synthesis of a (3S,5S)-pyrrolidylthiocarbapenem derivative

Step 1. Preparation of a protected pyrrolidylthiocarbapenem derivative

To a solution of (1R,5S,6S)-2-diphenoxyphosphonyloxy-6-[(1R)-1-hydroxyethyl]-1-methyl-1-carba-2-penem-3-carboxylic acid p-methoxybenzylester (456 mg) in acetonitrile (3 ml) under ice cooling, diisopropylethylamine (165 µl) and (2S,4S)-2-(1,1-dioxo-2-p-methoxybenzyloxycarbonyl-1,2,5-thiadiazolidin-5-yl) methyl-4-mercapto-1-p-methoxybenzyloxycarbonylpyrrolidine (445 mg) are added. The mixture is allowed to stand at 0° C. overnight. The reaction mixture is diluted with ethyl acetate, successively washed with water, dilute hydrochloric acid and water, dried over magnesium sulfate, and concentrated in vacuo. The residue is purified by silica gel chromatography to give (1R,5S,6S)-2-[(3S,5S)-5-(1,1-dioxo-2-p-methoxybenzyloxycarbonyl-1,2,5-thiadiazolidin-5-yl)-methyloxybenzyloxycarbonylpyrrolidin- 3-yl]thio-6-[(1R)-1-hydroxyethyl]-1-methyl-1-carba-2-penem-3-carboxylic acid p-methoxybenzylester (510 mg). Yield: 72%.

NMR δ (CDCl$_3$) ppm: 1.22(d, J=7.4 Hz, 3H), 1.34(d, J=6.2 Hz, 3H), 5.04(s, 2H), 5.23(s, 2H), 5.18, 5.24(ABq, J=11.9 Hz, 2H).

IR ν (CHCl₃) cm⁻¹: 1773, 1735, 1700.

Step 2 Deprotection

To a solution of (1R,5S,6S)-2-[(3S,5S)-5-(1,1-dioxo-2-p-methoxybenzyloxycarbonyl-1,2,5-thiadi-azolidin-5-yl)methyl-1-p-methoxybenzyloxycarbonylpyrrolidin-3-yl]thio-6-[(1R)-1-hydroxyethyl]-1-methyl-1-carba-2-penem-3-carboxylic acid p-methoxybenzylester (500 mg) in a mixture of dichloromethane (8 ml) and nitromethane (3 ml) in a nitrogen atmosphere at −40° C., anisole (729 μl) and a solution (5.03 ml) of 1.0M aluminum chloride in nitromethane are added. The mixture is stirred at the same temperature for 1.5 hours. The reaction mixture is poured into a solution of sodium acetate (1.28 g) in water (50 ml), then aqueous layer is taken, and washed with an ether-hexane mixture. The aqueous layer is concentrated under reduced pressure to about 15 ml, and is purified by styrene-divinylbenzene copolymer resin column chromatography to give (1R,5S,6S)-2-[(3S,5S)-5-(1,1-dioxo-1,2,5-thiadiazolidin-5-yl)methylpyrrolidin-3-yl]thio-6-[(1R)-1-hydroxyethyl]-1-methyl-1-carba-2-penem-3-carboxylic acid (180 mg). Yield: 72%.

NMR δ (D₂O) ppm: 1.21(d, J=7.4 Hz, 3H), 1.28(d, J=6.4 Hz, 3H), 1.68 to 1.84(m, 1H), 2.71 to 2.85(m, 1H), 3.28 to 3.77(m, 10H), 3.94 to 4.12(m, 2H), 4.17 to 4.31(m, 2H).

IR ν (KBr) cm⁻¹: 3400, 1750.

MIC (γ/ml): Staphylococcus aureus strain 3626: 25.
Blood level: mice i.v., after 15 min (γ/ml): 31.8.

EXAMPLE 9

Synthesis of a (3S,5S)-pyrrolidylthiocarbapenem derivative

Step 1. Preparation of a protected pyrrolidylthiocarbapenem derivative

To a solution of (1R,5S,6S)-2-diphenoxyphosphonyloxy-6-[(1R)-1-hydroxyethyl]-1-methyl-1-carba-2-penem-3-carboxylic acid p-methoxybenzyl ester (638 mg) in acetonitrile (6 ml) under ice cooling, diisopropylethylamine (230 μl) and (2S,4S)-2-(1,1-dioxo-2-p-methoxybenzyloxycarbonyl-3,4,5,6-tetrahydro-1,2,6-thiadiazin-6-yl)methyl-4-mercapto-1-p-methoxybenzyloxycarbonylpyrrolidine (700 mg) are added. The mixture is stirred at 5° C. for 2 hours and at room temperature for 1 hour. The reaction mixture is diluted with ethyl acetate, successively washed with water, dilute hydrochloric acid, water, aqueous sodium hydrogen carbonate and water, dried over magnesium sulfate, and concentrated in vacuo. The residue is purified by silica gel chromatography to give (1R,5S,6S)-2-[(3S,5S)-5-(1,1-dioxo-2-p-methoxybenzyloxycarbonyl-3,4,5,6-tetrahydro-1,2,6-thiadiazin-6-yl)methyl-1-p-methoxybenzyloxycarbonylpyrrolidin-3-yl]thio-6-[(1R)-1-hydroxyethyl]-1-methyl-1-carba-2-penem-3-carboxylic acid p-methoxybenzyl ester (640 mg). Yield: 64%.

NMR δ (CDCl₃) ppm: 1.22(d, J=7.4 Hz, 3H), 1.34(d, J=6.4 Hz, 3H), 5.04(s, 2H), 5.17, 5.25(ABq, J=12.3 Hz, 2H), 5.19(s, 2H).

IR (CHCl₃) cm⁻¹: 1700, 1770.

Step 2. Deprotection

To a solution of (1R,5S,6S)-2-[(3S,5S)-5-(1,1-dioxo-2-p-methoxybenzyloxycarbonyl-3,4,5,6-tetrahydro-1,2,6-thiadiazin-6-yl)methyl-1-p-methoxybenzyloxycarbonylpyrrolidin-3-yl]thio-6-[(1R)-1-hydroxyethyl]-1-methyl-1-carba-2-penem-3-carboxylic acid p-methoxybenzylester (600 mg) in a mixture of dichloromethane (9 ml) and nitromethane (3.5 ml) in a nitrogen atmosphere at −40° C., anisole (861 μl) and a solution of 1.0M aluminum chloride in nitromethane (5.94 ml) are added. The mixture is stirred at the same temperature for 1.5 hours. The reaction mixture is poured into a solution of sodium acetate (1.52 g) in water (50 ml), and washed with a mixture of ether and hexane. The aqueous layer is concentrated in vacuo to about 15 ml, and the mixture is purified by styrene-divinylbenzene copolymer resin column chromatography to give (1R,5S,6S)-2-[(3S,5S)-5-(1,1-dioxo-3,4,5,6-tetrahydro-1,2,6-thiadiazin-6-yl)methylpyrrolidin-3-yl]-thio-6-[(1R)-1-hydroxy-ethyl]-1-methyl-1-carba-2-penem-3-carboxylic acid (190 mg). Yield: 63%.

NMR δ (D₂O) ppm: 1.20(d, J=7.2 Hz, 3H), 1.27(d, J=6.4 Hz, 3H), 1.65 to 1.80(m, 3H), 2.65 to 2.80(m, 1H), 3.27 to 3.56(m, 9H), 3.64 to 3.74(m, 1H), 3.91 to 4.10(m, 2H), 4.15 to 4.30(m, 2H).

IR ν (KBr) cm⁻¹: 3400, 1750.

MIC (γ/ml): Staphylococcus aureus strain 3626: 25.
Blood level: mice i.v., after 15 min. (γ/ml): 28.4.

EXAMPLES 10 to 12

Synthesis of (3R,5R), (3R,5S) and (3S,5R) pyrrolidylthiocarbapenem derivatives

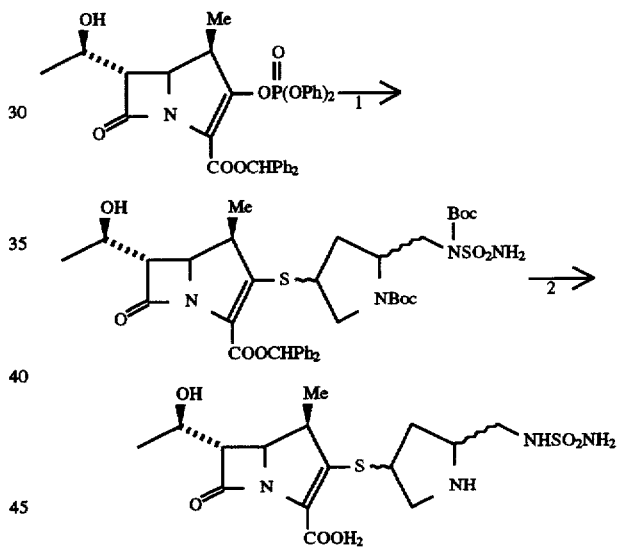

Step 1. Preparation of a protected pyrrolidylthiocarbapenem derivatives

To a solution of (1R,5S,6S)-2-diphenoxyphosphonyloxy-6-[(1R)-1-hydroxyethyl]-1-methyl-1-carba-2-penem-3-carboxylic acid diphenylmethyl ester (i.e., a substrate) and 1-t-butoxycarbonyl-2-(N-t-butoxycarbonyl-N-sulfamoylamino)methyl-4-mercaptopyrrolidine (Pyld) in acetonitrile (MeCN) under ice cooling, diisopropylethylamine (HNPr-i) is added dropwise. The mixture is stirred to react under a condition shown in Table 4. The reaction mixture is diluted with ethyl acetate, and ice water is added thereto. The organic layer is taken, successively washed with water and saturated brine, dried over magnesium sulfate, and concentrated in vacuo. The residue is purified by silica gel chromatography to give (1R,5S,6S)-2-[1-t-butoxycarbonyl-5-(N-t-butoxycarbonyl-N-sulfamoylamino)methylpyrrolidin-3-yl]-thio-6-[(1R)-1-hydroxyethyl]-1-methyl-1-carba-2-penem-3-carboxylic acid diphenylmethyl ester.

TABLE 4

| Example | Configuration of Pyld[i] | Pyld[j] equiv. | HNPr-i[j] equiv. | MeCN[k] vol. | Temp. | Time min. | Yield % |
|---|---|---|---|---|---|---|---|
| Ex. 10 | 3R5R | 1.17 | 1.30 | 7 fold | ice cooling | 240 | 86 |
| Ex. 11 | 3R5S | 1.20 | 1.30 | 7 fold | ice cooling | 120 | 88 |
| Ex. 12 | 3S5R | 1.14 | 1.27 | 7 fold | ice cooling | 270 | 73 |

[i]Configuration of a pyrrolidine ring
[j]Molar ratio to the substrate
[k]The volume (ml) of the solvent to the weight (g) of the substrate Physical properties of the products
(3R,5R) Isomer:
NMR δ (CDCl₃) ppm: 1.26(d, J=7.2 Hz, 3H), 1.39(d, J=6.2 Hz, 3H), 1.43 (s, 9H), 1.51(s, 9H), 2.5(m, 1H), 3.1 to 3.9(m, 6H), 4.0 to 4.7(m, 4H), 6.1(m, 1H), 6.98(s, 1H), 7.1 to 7.6(m, 10H).
IR ν (KBr) cm⁻¹: 3400, 3240, 1770, 1710, 1670.
(3S,5R) Isomer:
NMR δ (CDCl₃) ppm: 1.28(d J=7.0 Hz, 3H), 1.36(s 9H) 1.40(d, J=6.2 Hz, 3H), 1.52(s, 9H), 2.0(m, 1H), 3.2 to 3.9(m, 7H), 4.2 to 4.4 (m, 2H), 4.4 to 4.6(m, 1H), 6.01(s, 2H), 6.94(s, 1H), 7.1 to 7.6(m, 10H).
IR ν (KBr) cm⁻¹: 3400, 3240, 1772, 1708, 1682.
(3R,5S) Isomer:
NMR δ (CDCl₃) ppm: 1.76(d, J=7.2 Hz, 3H), 1.3 to 1.5(m, 12H), 1.52(s, 9H), 1.9 to 2.1(m, 1H), 3.2 to 3.9(m, 7H), 4.1 to 4.4(m, 2H), 4.4 to 4.6(m, 1H), 6.04(s, 2H), 6.94(s, 1H), 7.1 to 7.6(m, 10H).
IR ν (KBr) cm⁻¹: 3420, 1770, 1710.

Step 2. Deprotection
A solution of (1R,5S,6S)-2-[1-t-butoxycarbonyl-5-(N-t-butoxycarbonyl-N-sulfamoylamino)methylpyrrolidin-3-yl]thio-6-[(1R)-1-hydroxyethyl]-1-methyl-1-carba-2-penem-3-carboxylic acid diphenylmethyl ester (i.e., a substrate) in dichloromethane (DCM) is added dropwise in a nitrogen atmosphere into a solution of aluminum chloride (AlCl₃) in a mixture of dichloromethane (DCM) and anisole (PhOMe). The mixture is stirred to react under the condition shown in Table 5. To the reaction mixture, aqueous sodium acetate is added. The aqueous layer is taken, washed with dichloromethane, and purified by column chromatography over styrenedivinylbenzene copolymer resin to give (1R,5S,6S)-6-[(1R)-1-hydroxyethyl]-2-[5-sulfamidomethylpyrrolidin-3-yl]thio-1-methyl-1-carba-2-penem-3-carboxylic acid.

TABLE 5

| Example | Configuration[l] of Pyld | AlCl₃[m] equiv. | DCM[n] vol. (fold) | PhOMe[n] vol. (fold) | Temp. °C. | Time min. | Yield % |
|---|---|---|---|---|---|---|---|
| Ex. 10 | 3R5R | 8.0 | 16 | 10 | −30 | 300 | 86 |
| Ex. 11 | 3R5S | 8.0 | 17 | 10 | −30 | 150 | 88 |
| Ex. 12 | 3S5R | 8.0 | 17 | 10 | −30 | 150 | 73 |

[l]Configuration of a pyrrolidine ring
[m]Molar ratio to the substrate
[n]The volume (ml) of the solvent to the weight (g) of the substrate Physical properties of the products
(3R,5R) Isomer:
NMR δ (D₂O) ppm: 1.18(d, J=7.2 Hz, 3H), 1.27(d, J=6.2 Hz, 3H), 1.9(m, 1H), 2.7(m, 1H), 3.2 to 3.6(m, 5H), 3.6 to 3.8(m, 1H), 3.8 to 4.1(m, 2H), 4.2(m, 2H).
IR ν (KBr) cm⁻¹: 3360, 1750.
(3S,5R) Isomer:
NMR δ (CD₃SOCD₃) ppm: 1.09(d, J=7.0 Hz, 3H), 1.14(d, J=6.2 Hz, 3H), 1.7 to 2.0(m, 1H), 1.9 to 2.2(m, 1H), 2.9(m, 1H), 3.0 to 3.3(m, 4H), 3.3 to 3.6(m, 1H), 3.6 to 3.8(m, 2H), 3.9(m, 1H), 4.1(m, 1H).
IR ν (KBr) cm⁻¹: 3340, 1765, 1740, 1620, 1575, 1548.
(3R,5S) Isomer:
NMR δ (D₂O) ppm: 0.86(d, J=7.4 Hz, 3H), 0.93(d, J=6.4 Hz, 3H), 2.43(d,J=6.4 Hz, 3H), 1.90(dd, J=9.0 Hz, J=4.4 Hz, 2H), 2.9 to 3.3(m, 5H), 3.48(dd, J=13.2 Hz, J=7.2 Hz, 1H), 3.7 to 3.8(m, 2H), 3.8 to 4.0 (m, 2H), 4.47 DHO.
IR ν (KBr) cm⁻¹: 3400, 1750, 1585.

EXAMPLE 13

Synthesis of a (3S,5S)-pyrrolidylthiocarbapenem derivative using a monoallyloxycarbonyl intermediate

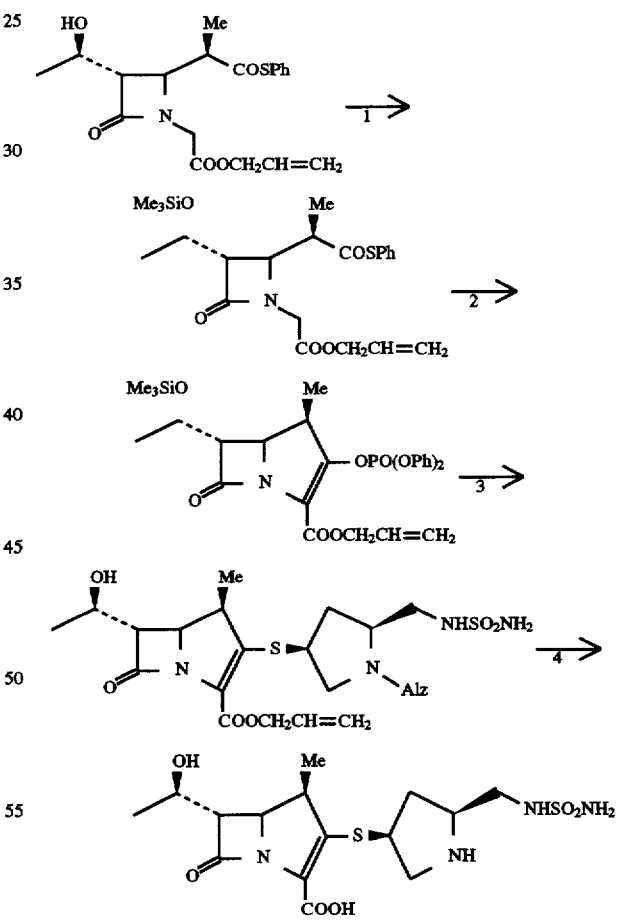

Step 1. Preparation of a trimethylsilyl compound
To a solution of (3S,4S)-3-[(1R)-1-hydroxyethyl]-4-[(1R)-1-phenylthiocarbonylethyl]-1-allyloxycarbonylmethyl-2-azetidinone (5.04 g: 13.35 mmole) in toluene (40 ml) under ice cooling, pyridine (1.51 ml: 18.69 mmole) is added and trimethylchlorosilane (2.26 ml: 17.36 mmole) is added dropwise. The mixture is stirred at room temperature for 1.5 hours. Water (80 ml) is added to the reaction mixture, and aqueous layer is extracted with toluene. The extract and the organic layer are combined, washed with water (2 times) and saturated brine, dried over magnesium sulfate, and concentrated in vacuo to give crude (3S,4S)-3-[(1R)-1-trimethylsilyloxyethyl]-4-[(1R)-1-phenylthiocarbonylethyl]-1-allyloxycarbonylmethyl-2-azetidinone (5.614 g) as oily residue. Yield: 94%.

Step 2. Ring closure

To a solution of the crude (3S,4S)-3-[(1R)-1-trimethylsilyloxyethyl]-4-[(1R)-1-phenylthiocarbonylethyl]-1-allyloxycarbonylmethyl-2-azetidinone (5.60 g: 12.454 mmole) obtained in Step 1 in tetrahydrofuran (62 ml) at –60° C., a solution of 1M-potassium t-butoxide (24.9 mmole) in tetrahydrofuran (24.9 ml) is added dropwise. The mixture is stirred for 10 minutes. After adding iodomethane (0.48 ml: 14.94 mmole) and stirring at the same temperature for 20 minutes, diphenylphosphoryl chloride (2.73 ml: 12.45 mmole) is added thereto. After allowing to warm to an ice water temperature over 1 hour, the reaction mixture is diluted with toluene (120 ml) and water (120 ml). The aqueous layer is extracted with toluene. The extract and the organic layer are combined, successively washed with water (2 times), aqueous sodium hydrogen carbonate, and saturated brine, dried over magnesium sulfate, and concentrated in vacuo to give crude (1R,5S,6S)-2-diphenoxyphospholyloxy-6-[(1R)-1-trimethylsilyloxyethyl]-1-methyl-1-carba-2-penem-3-carboxylic acid allyl ester (3.795 g) as oily residue. Yield: 104%.

IR v (CHCl$_3$) cm$^{-1}$: 3008, 1778, 1722, 1636, 1589, 1489.

NMR δ (CDCl$_3$) ppm: 0.12(9H, s), 1.19(3H, d, J=7.2 Hz), 1.25(3H, d, J=6.2 Hz), 3.24(1H, dd, J=3.0 Hz, J=6.8 Hz), 3.3 to 3.6(1H, m), 4.11(1H, dd, J=3.0 Hz, J=10.2 Hz), 4.1 to 4.3(1H, m), 4.6 to 4.7(2H, m), 5.1 to 5.5(2H, m), 5.7 to 6.0(1H, m), 7.1 to 7.5(10H, m).

Step 3. Preparation of a protected pyrrolidylthiocarbapenem derivative

To a solution of crude (1R,5S,6S)-2-diphenoxyphospholyloxy-6-[(1R)-1-trimethylsilyloxyethyl]-1-methyl-1-carba-2-penem-3-carboxylic acid allyl ester (2.56 g: 4.2 mmole) obtained in Step 2 and (2S,4S)-1-allyloxycarbonyl-2-(N-sulfamoylamino)methyl-4-mercaptopyrrolidine (1.48 g: 5.0 mmole) in acetonitrile (13 ml) under ice cooling, diisopropylethylamine (0.95 ml: 5.46 mmole) is added dropwise, and the mixture is stirred at the same temperature for 7.5 hours. The reaction mixture is acidified with 1N-hydrochloric acid (6.3 ml), stirred at the same temperature for 30 minutes, and ethyl acetate (80 ml) and ice water (80 ml) are added thereto. The organic layer is taken, successively washed with water and saturated brine, dried over magnesium sulfate and concentrated in vacuo. The residue is purified by silica gel chromatography (toluene-ethyl acetate) to give (1R,5S,6S)-2-[(3S,5S)-1-allyloxycarbonyl-5-(N-sulfamoylamino)methylpyrrolidin-3-yl]thio-6-[(1R)-1-hydroxyethyl]-1-methyl-1-carba-2-penem-3-carboxylic acid allyl ester (1.63 g). Yield: 71%.

IR v (CHCl$_3$) cm$^{-1}$: 1772, 1691, 1410.

$^1$HNMR δ (CDCl$_3$) ppm: 1.26(3H, d, J=7.0 Hz), 1.35(3H, d, J=6.0 Hz), 1.7 to 2.7(3H, m), 3.1 to 3.5(5H, m), 3.5 to 3.8 (1H, m), 3.9 to 4.4(4H, m), 4.5 to 4.9(4H, m), 5.0 to 5.5(5H, m), 5.8 to 6.1(2H, m).

Step 4. Deprotection

To a solution of (1R, 5S,6S)-2-[(3S,5S)-1-allyloxycarbonyl-5-(N-sulfamoylamino) methylpyrrolidin-3-yl]thio-6-[(1R)-1-hydroxyethyl]-1-methyl-1-carba-2-penem-3-carboxylic acid allyl ester (379 mg: 0.695 mmole) in acetone (14 ml), triphenylphosphine (55 mg: 0.21 mmole) and tri-n-butyltin hydride (0.424 ml: 1.53 mmole) are added. Under ice cooling palladium tetrakis(triphenylphosphine) (81 mg: 0.07 mmole) is further added. After stirring at the same temperature for 45 minutes and at room temperature for 1 hour, water (35 ml) and methylene chloride (50 ml) are added to the reaction mixture. The aqueous layer is taken, washed with methylene chloride and lyophilized to give (1R, 5S,6S)-6-[(1R)-1-hydroxyethyl]-2-[(3S,5S)-5-sulfamidomethylpyrrolidin-3-yl]thio-1-methyl-1-carba-2-penem-3-carboxylic acid (238 mg). Yield: 82%. (HPLC purity: 85%)

NMR δ (D$_2$O) ppm: 1.22(d, J=7.2 Hz, 3H), 1.27(d, J=6.3 Hz, 3H), 1.64 to 1.82(m, 1H), 2.62 to 2.80(m, 1H), 3.26 to 3.59(m, 5H), 3.63 to 3.76(m, 1H), 3.84 to 4.10(m, 2H), 4.16 to 4.29(m, 2H).

IR v (KBr) cm$^{-1}$: 1340, 1750.

EXAMPLE 14

Synthesis of a (3S,5S)-pyrrolidylthiocarbapenem derivative using a diallyloxycarbonyl intermediate

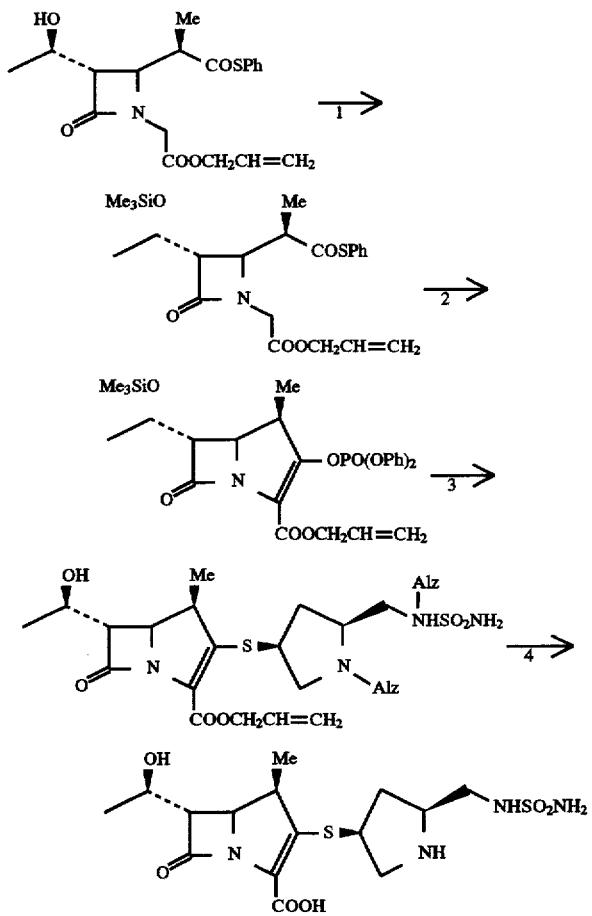

Step 1. Preparation of a trimethylsilyl compound (3S,4S)-3-[(1R)-1-hydroxyethyl]-4-[(1R)-1-phenylthiocarbonylethyl]-1-allyloxycarbonylmethyl-2-azetidinone is trimethylsilylated in the same manner as in Step 1 in Example 13 to give (3S,4S)-3-[(1R)-1-trimethylsilyloxyethyl]-4-[(1R)-1-phenylthiocarbonylethyl]-1-allyoxycarbonylmethyl-2-azetidinone.

Step 2. Ring closure

The crude (3S,4S)-3-[(1R)-1-trimethylsilyloxyethyl]-4-[(1R)-1-phenylthiocarbonylethyl]-1-allyloxycarbonylmethyl-2-azetidinone obtained in Step 1 is allowed to react to close the ring in the similar manner as in Step 2 of Example 13 to give crude (1R,5S,6S)-2-diphenoxyphosphoryloxy-6-[(1R)-1-trimethylsilyloxyethyl]-1-methyl-1-carba-2-penem-3-carboxylic acid allyl ester.

Step 3 Preparation of a protected pyrrolidylthio carbapenem derivative

Under similar reaction condition, the crude (1R,5S,6S)-2-diphenoxyphosphoryloxy-6-[(1R)-1-trimethylsilyloxyethyl]-1-methyl-1-carba-2-penem-3-carboxylic acid allyl ester (5.05 g: 8.3 mmole) obtained in Step 2 and (2S,4S)-1-allyloxycarbonyl-2-(N-allyloxycarbonyl-N-sulfamoylamino)methyl-4-mercaptopyrrolidine (3.77 g: 9.94 mmole) are reacted to give (1R,5S,6S)-2-[(3S,5S)-1-allyloxycarbonyl-5-(N-allyloxycarbonyl-N-sulfamoylamino)methylpyrrolidin-3-yl]thio-6-[(1R)-1-hydroxyethyl]-1-methyl-1-carba-2-penem-3-carboxylic acid allyl ester (3.65 g). Yield: 70%.

IR ν (CHCl₃) cm⁻¹: 1777, 1718, 1686, 1395.

NMR δ (CDCl₃) ppm: 1.27(3H, d, J=7.2 Hz), 1.37(3H, d, J=6.2 Hz), 2.5 to 2.7(1H, m), 3.1 to 3.3(3H, m), 3.6 to 3.8(2H, m), 4.0 to 4.3(4H, m), 4.4 to 4.9 (6H, m), 5.2 to 5.5(6H, m), 5.7 to 6.1(5H, m).

Step 4 Deprotection

Under similar reaction condition to that in Step 4 in Example 13, (1R,5S,6S)-2-[(3S,5S)-1-allyloxycarbonyl-5-(N-allyloxycarbonyl-N-sulfamoylamino)methylpyrrolidin-3-yl]thio-6-[(1R)-1-hydroxyethyl]-1-methyl-1-carba-2-penem-3-carboxylic acid allyl ester (369 mg: 0.586 mmole) is deprotected with triphenylphosphine (83 mg: 0.32 mmole), tri-n-butyltin hydride (0.64 ml: 2.3 mmole), and palladium tetrakis(triphenylphosphine) (122mg: 0.11 mmole) to give (1R, 5S,6S)-6-[(1R)-1-hydroxyethyl]-2-[(3S,5S)-5-sulfamidomethylpyrrolidin-3-yl]thio-1-methyl-1-carba-2-penem-3-carboxylic acid (206 mg). Yield: 84%. (HPLC purity: 85%)

NMR δ (D₂O) ppm: 1.22(d, J=7.2 Hz, 3H), 1.27(d, J=6.3 Hz, 3H), 1.64 to 1.82(m, 1H), 2.62 to 2.80(m, 1H), 3.26 to 3.59(m, 5H), 3.63 to 3.76(m, 1H), 3.84 to 4.10(m, 2H), 4.16 to 4.29(m, 2H).

IR ν (KBr) cm⁻¹: 3400, 1750.

EXAMPLE 15

A solution of (1R,5S,6S)-6-[(1R)-1-hydroxyethyl]-2-[(3S,5S)-5-sulfamidomethylphrrolidin-3-yl]thio-1-methyl-1-carba-2-penem-3-carboxylic acid (0.5 g) in aqueous sodium hydrogen carbonate (5 ml) at pH 7.0 is filled in a vial (10 ml) and lyophilized. The lyophilizate is dissolved in water for infection (5 ml) before use and injected thrice a day intravenously to a patient suffering from urinary tract infection caused by a sensitive strain of *Staphylococcus aureus* to cure the disease.

EXAMPLE 16

A solution of (1R,5S,6S)-6-[(1R)-1-hydroxyethyl]-2-[(3S,5S)-5-(methylsulfamoyl)aminomethylpyrrolidin-3-yl]thio-1-methyl-1-carba-2-penem-3-carboxylic acid (0.5 g) in aqueous sodium hydrogen carbonate (5 ml) at pH 7.0 is filled in a vial (10 ml) and lyophilized. The lyophilizate is dissolved in water for infection (5 ml) before use and injected thrice a day intravenously to a patient suffering from pneumonia caused by a sensitive strain of *Klebsiella pneumoniae* to treat the disease.

EXAMPLE 17

A solution of (1R,5S,6S)-6-[(1R)-1-hydroxyethyl]-2-[(3S,5S)-5-(2-hydroxyethylsulfamoyl)aminomethylpyrrolidin- 3-yl]thio-1-methyl-1-carba-2-penem-3-carboxylic acid (2.0 g) in aqueous sodium hydrogen carbonate (10 ml) at pH 7.0 is filled in vial (100 ml) and lyophilized. The lyophilizate is dissolved in water for injection (50 ml) before use and administered by infusion four times a day intravenously to a patient severely suffering from the respiratory tract infection caused by a sensitive strain of *Enterobacter cloacae* to cure the disease.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A pyrrolidine derivative represented by Formula II:

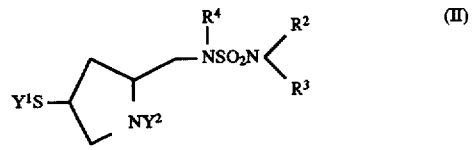

wherein R², R³ and R⁴ are hydrogen, lower alkyl which can be substituted, or an amino protecting group independently, or R² and R³ together with a nitrogen atom to which R² and R³ are bonded form a saturated or unsaturated cyclic group, or R² and R⁴, or R³ and R⁴ together with two nitrogen atoms and one sulfur atom in the sufamide group form a saturated or unsaturated cyclic group; each cyclic group can further include at least one atom selected from the group consisting of oxygen, sulfur and nitrogen, and each cyclic group can be substituted; Y¹ is hydrogen or a mercapto protecting group; and Y² is hydrogen or an amino protecting group.

2. A pyrrolidine derivative according to claim 1, wherein R⁴ is hydrogen.

3. A pyrrolidine derivative according to claim 1, wherein each of R² and R³ is hydrogen, R⁴ is an amino protecting group, Y¹ is hydrogen, and Y² is an amino protecting group.

4. A pyrrolidine derivative according to claim 1, wherein each of R² and R³ is hydrogen, R⁴ is t-butyloxycarbonyl, Y¹ is hydrogen, and Y² is t-butyloxycarbonyl.

5. A pyrrolidine derivative according to claim 1, wherein R² and R³ together with a nitrogen atom to which R² and R³ are bonded form a saturated or unsaturated cyclic group.

6. A pyrrolidine derivative according to claim 1, wherein R² and R⁴ together with two nitrogen atoms and one sulfur atom in the sulfamide group form a saturated or unsaturated cyclic group.

7. A pyrrolidine derivative according to claim 1, wherein R³ and R⁴ together with two nitrogen atoms and one sulfur atom in the sulfamide group form a saturated or unsaturated cyclic group.

8. A pyrrolidine derivative according to claim 1, wherein R², R³ and R⁴ are independently selected from hydrogen, hydroxy substituted lower alkyl, amino substituted lower alkyl, alkoxy substituted lower alkyl, acylamino substituted lower alkyl, lower alkylamino substituted lower alkyl, carbamoyl substituted lower alkyl, lower alkylcarbamoyl substituted lower alkyl, carbamoyloxy substituted lower alkyl, lower alkylcarbamoyloxy substituted lower alkyl, and cyano substituted lower alkyl.

9. A pyrrolidine derivative according to claim 1, wherein at least one of $R^2$, $R^3$ and $R^4$ is a lower alkyl which can be substituted, and the lower alkyl comprises 1 to 6 carbon atoms.

10. A pyrrolidine derivative represented by Formula II:

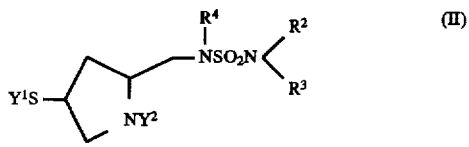

(II)

wherein $R^2$, $R^3$ and $R^4$ are hydrogen, lower alkyl which can be substituted, or an amino protecting group independently; $Y^1$ is hydrogen or a mercapto protecting group; and $Y^2$ is hydrogen or an amino protecting group.

11. A pyrrolidine derivative according to claim 10, wherein $R^2$, $R^3$ and $R^4$ are independently selected from hydrogen, hydroxy substituted lower alkyl, amino substituted lower alkyl, alkoxy substituted lower alkyl, acylamino substituted lower alkyl, lower alkylamino substituted lower alkyl, carbamoyl substituted lower alkyl, lower alkylcarbamoyl substituted lower alkyl, carbamoyloxy substituted lower alkyl, lower alkylcarbamoyloxy substituted lower alkyl, and cyano substituted lower alkyl.

12. A pyrrolidine derivative according to claim 10, wherein at least one of $R^2$, $R^3$ and $R^4$ is a lower alkyl which can be substituted, and the lower alkyl comprises 1 to 6 carbon atoms.

13. A pyrrolidine derivative according to claim 10, wherein $R^4$ is hydrogen.

14. A pyrrolidine derivative represented by Formula II:

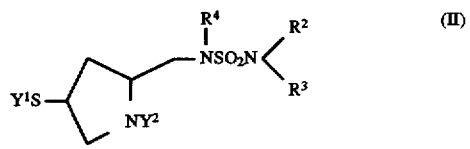

(II)

wherein $R^2$, $R^3$ and $R^4$ are independently hydrogen, or an amino protecting group, or an $R^2$ and $R^3$ together with a nitrogen atom to which $R^2$ and $R^3$ are bonded form a saturated or unsaturated cyclic group, or $R^2$ and $R^4$, or $R^3$ and $R^4$ together with two nitrogen atoms and one sulfur atom in the sulfamide group form a saturated or unsaturated cyclic group; each cyclic group can further include at least one atom selected from the group consisting of oxygen, sulfur and nitrogen, and each cyclic group can be substituted; $Y^1$ is hydrogen or a mercapto protecting group; and $Y^2$ is hydrogen or an amino protecting group.

15. A pyrrolidine derivative according to claim 14, wherein $R^2$ and $R^3$ together with a nitrogen atom to which $R^2$ and $R^3$ are bonded form a saturated or unsaturated cyclic group.

16. A pyrrolidine derivative according to claim 14, wherein $R^2$ and $R^4$ together with two nitrogen atoms and one sulfur atom in the sulfamide group form a saturated or unsaturated cyclic group.

17. A pyrrolidine derivative according to claim 14, wherein at least one $R^2$ and $R^3$, $R^2$ and $R^4$ and $R^3$ and $R^4$ form a saturated or unsaturated cyclic group, and the saturated or unsaturated cyclic group is selected from 1,1-dioxothiadiazinyl; 1,1-dioxodihydrothiadiazinyl; 1,1,3-trioxodihydrothiadiazinyl; 1,1-dioxothiadiazolizinyl; 1,1-dioxothiadiazolinyl; 1,1,3-trioxothiadiazolinyl.

18. A pyrrolidine derivative according to claim 14, wherein $R^4$ is hydrogen.

* * * * *